(12) United States Patent
Suhami

(10) Patent No.: US 7,304,309 B2
(45) Date of Patent: Dec. 4, 2007

(54) RADIATION DETECTORS

(76) Inventor: Avraham Suhami, 465 Willow Glen Way apt. 325, San Jose, CA (US) 95125

( * ) Notice: Subject to any disclaimer, the term of this patent is extended or adjusted under 35 U.S.C. 154(b) by 65 days.

(21) Appl. No.: 11/371,573

(22) Filed: Mar. 9, 2006

(65) Prior Publication Data

US 2006/0202125 A1   Sep. 14, 2006

Related U.S. Application Data

(60) Provisional application No. 60/703,149, filed on Jul. 29, 2005, provisional application No. 60/660,836, filed on Mar. 14, 2005.

(51) Int. Cl.
*G01T 1/20* (2006.01)
(52) U.S. Cl. .................................. 250/370.11
(58) Field of Classification Search ........... 250/363.02, 250/363.04, 370.09, 370.11
See application file for complete search history.

(56) References Cited

U.S. PATENT DOCUMENTS 6,717,174 B2 *   4/2004   Karellas ..................... 250/582

* cited by examiner

*Primary Examiner*—David Porta
*Assistant Examiner*—Marcus H Taningco

(57) ABSTRACT

The invention consists in structuring scintillation radiation detectors as Photonic Bandgap Crystals or 3D layers of thin filaments, thus enabling extremely high spatial resolutions and achieving virtual voxellation of the radiation detector without physical separating walls. The ability to precisely measure the recoil electron track in a Compton camera enables to assess the directions of the gamma rays hitting the detector and consequently dispensing with collimators that strongly reduce the intensity of radiation detected by gamma cameras. The invention enables great enhancements of the capabilities of gamma cameras, SPECT, PET, CT and DR machines as well as their use in Homeland Security applications. Methods of fabrication of such radiation detectors are described.

21 Claims, 37 Drawing Sheets

~frequency
$W = a/\lambda$

RADIATION DETECTORS

This provisional application claims the benefit of the filing of U.S. Provisional Patent Application Ser. No. 60/660,836 filed on Mar. 14, 2005 Titled: Photonic Bandgap scintillator crystals and U.S. Provisional Patent Application Ser. No. 60/703,149 filed on Jul. 29, 2005

FIELD OF THE INVENTION

This invention relates to radiation detectors

RELEVANT PATENTS

The patents below are incorporated in this application by reference.

U.S. Pat. No. 6,903,873 High omnidirectional reflector Joannopoulos, et al.
U.S. Pat. No. 6,906,559 Method and apparatus for gamma ray detection by Tümer; Tümay O.
U.S. Pat. No. 6,898,265 Scintillator arrays for radiation detectors and methods of manufacture by Mliner et al.
U.S. Pat. No. 6,892,011 Method and apparatus for fabrication of plastic fiber optic block materials and large flat panel displays by Walker, et al.
U.S. Pat. No. 6,881,959 Method and system for generating an image of the radiation density of a source of photons located in an object by Meng et al.
U.S. Pat. No. 6,859,607 Optical fiber, optical fiber cable and radiation detecting system using such by Sugihara et al.
U.S. Pat. No. 6,791,090 Compton deconvolution camera by Lin, et al.
U.S. Pat. No. 6,775,348 Fiber optic scintillator with optical gain for a computed tomography system, and method of manufacturing same by Hoffman et al.
U.S. Pat. No. 6,738,551 Two-dimensional photonic crystal and multiplexer/demultiplexer using the same by Noda, et al.
U.S. Pat. No. 6,704,391 B2 System and method of aligning scintillator crystalline structures for computed tomography imaging by Hoffman, et al.
U.S. Pat. No. 6,689,293 Crystalline rare-earth activated oxyorthosilicate phosphor by McClellan, et al.
U.S. Pat. No. 6,685,870 Method and apparatus for manufacturing photonic crystal element by Ukechi, et al.
U.S. Pat. No. 6,630,077 Terbium or Lutetium containing garnet phosphors and scintillators for detection of high energy radiation by Shiang, et al.
U.S. Pat. No. 6,624,945 Thin film filters using omnidirectional reflectors Fan, et al.
U.S. Pat. No. 6,603,911 Omnidirectional multilayer device for enhanced optical waveguiding Fink, et al.
U.S. Pat. No. 6,573,813 All-dielectric coaxial waveguide with annular sections by Joannopoulos, et al.
U.S. Pat. No. 6,541,836 Semiconductor radiation detector with internal gain by Iwanczyk, et al.
U.S. Pat. No. 6,528,795 Compton scatter imaging instrument by Kurfess, et al.
U.S. Pat. No. 6,512,232 Method and apparatus for improving the sensitivity of a gamma camera by Pehl et al.
U.S. Pat. No. 6,498,828 B2 System and method of computer tomography imaging using a cerium doped lutetium orthosilicate scintillator by Jiang
U.S. Pat. No. 6,496,632 Method of fabricating photonic structures by Borrelli, et al.
U.S. Pat. No. 6,484,051 Coincident multiple Compton scatter nuclear medical imager by Daniel; James
U.S. Pat. No. 6,470,127 Photonic band-gap light-emitting fibers by Voevodkin, George
U.S. Pat. No. 6,469,682 Periodic dielectric structure of the three-dimensional photonic band gap type and method for its manufacture by de Maagt, et al.
U.S. Pat. No. 6,468,823 Fabrication of optical devices based on two dimensional photonic crystal structures and apparatus made thereby by Scherer et al.
U.S. Pat. No. 6,466,360 B2 Photonic crystal and its fabrication by Tokushima
U.S. Pat. No. 6,448,560 Method and apparatus for gamma ray detection by Tumer; Tumay O.
U.S. Pat. No. 6,409,907 Electrochemical process for fabricating article by Braun, et al.
U.S. Pat. No. 6,420,711 Method and apparatus for radiation detection by Tumer; Tumay O.
U.S. Pat. No. 6,391,434 Composite scintillator material and method of manufacture by Duclos, Steven Jude
U.S. Pat. No. 6,384,400 High resolution and high luminance scintillator and radiation imager employing the same by Albagli, et al.
U.S. Pat. No. 6,358,854 Method to fabricate layered material compositions by Fleming, et al.
U.S. Pat. No. 6,358,441 Cubic garnet host with PR activator as a scintillator material by Duclos, et al.
U.S. Pat. No. 6,310,352 Radiation detection device by Gross et. al.
U.S. Pat. No. 6,262,830 Transparent metallo-dielectric photonic bandgap structure by Scalora; Michael
U.S. Pat. No. 6,236,050 Method and apparatus for radiation detection by Tumer; Tumay O.
U.S. Pat. No. 6,323,492 Method for improving the spatial resolution of a compton camera by Clinthorne Neal
U.S. Pat. No. 6,224,666 B1 Forging cylindrical alkali halide ingots into rectangular plates by Zwolinski et al.
U.S. Pat. No. 6,153,882 method and system for reading a data signal emitted by an active pixel in a sensor by Nygard
U.S. Pat. No. 6,153,011 'Continuous Crystal Plate Growth Process and Apparatus', K. A. Pandelisev
U.S. Pat. No. 6,093,347 Rare earth scintillator compositions by Lynch et al.
U.S. Pat. No. 6,090,674 Method of forming a hole in the sub quarter micron range by Hsieh, et al.
U.S. Pat. No. 6,080,989 Apparatus and methods for detecting and or imaging gamma radiation by Royle, et al.
U.S. Pat. No. 6,072,224 Monolithic x-ray image detector and method of manufacturing by Tyson, et al.
U.S. Pat. No. 6,071,339 'Continuous Crystal Plate Growth Process and Apparatus', K. A. Pandelisev
U.S. Pat. No. 5,955,749 Light emitting device utilizing a periodic dielectric structure by Joannopoulos et al.
U.S. Pat. No. 5,874,738 Scintillation crystal modules and methods of making the same by Scott R. Huth
U.S. Pat. No. 5,864,141 Compact high resolution gamma ray imaging for scintimammography and other medical diagostic applications by Majewski et al.
U.S. Pat. No. 5,841,141 Image reconstruction from V projections acquired by Compton camera Gullberg et al.
U.S. Pat. No. 5,784,400 Resonant cavities employing two dimensionally periodic dielectric materials Joannopoulos et al.
U.S. Pat. No. 5,772,905 Nanoimprint Technology by S. Y. Chou
U.S. Pat. No. 5,567,944 Compton camera for in vivo medical imaging of radiopharmaceuticals by Rohe, et al.

U.S. Pat. No. 5,445,846 X-ray imaging tube by Atsuya Yoshida
U.S. Pat. No. 5,391,878 Multiplexed fiber readout of scintillator arrays by Michael D. Petroff
U.S. Pat. No. 5,319,189 X-ray image intensifier tube having a photocathode and a scintillator screen positioned on a microchannel array by Beauvais et al.
U.S. Pat. No. 5,213,712 Lanthanum lutetium oxide phosphor with cerium luminescence by Dole; Stephen L.
U.S. Pat. No. 5,057,692 High speed, radiation tolerant, CT scintillator system employing garnet structure scintillators by Greskovich et al.
U.S. Pat. No. 4,985,633 Scintillator with alveolate structured substrate Vieux et al.
U.S. Pat. No. 4,940,901 X-ray imaging device by Henry et al.
U.S. Pat. No. 4,803,366 Input screen scintillator for a radiological image intensifier tube and a method of manufacturing such a scintillator by Rougeot et al.
U.S. Pat. No. 4,421,671 Rare earth doped yttria-gadolinia ceramic scintillators by Cusano, et al.
U.S. Pat. No. 4,466,929 Preparation of Yttria Gadolinia ceramic scintillators by vacum hot-pressing by Greskovich, et al.
US 20050265675 Method for producing parallel arrays of fibers by Welker, David J et al.
US 20050161611 Two-dimensional ionising particle detector by Disdier, Laurent et al.
US 20050152417 Light emitting device with an omnidirectional photonic crystal Lin, Chung-Hsiang
US 2005/0151145 Light emitting device with a photonic crystal by Lin, Chung-Hsiang; et al.
US 2005/0133725 CT detector array having non-pixelated scintillator array by Jiang, Haochuan et al.
US 2005/0126470 Template and methods for forming photonic crystals by Herman, Gregory S. et al.
US 2005/0082484 Scintillator compositions and related processes and articles of manufacture by Srivastava et al.
US 2005/0087724 Transparent polycrystalline ceramic scintillators and methods of preparing the same by Young Kwan Kim et al.
US 2004/0238747 Scintillator crystal method for making use thereof by Dorenbos et al.
US 2004/0218712 CT detector array having non-pixilated scintillator array by Jiang, Haochuan et al.
US 2004/0079890 Devices for imaging radionuclide emissions by Fraser, George William; et al.
US 2004/0031435 Method for fabricating optical fiber preform using extrusion die by Park, Yong
US 2003/0183772 Thick scintillation plate with internal light collimation by Schreiner, et al.
US 20050151145 Light emitting device with a photonic crystal by Lin, Chung-Hsiang; et al.
US 20050152417 Light emitting device with an omnidirectional photonic crystal by Lin, Chung

OTHER PUBLICATIONS

A Proposed gamma Camera by R. W. Todd, et al Nature, 251 (1974) 132.
A Si/CdTe Semiconductor Compton Camera—Shin Watanabe et al. April 2005 SLAC-PUB-11144
Compton Camera for Low Energy Gamma Ray Imaging in Nuclear Medicine Applications—James Walter LeBlanc,
Development of an advanced Compton camera with gaseous TPC and scintillator—A. Takada et al "arXiv":astro-ph/0412047 v1 2 Dec. 2004
First Coincidences in Pre-Clinical Compton Camera Prototype for Medical Imaging—A. Studen et al. Preprint submitted to Elsevier Science, 17th Sep. 2004
Event reconstruction for Advanced Compton telescopes, A. Zoglauer et al. public.lanl.gov/mkippen/actsim/papers/ZOGLAUER_HEAD2004.pdf
Intrinsic eigenstate spectrum of planar multilayer stacks of two-dimensional photonic crystals by K. H. Dridi, 19 May 2003/Vol. 11, No. 10/OPTICS EXPRESS 1158
Photonic Crystal Scintillating Fibers, by George Voevodkin, Intelligent Optical Systems, Inc.,
Spontaneous emission of organic molecules embedded in a photonic crystal, E. P. Petrov et al. Phys. Rev. Lett., Vol. 81, pp. 77-80, 1998.
"Photonic band structures", E. Yablonovich, J. Mod. Opt., Vol. 41, pp. 171-404, 1994
"Block-iterative frequency-domain methods for Maxwell's equations in a planewave basis," Johnson et al., Optics Express 8, no. 3, 173-190 (2001),
Photonic crystal design tools—Photon Design, 34 Leopold Street, Oxford OX4 1TW, UK
$LaBr_3:Cr^{3+}$ scintillator for gamma ray spectroscopy—K. S. Shah et al. LBNL 51793
"Inhibited spontaneous emission in solid-state physics and electronics," E. Yablonovitch Phys. Rev. Lett. 58, 2059-2062 (1987).
S. John, "Strong localization of photons in certain disordered dielectric superlattices," Phys. Rev. Lett. 58, 2486-2489 (1987).
J. D. Joannopoulos, et al "Photonic Crystals" (Princeton U. Press, Princeton, N.J., 1995).
"Potential for SPECT cameras utilizing photodiode readout of scintillator crystals W. W. Moses et al S.E. Life Science Division, Lawrence Berkeley Laboratory, Berkeley, Calif.
"Existence of a photonic gap in periodic dielectric structures," K. M. Ho, et al. Phys. Rev. Lett. 65, 3152-3155 (1990).
"Photonic band structure: the face-centered-cubic case employing nonspherical atoms," E. Yablonovitch, et al. Phys. Rev. Lett. 67, 2295-2298 (1991).
"Three-dimensionally periodic dielectric layered structure with omnidirectional photonic band gap," S. G. Johnson et al., Appl. Phys. Lett. 77, 3490-3492 (2000).
"Full three-dimensional photonic bandgap crystals at near-infrared wavelengths," S. Noda, et al. Science 289, 604-606 (2000).
"Drilled alternating-layer structure for three-dimensional photonic crystals with a full band gap," E. Kuramochi, et al J. Vac. Sci. Technol. B 18, 3510-3513 (2000). (C) 2003 OSA 19 May 2003/Vol. 11, No. 10/Optics Express 1156
"A new fabrication technique for photonic crystals: nanolithography combined with alternating-layer deposition," S. Kawakami, et al. Opt. Quantum Electron. 34, 53-61 (2002).
"Guided modes in photonic crystal slabs," S. G. Johnson, et al. Phys. Rev. B. 60, 5751-5758 (1999).
"Linear waveguides in photonic-crystal slabs," S. G. Johnson, et al., Phys. Rev. B. 62, 8212-8222 (2000).
"A dielectric omnidirectional reflector," Y. Fink et al, Science 282, 1679-1682 (1998).
"Omnidirectional reflection from a one-dimensional photonic crystal," J. N. Winn et al Opt. Lett. 23, 1573-1575 (1998).
"Dielectric omnidirectional visible reflector," M. Deopura et al. Opt. Lett. 26, 1197-1199 (2001).
"An all-dielectric coaxial waveguide," M. Ibanescu, et al. Science 289, 415-419 (2000).

Low-loss asymptotically single-mode propagation in large-core OmniGuide fibers,"—S. G. Johnson et al. Opt. Express 9, 748 (2001), "Mode density inside an omnidirectional mirror is heavily directional but not small," C. Hooijer et al. Opt. Lett. 25, 1666-1668 (2000).

"Block-iterative frequency-domain methods for Maxwell's equations in a planewave basis," S. G. Johnson et al. Opt. Express 8, 173 (2001), http://www.opticsexpress.org/abstract.cfm?URI=OPEX-8-3-173

"Omnidirectional absolute band gaps in two-dimensional photonic crystals," Z. Y. Li et al. Phys. Rev. B. 64, 153108-153112 (2001).

"Wavelength-scalable hollow optical fibres with large photonic bandgaps for $CO_2$ laser transmission," Temelkuran et al. Nature 420, 650-653 (2002).

Experimental efforts and results in Finding new heavy scintillators; by Stephen E. Derenzo and William W. Moses, Lawrence Berkeley Laboratory Report No. LBL-33295, 1992 http://breast.lbl.gov/~wwwinstr/publications/Papers/HvyScint.pdf Large Area Avalanche Photodiodes Challenge PMTs—B. Koren and M. Szawlowski, Advanced Photonix, Inc., Camarillo, Calif.

Recent Advances in Avalanche Photodiodes by J. Campbell et al IEEE Journal of selected topics in quantum electronics VOL. 10, NO. 4, July/August 2004 p. 777

Turning Crystal Growth on Its Side: A Revolutionary New Crystal Technique for Next-Generation Photolithography Lens Materials—A. Pandelisev, Single Crystal Technologies, www.sct-llc.com Development of a Novel Ultra-fast Scintillator with MQW Structure by K. Shibuya et al. in Ionizing Radiation Sensors, 2004

Gadolinium-Loaded Plastic and Rubber Scintillators by Zane W. Bell, Lockheed Martin Energy Systems, Inc.

High Refractive Index Polymer Coatings for Optoelectronics Applications—Brewer Science, Inc., 2401 Brewer Dr., Rolla, Mo., 65401 USA Imprint Lithography with 25-Nanometer Resolution—Stephen Y. Chou et al. Science, 272, 85, 1996

Laser-Assisted Direct Imprint—Chou et al Nature 2002, 417, 835-837

Scintillating Photonic Crystal for Medical imaging-Intelligent Optical Systems Inc.—www.intopsys.com Self-Collimating Phenomena in Photonic Crystals, Hideo Kosaka, et al., Applied Physics Letters, vol. 74, No. 9, Mar. 1, 1999, pp. 1212-1214

"Enhancement and Suppression of Thermal Emission by a Three-Dimensional Photonic Crystal," Lin, et al., Rapid Communications, Physical Review B 62 4, Jul. 15, 2000, R2243

Development of a Novel Ultra-fast Scintillator with MQW Structure by K. Shibuya et al. in Ionizing Radiation Sensors, 2004

Crystal Fiber technology; by Broeng et al. Technical University of Denmark www.crystal-fibre.com/publications/broeng_dopsnyt0200.pdf All the patents, patent applications and documents cited above are incorporated in this application by reference.

BACKGROUND

Photonic Bandgap Crystals (hereinafter PBC) are periodically structured materials characterized by ranges of frequency in which light cannot propagate through the structure. A PBC is generally composed of at least two materials differing in their refraction indexes, whose periodicity is approximately half the wavelength of light unable to propagate through the lattice. A complete photonic band gap is a range of frequencies in which there are no real solutions of Maxwell's equations. The theoretical treatment of the interaction of such periodic materials with electromagnetic radiation is analogous to the treatment in solid-state physics of the interaction of atomic lattices with electrons, showing the existence of distinct energy bands separated by gaps.

As actual photonic crystals are complex structures, in general it is hard to locate the bandgaps analytically. One method entails finite difference numerical analysis, calculating the evolution in time of the electromagnetic fields, thus extracting measurable quantities such as transmission or reflection. Another method consists in diagonalizing the Magnetic field Hermitian operator in the frequency domain, thus finding its eigenvectors, the allowed modes and extracting the band diagrams. See "Introduction to Photonic Crystals: Bloch's Theorem, Band Diagrams, and Gaps" by Steven G. Johnson and J. D. Joannopoulos, MIT 2003. 2D Photonic Crystal slabs and their bandgaps as a function of the dimensions and refractive indexes of the composing materials have been extensively investigated, see for example "Intrinsic eigenstate spectrum of planar multilayer stacks of two-dimensional photonic crystals" by K. H. Dridi Optics Express 2003/Vol. 11, No. 10/p 1156.

Simple two-dimensional PBCs structured for example by periodic holes in a high refractive index matrix, can exhibit polarization-dependent bandgaps, in the frequency ($w=a/\lambda$) versus the wavenumber (k) domain. These crystals, though, cannot confine electromagnetic radiation in the third dimension, due to the "leaking" of the transverse electromagnetic waves into the $3^{rd}$ dimension. Limiting the "thickness" of the slab and constricting the slab between two air boundaries, or low refraction index materials, can minimize the "leakage" into the third dimension. There are two basic topologies for 2D photonic crystals, low-index holes in a high index matrix or high index rods in a low index matrix.

The largest bandgaps in 2D PBG crystals are obtained with triangular lattices with very large, almost touching holes and when the dielectric constant contrast is large, $\epsilon \sim 12$ for example. Photonic Bandgap structures having high contrast refractive indexes, effectively act as mirrors. Moreover PBCs modify the spontaneous emission rate of excited atoms within the lattice, when the imbedded atom has an emission frequency in the bandgap. The absence of electromagnetic modes inside the photonic bandgap, causes atoms or molecules imbedded in the crystal, to be locked in an excited state relative to the ground state. Photonic Bandgaps can be switched on and off by rapidly changing the refractive index of a non-linear component of the PBC, electrically or optically.

A software program for computing the band structures (dispersion relations) and electromagnetic modes of periodic dielectric structures (the MIT Photonic-Bands MPB) is freely available for download from the www.ab-initio.mit-.edu/mpb website. Photonic Crystal design tools are also available commercially, for example from Photon Design ltd. Oxford, UK.

Gamma ray radiation such as, the 140 keV γ-rays emitted from technetium-$99^m$ or the 511 keV γ-rays emitted following the annihilation of positrons emitted from fluorine-18, are usually detected by scintillation crystal detectors such as NaI (Tl), CsI (Tl), $Bi_4GeO_4$ or $CdWO_4$ scintillators or semiconductor detectors such as Ge or CdZT. The γ rays interact with the atoms of the crystal through the Photoelectric or Compton effects and Pair generation processes. Table 1 gives the energy and atomic number dependency of the 3 processes.

TABLE 1

| Type of Interaction | Energy dependence | Z dependence (cm²/atom) | Z dependence (cm²/g) |
|---|---|---|---|
| Photoelectric | $E^{-3.5}$ | $Z^{4\ to\ 5}$ | $Z^{3\ to\ 4}$ |
| Compton | $E^{-0.5\ to\ -1}$ | Z | ~Z independent |
| Pair production | E to ln E | $Z^2$ | Z |

The energy transfer from a hard photon (hv) to an atomic electron (e) in the photoelectric effect is given by $E_e=hv-E_b$ where $E_b$ is the binding energy of the electrons of the stopping material. The atom excited by the stripping of one of its electrons, returns to its stable state by emitting one or more X-rays whose energies are determined by its discrete energy levels and denoted accordingly as the M, L or K X-rays.

In the Compton effect which is effective at higher energies and low Z elements, the incoming photons are scattered by the free electrons of the stopping material, imparting them part of their energy. The energy of the scattered gamma ray (1) is given by $$E_1 = hv' \, m_e c^2 / [1+\cos\theta+(m_e c^2/E_0)]$$

or $\cos\theta = 1 - (m_e c^2/E_e) + (m_e c^2/E_1 + E_e)$ the recoil electron's energy is given by $$E_e = hv' = [(hv)^2/m_e c^2(1-\cos\theta)]/[1+(hv/m_e c^2)(1-\cos\theta)]$$

The maximal energy of the recoil electron is therefore at $E_e\mathrm{max} = E/(1+m_e c^2/2E)$ The recoil angle $\phi$ of the electron, relative to the direction of the impinging gamma ray, is given by $$\cot\phi = 1 + (hv/m_e c^2)\tan(\theta/2)$$

It is important to note that following the momentum equalities, the incoming gamma ray, the scattered gamma ray and the recoil electron are all on the same plane.

The differential cross section of the Compton Scattering for unpolarized photons is given by the Klein-Nishina equation:

$$[d\sigma/d\Omega] = (r_e^2/2)(v'/v)^2[(v/v')+(v'/v)-\sin^2\theta]$$

where $r_e = (e^2/m_e c^2)$ is the "classical" radius of the electron equal to $2.82\ 10^{-13}$ cm This equation which assumes scattering by free electrons, has to be modified by a form factor S(k,k') at energies where the binding energies of the electrons become important, as compared with the energy of the gamma ray, causing the angular distribution in the forward direction to be suppressed.

In the pair production effect the two 511 Kev hard photons generated by the annihilation of the positron, again interact with the stopping material through the Compton or Photoelectric effects and cause ejection of electrons and their eventual absorption, as explained above.

The electrons so produced by the three processes are stopped in the crystal producing low energy photons in the visible range, along their track. If the crystal is transparent to these photons, they can emerge from the crystal and be detected by a photon detector such as a photomultiplier tube or a photo-diode.

The range of the knoked-off electron in the crystal can be obtained by observing that $$R(E_0) = \int_{E_0}^{0}(dx/dE)dE = -\int_{0}^{E_0}(\partial E/\partial x)^{-1}dE = \int_{0}^{E_0}(1/S)dE$$

and using the Bethe-Bloch equation for electron absorption in matter $$dE/dx = C[1/v]NZ\ln\{f(I,v)\},$$

where C is an empirical constant
v=velocity of incident particle; N=number of atoms per cm³; Z=atomic number of absorbing medium; I=the mean excitation energy; f=a function of I and v.

The electron's range in low Z materials and in the $0.01 \leq T \leq 2.5$ MeV range may be approximated by the empirical formula $$R = 0.412 T^{1.27-0.0954\ln T}$$

where R is the range in g/cm² units and T the kinetic energy of the electron in units of MeV The length of part of an electron track, may be calculated by observing that $E = \int (\partial E/\partial x)dx$; therefore the energy absorbed in part of the track is $$E_0 = (\partial E/\partial x)_{avg} \int_{R_0} dx =$$

$(\partial E/\partial x)_{avg} R_0$ giving for $R_0 = E_0 / (\partial E/\partial x)_{avg(R_0)}$.

Thus if the energy absorbed in this part of the track $E_0$ and the average differential absorption $(\partial E/\partial x)$ are known, the length of the portion of the track $(R_0)$ may be calculated.

The underlying principles of Compton Cameras, namely that knowing the energy of the scattered gamma ray $E_1$, the position of the subsequent (usually photo-electric) event and the energy of the recoil electron and the position of its track, enable to derive the direction of the incoming gamma ray, are self evident and follow from the Compton effect equations. The practical obstacles are the measurement of the electron's position before the scattering and the direction of its recoil after interaction with the incoming gamma ray. Numerous variations of two-detector geometries and schemes have been proposed, that consist in detecting the position of the gamma-electron interaction position with one detector and that of the subsequent photoelectric event with the second detector, in addition to their energies, in order to determine the direction of the incoming gamma ray on the "scattering plane". As the absolute direction of the "scattering plane" in space remains unknown, the absolute direction of the incoming gamma ray remains ambiguous and within a "cone" whose aperture is the scattered gamma ray's scattering angle relative to the incoming gamma ray in space.

In medical physics applications, as the "gamma ray-to-detector" distance is small (an approximation that is certainly wrong in case of astrophysics geometries), knowledge of the approximate direction of the incoming gamma ray, up to a cone, enables to approximately locate the position of the gamma source; moreover looking at the intersection of a number of "cones" enables to reduce the indeterminacy of the source position. A further reduction of this indeterminacy has been proposed by combining multiple pinhole collimators and the "Compton direction up to a cone" that consists in eliminating for each event, the pinholes that do not fall within the "cone", thus benefiting from the increased efficiency of multiple pinholes.

An additional uncertainty as to the direction of the recoil electron arises from the fact that the "free" electron is not at rest. If the electron's "motion" is taken into account, its recoil direction will not be exactly in the "scattering plane" but slightly out of it. This effect is sometimes referred to as the "doppler brodening" of the recoil electron's direction.

Radiation detectors are used in several healthcare instruments to map the radiation emitted by the body of a patient which has previously been injected with a radionuclide. Gamma Cameras endeavor to detect the location of the radiating source, by collimating the incoming radiation and then detecting the points of interaction of the collimated gamma rays with the radiation detector. Straight tubular collimators give a map of the radionuclides in the body of the patient, while pinhole collimators give the emission intensity coming from the focal point of the collimator, at the expense of blocking anything else. High resolution collimators immensely reduce the radiation intensity detected by the gamma camera and greatly increase the time needed for mapping the radionuclide distribution with acceptable spatial resolutions.

Gamma cameras with straight tubular collimators give a 2D projection of the radionuclide distribution, on the surface of the camera and cannot give depth information. SPECT (Single Photon Emission Computer Tomography) consists in rotating the Gamma Camera, to obtain several 2D maps from multiple directions and reconstruct the distribution along the third dimension, thus enabling to obtain a Tomographical image of the radionuclide distribution. Obviously dispensing with the collimator in SPECT is also of great benefit, reducing the scanning time or the amount of radionuclide injected or both.

PET (Photon Emission Tomography) consists in injecting the patient with a positron emitting radionuclide and detecting the annihilation pair of 511 keV gamma rays emitted in opposite directions, using two radiation detectors in time coincidence, thus determining a line that crosses the position of the radionuclide source. Detecting a multiplicity of such pairs of 511 keV gamma rays gives lines that crisscross the radiation source and enables to determine its position. The accuracy of the line crossing the radionuclide is determined both by the spatial extensions of the detectors and the exact location within the detector of the interacting gamma ray. Thus there is a need for a high efficiency and high spatial resolution gamma detector.

Cross section images of a body (slices) can be imaged by Computerized Tomography (CT) consisting in irradiating the body with intense X-rays from all 180° or more angles, detecting the unattenuated X rays that traversed the body using radiation detectors, and reconstructing a density map of the slice of the body traversed by the X rays, that is consistent with the integral absorption data obtained from all angles. The spatial resolution of such density images and the thickness of the slices, are dependent, inter alia, also on the spatial resolution of the radiation detectors. Multiple adjacent slices require thin adjacent detectors with minimal separating walls. A high spatial resolution continuous radiation detector therefore enables imaging a continuous multiplicity of thin slices and thus obtaining a continuous volumetric image.

Search of the previous art has not revealed any patent, patent application or publication that deals with scintillator fiber arrays structured as Photonic Bandgap Crystals, nor scintillator fiber arrays with an ability to find the position of the scintillation along the fiber.

SUMMARY OF THE INVENTION

The essence of the invention is to structure a radiation detecting scintillator, as an aggregate of 2D PBC planes built of properly spaced scintillation fibers, and several methods to find the location of a scintillation along the fiber. Such radiation detectors enable to find the 3D position of a scintillation with submicron spatial resolution. Such extremely high spatial resolution enable, inter alia, to satisfactory resolve the "cone ambiguity" of Compton Cameras.

It is important to note that unlike Photonic Bandgap Crystals structured to stop or guide light coming from outside the structure or "cavities" within the structure, Photonic Bandgap Crystal Scintillators (hereinafter PBCS) are structured to guide the scintillations generated internally from within the elements of the PBCS. This is an important distinction, as for example a wood-pile structure of bars or fibers known to have a complete bandgap in 3D, in respect to light coming from outside the structure, will let the scintillations generated inside the fibers to propagate out of the structure.

The ability to resolve the "cone ambiguity" has dramatic consequences, for example increasing the efficiency of Gamma and SPECT cameras by at least by two orders of magnitude. Consequently the injected radio-isotope doses may be decreased hundredfold or the radiation maps may be obtained as fast as obtaining a picture with an optical camera.

A two dimensional PBCS lattice may be built for example, by drilling periodic holes of appropriate diameter and distance one from the other, in the scintillator matrix or by structuring the lattice with properly spaced scintillator filaments separated by air. Single PBCS fiber too may be built by coating a scintillator fiber with successively alternating high and low refractive index coats or by surrounding it with several rings of "holes". Close packing PBCS fibers forms 2D arrays. The 3D position of an event may be obtained by stacking thin 2D PBCS lattices one orthogonally across the other, to form a woodpile-like lattice. Methods of building PBCS arrays are described below.

The order of magnitude of the lateral dimensions and separation of the holes or pillars in a PBCS is of the order of half the wavelength of the scintillations, for a CsI(Tl) crystal for example, around 200-250 nm. If the Bandgap covers part or the entire spectrum of the scintillator, lateral transmission of the scintillation light in those wavelengths will be inhibited within a few periods of the lattice, the scintillating light will only propagate in the allowed vertical direction. In case the PBCS is structured as an array of pillars, a second effect, critical angle reflection, has a large contribution to guiding part of scintillations generated within the scintillator fiber, to propagate along the fiber. The combined "Photonic Bandgap" and "Critical Angle Reflection" effects result in an effective focusing and collimation of a large part of the scintillation light along the fiber and its

SUMMARY OF THE INVENTION

The essence of the invention is to structure a radiation detecting scintillator, as an aggregate of 2D PBC planes built of properly spaced scintillation fibers, and several methods to find the location of a scintillation along the fiber. Such radiation detectors enable to find the 3D position of a scintillation with submicron spatial resolution. Such extremely high spatial resolution enable, inter alia, to satisfactory resolve the "cone ambiguity" of Compton Cameras.

It is important to note that unlike Photonic Bandgap Crystals structured to stop or guide light coming from outside the structure or "cavities" within the structure, Photonic Bandgap Crystal Scintillators (hereinafter PBCS) are structured to guide the scintillations generated internally from within the elements of the PBCS. This is an important distinction, as for example a wood-pile structure of bars or fibers known to have a complete bandgap in 3D, in respect to light coming from outside the structure, will let the scintillations generated inside the fibers to propagate out of the structure.

The ability to resolve the "cone ambiguity" has dramatic consequences, for example increasing the efficiency of Gamma and SPECT cameras by at least by two orders of magnitude. Consequently the injected radio-isotope doses may be decreased hundredfold or the radiation maps may be obtained as fast as obtaining a picture with an optical camera.

A two dimensional PBCS lattice may be built for example, by drilling periodic holes of appropriate diameter and distance one from the other, in the scintillator matrix or by structuring the lattice with properly spaced scintillator filaments separated by air. Single PBCS fiber too may be built by coating a scintillator fiber with successively alternating high and low refractive index coats or by surrounding it with several rings of "holes". Close packing PBCS fibers forms 2D arrays. The 3D position of an event may be obtained by stacking thin 2D PBCS lattices one orthogonally across the other, to form a woodpile-like lattice. Methods of building PBCS arrays are described below.

The order of magnitude of the lateral dimensions and separation of the holes or pillars in a PBCS is of the order of half the wavelength of the scintillations, for a CsI(Tl) crystal for example, around 200-250 nm. If the Bandgap covers part or the entire spectrum of the scintillator, lateral transmission of the scintillation light in those wavelengths will be inhibited within a few periods of the lattice, the scintillating light will only propagate in the allowed vertical direction. In case the PBCS is structured as an array of pillars, a second effect, critical angle reflection, has a large contribution to guiding part of scintillations generated within the scintillator fiber, to propagate along the fiber. The combined "Photonic Bandgap" and "Critical Angle Reflection" effects result in an effective focusing and collimation of a large part of the scintillation light along the fiber and its immediate neighbors that pick up the evanescent waves. Photo-electric sensors, positioned at the end of the fibers will give the 2D (x,y) position of the scintillation.

The outputs of the top and bottom photo detectors together determine the amplitude of the scintillation, while the asymetry between the out-the-bandgap photons scattered to the neighboring fibers and subsequently propagate upwards or downwards, is proportional to the position of the scintillation along the fiber.

A more precise location may be determined by structuring the radiation detector as a "woodpile" of thin PBCS lattices, one orthogonal to the other. The coordinates in 3D of an ionizing track traversing several such PBCS "slices", may be determined by registering the 2D coordinates in sequential slices. In this case the variance of the coordinates is given by the thickness of such "slices".

The channeling of a large portion the scintillator's light in tubular perpendicular directions enables effective collection of scintillation photons and their extraction from the scintillator with minimal reflection, scattering and absorption. Consequently the practical energy resolutions obtainable with modern high light ouput scintillators is dramatically better than with the legacy large scintillators suffering from multiple scatterings and absorption. Thus for example a photo-electron ejected by a technetium-99$^m$ 140 Kev γ-ray, produces approximately 11000 photons in a Lanthanum Chlorine Bromide crystal. Converting these photons by a photo-diode with Q.E.>60% 6600 photoelectrons will be generated leading to an energy resolution of 1.7 keV, obviously much better than with NaI(Tl) crystals and only slightly worse than semiconductor detectors. However the coordinates of an ionizing event in 3D would be determined with sub-micron resolution, 2-3 orders of magnitude better than Anger type or segmented semiconductor detectors. Another consequence of the virtual pixellation of the PBCS radiation detector is the immense reduction of the total dead time, as only the scintillation fibers guiding the photons are unable to detect another simultaneous event.

As most scintillators emit a spectrum larger than the practical bandgaps obtainable, given their refractive indexes, a trade-off between spatial resolution and bandgap may be achieved by structuring the PBCS out of "islands" structured to have different but adjacent Bandgaps, covering together the scintillator's entire spectrum. This strategy decreases the resolution to 1-2 "islands".

The much higher resolutions obtainable with Photonic Bandgap Crystal Scintillators require an immense number of pixels in the photo-diode arrays. Thus for 2µ resolution elements a 12"×12" crystal would require a detector array of 2.25 10$^{10}$ pixels. Such a large number of photo-sensors may be accomodated with a 12" wafer sized array of CMOS photo-sensors backed by "Active Pixel" electronics placed immediately beneath the photo-converter for converting the stream of photons to photo-electrons. As the need is to measure the energy, timing and position of the track of an ionizing event, simultaneously at all the pixels effected, the optimal electronics adopted is to divide the entire array into sub-arrays [(512µ)×(512µ) sized mosaics] of the approximate size of the expected dimensions of a track and perform the processing at the sub-array level. The sub-arrays are also connected in "rows" and "columns" and ionizing tracks extending across several sub-arrays have their processing done at the array level. In such a distributed geometry the Active pixels behind each resolution element, limited to a small area, could be very simple, 4-5 transistors, while the processors behind each mini-mosaic, would do most of the processing.

The high concentration of photons leaving the crystal perpendicularly through a basic resolution element, also allows an alternative optical solution using a two dimensional optical matrix and transporting the optical "information" to a place where physical space is not constrained. There after the optical-to-electronic conversion, the collected information could be processed without the space constraints.

The good energy and exquisite spatial resolutions obtainable with PBCS radiation detectors, enables the full reconstruction of the Compton effect interaction of a gamma ray with the detector. As mentioned in the Background section, to fully reconstruct a Compton scattering event requires determination of the recoil electron's track's direction or at least an additional point on its track that lies on the "scattering plane", as knowledge of three points on the incoming gamma ray ($\gamma_0$), the scattered gamma ray ($\gamma_1$) and the recoil electron track determine the "scattering plane" unambiguously. The recoil electron's direction or the determination of the third point on its track, is done on the very initial part of the electron's track, before the cumulative Coulomb interactions substantially change its direction. As determining this direction is critical, the scattering PBCS material is selected to have a low "mean excitation energy" and an effective density as low as possible, by structuring it as a fiber array of a "honeycomb" geometry, which is consistent with obtaining large bandgaps.

The ability to determine the direction of the incoming gamma rays, with a small dispersion, without the "cone ambiguity" has some dramatic consequences in the applications of radiation detectors. Getting rid of the collimator, used to determine direction, increases the detection efficiencies of collimated gamma cameras, by at least a factor of $10^4$, allowing to use a thin, mostly empty, low Z, PBCS that has a low absorption efficiency of gamma rays of ~10%, to register the Compton scattering event followed by the absorption of the scattered gamma ray through a photo-electric effect. Alternatively the gamma ray scattered, in a low Z PBCS lattice may be detected by a high Z PBCS detector, enabling together to determine the direction of the incoming gamma ray with high accuracy. However as the photo-electric event recorder can in practice cover only part of the solid angle around the Compton scatterer, there is another loss of efficiency. In both cases the detection efficiency is $10^2$ times lower than a single high Z scintillator; but taking in account the gain of $10^4$ due to the absence of a collimator, a PBCS Compton camera is still $10^2$ times more efficient Finding the minimal angular variance of the incoming gamma ray, dictates measuring the scattered gamma rays at preferred angles that take into account an optimal energy of the recoil electron that will result in a variance of the same magnitude as when finding its direction. The inclusion of only of a preferred range of angles that optimize the total angular variance of the incoming gamma ray, is a trade-off between efficiency and angular resolution.

The ability to determine the direction of the incoming gamma rays enables to use a stationary gamma camera as a tomograph; rotating it around the object like a SPECT camera improves the spatial resolution, while having a much higher efficiency. A Positron Emission Tomograph (PET) may be structured out of opposite PBCS Compton cameras or one circular PBCS Compton camera surrounding the patient, that confirm the directions of coincident annihilation gamma rays, but also reject scattering events that still are in coincidence. In a regular PET scanner, a PBCS radiation detector with its virtual voxels without physical walls, enables to use thick detectors at very high spatial resolution, leading to improved overall resolution of the source location in 3D.

A most important corollary of the fact that a PBCS Compton Camera is able to determine the direction of the incoming gamma rays, is that Tomographical images can be obtained without Positron Emitters. Radio-isotopes emitting a cascade of gamma rays may be used to determine the location of the radiation source.

CT scanners may use the pixellated, but without walls, thick PBCS radiation detectors, enabling thinner slices and higher spatial resolutions, both leading to better volumetric images.

Digital X-ray radiography may also benefit from the virtual pixellation of the thick PBCS radiation detector structure that allows full absorption at high X-ray energies, while achieving an order magnitude better spatial resolutions than the current technology.

The implications of PBCS Compton cameras for Homeland Security applications are dramatic. Detecting the direction of the γ rays enables Tomographic imaging and discards the non-directional background, while real time Dynamic imaging, differentiates a "moving source" from all static sources of background: The ability to subtract background without shielding and collimation enables a lightweight portable radiation camera that multiplies its deployment areas.

Currently the great majority of Photonic Bandgap Crystals manufactured are of 2D slab variety. The exceptions are the 3 dimensional opals. Only "omnidirectional" and "holey" fibers are commercially available although not with scintillator cores. In the sections below we describe methods to build large PBCS arrays starting with PBC fibers.

Large PBCS arrays may be built by a combination of methods borrowed from different industries. The processes we describe below consist in first preparing a mold or filter having the desired 2D PBC structure "holey" using one of the Femtolaser ablating, nano-imprinting, plasma etching or chemical etching technologies. At the next stage a second mold is prepared by extruding a heat liquefied material or a photopolymer through the mold with sub-micron holes and thus forming a large 3D structure of tubular elements. The space between the thin filaments may be filled by an aerogel that keeps the structure mechanically rigid. For some scintillators the process ends here; if the material extruded is a scintillator, the 3D structure formed is the desired PBCS structure.

The extruded PBC structure of pillars can at its turn be used as a template to prepare a "holey" PBC of the same geometry, which again if the material poured between the pillars is a scintillator, the structure so formed is a PBCS of holes. However if a PBCS of pillars of a material that could not be initially extruded, is desired, then the "holey" structure so formed may be used to prepare a crystalline PBCS structure. This may be accomplished by filling the holes of the mold with an ultrafine powder of the scintillator and using a somehow modified existing crystal growth technology, crystallize the scintillator structure. The mold then can be destroyed by chemical etching or if it is brittle, by shattering it with ultrasound. There are obviously constraints in all these manipulations that have to be observed such as the differential melting temperatures of the mold and that of the crystalline substance.

BRIEF DESCRIPTION OF THE DRAWINGS

The drawings of the application are not intended to portray the specific parameters or the structural details of the invention and are not to scale, but merely schematic representations of the invention, which illustrate to persons skilled in the art the main details of the invention after reading the information contained herein.

DETAILED DESCRIPTION OF THE PREFERRED EMBODIMENTS

Figure 1:
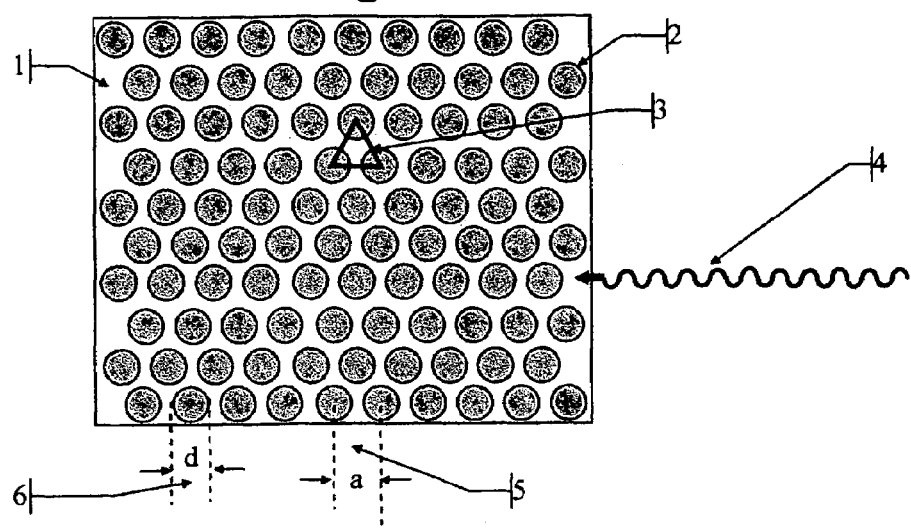
FIG. 1 illustrates a rectangular 2D PBC in the form of a triangular lattice of holes in a dielectric medium or a structure of high dielectric constant pillars in air or low dielectric constant medium.

FIG. 1 illustrates a triangular periodic lattice of a 2 dimensional Photonic Bandgap Crystal Scintillator (PBCS) viewed from above. The structure may be interpreted as holes 2 ($n_0=1$) in a high index matrix 1, for example in a CsI scintillator ($n_1=1.95$) or as pillars 2 separated by air or aerogel.

Figure 5:
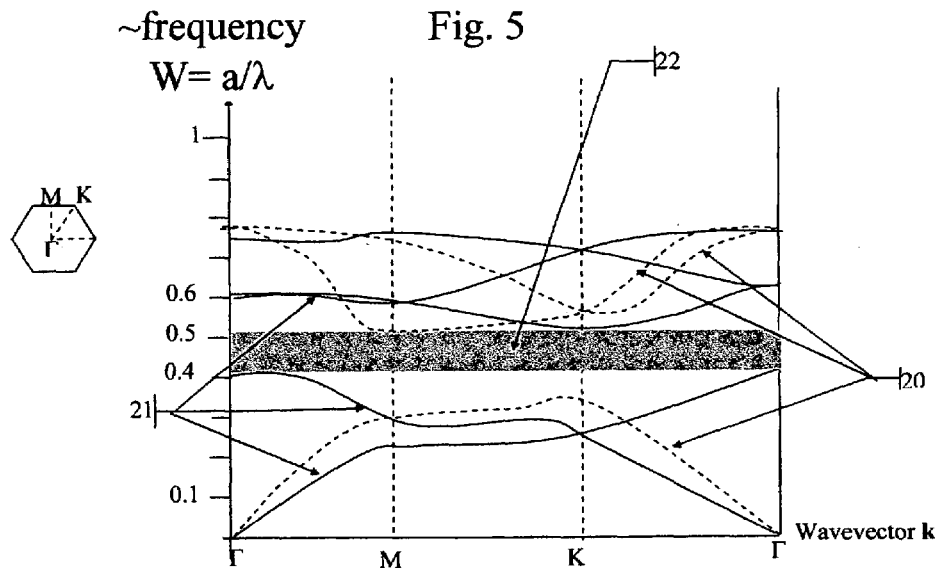
FIG. 5 illustrates the propagation modes and the Bandgap in a PBC of an open hexagonal lattice of pillars in air.

The lateral dimensions of the columns or holes (d) 6 and the distance (a) 5 between them, together with their respective dielectric constants determine the behavior of such structures in respect to the propagation of electromagnetic radiation across the 2D plane. From an extrapolation of the behavior of one dimensional Bragg gratings, we can guess that destructive interference in two dimensional lattices too, will occur for approximately half-wavelength interference for distances between the holes (or columns) forming the lattice. As an incoming beam 4 will be refracted from each layer of columns (or holes), the distances it travels between successive refractions changes; as a result there is a range of wavelengths where destructive interference will prevail after traversing a certain number of layers. This range of wavelengths where destructive interference prevails is the "Bandgap" 22 as illustrated in FIG. 5. Drilling "holes" of diameter (d) at a distance (a~$\lambda$/2=240 nm) one from the other for example in a high refractive index material, for example in a Bismuth Germanate (BGO) scintillator ($n_1$=2.15 $\lambda_{peak}$=480 nm), will give a two dimensional PBCS with a bandgap in the vicinity of 240 nm. Other examples of PBCS detectors include holes in high light output-high refractive materials such as Lanthanum Chloride Bromide ($n_1$=1.9, $\lambda_{peak}$=350 nm) or glass scintillator columns ($n_1$=1.46 $\lambda_{peak}$=465) in a silicon ($n_1$=3.45) matrix.

Figure 2:
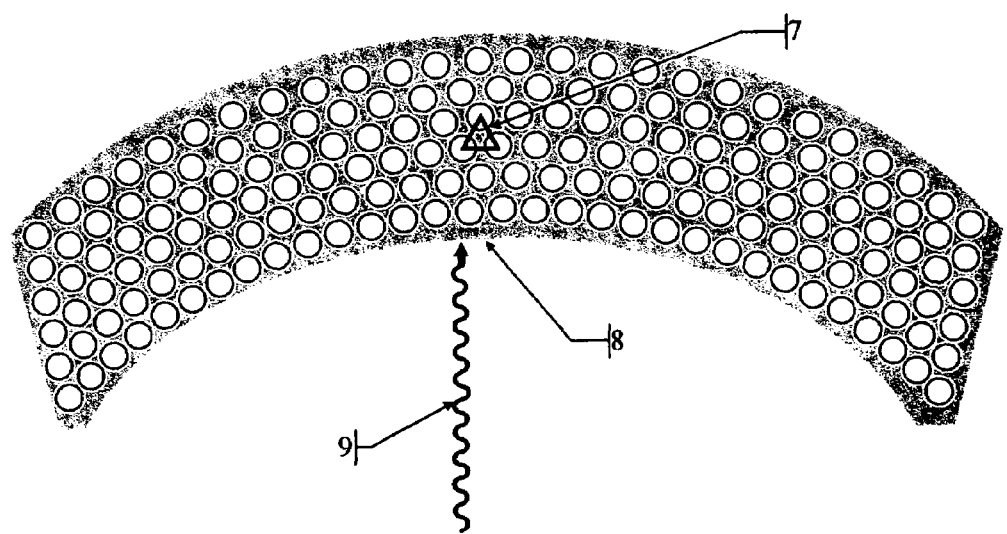
FIG. 2 illustrates a curved two dimensional PBC.

FIG. 2 illustrates a PBCS that is curved at macroscopic dimensions, although at the micro-dimensions of several wavelengths of visible light, it may be viewed as a rectangular structure as that illustrated in FIG. 1. Curved PBCS detectors are usefull for detecting point sources.

Figure 3:
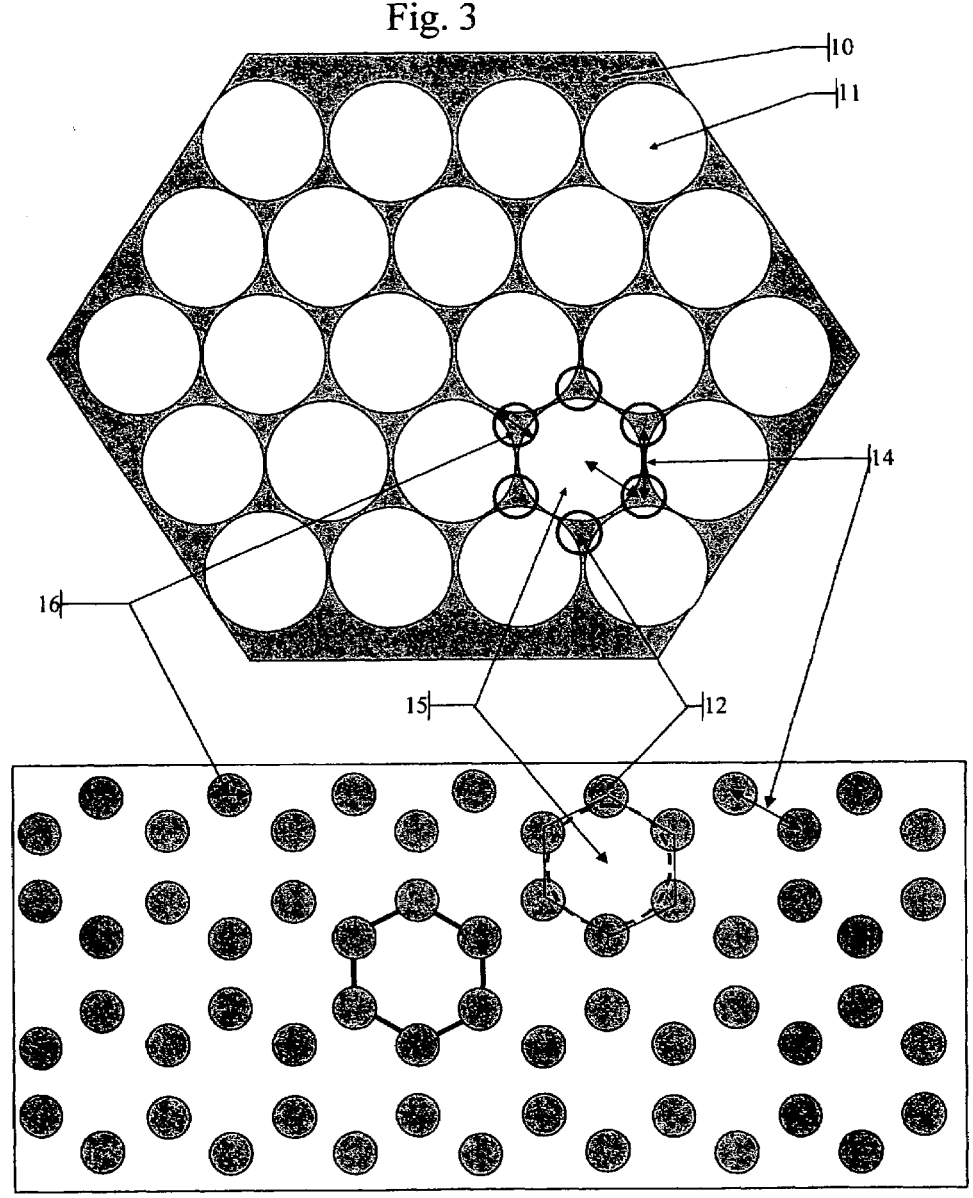
FIG. 3 illustrates a 2D PBC in the form of a triangular lattice of very large holes in a scintillator and its semi-equivalent structure consisting in an open hexagonal lattice of scintillation rods.

FIG. 3 illustrates a triangular PBCS lattice 10 with large, almost touching, air or aerogel holes 11 and an almost equivalent structure of scintillator fibers 12, each fiber having a diameter 16 of (⅓) the diameter of the large holes. Although both structures are almost equivalent from a PBCl point of view, the manufacturing process of the fibers structure is much easier.

Figure 4:
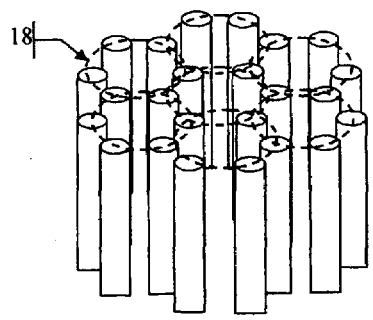
FIG. 4 illustrates a side view of two lattices of 2D PBCS rods, one in the form of an open hexagonal lattice and the second in the form of a triangular lattice.
Figure 4:
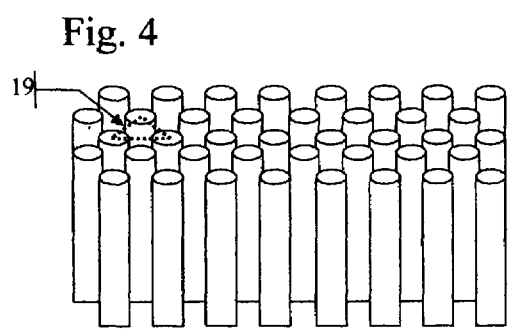

FIG. 4 illustrates a side view of two lattices of 2D PBCS fibers, one in the form of an open hexagonal "Honeycomb" lattice 18 as shown in FIG. 3, and the second in the form of a triangular lattice 19.

FIG. 5 shows the allowed modes of propagation of TM 20 and TE 21 modes of electromagnetic waves in a 2D photonic crystal and the frequency range 22 where no guided modes can exist, using the solid state physics formalism of displaying in a reciprocal k-space the dispersion relation of energy/frequency (w=a/$\lambda$) as a function of momentum (k) in a primitive cell of the periodic lattice.

We can intuitively see, that as the contrast in refractive indexes increases, the reflection at each interface will be larger and the change in direction of the propagating lightwave more abrupt, increasing the odds of scattering. An additional parameter to consider generally is the polarization of the electromagnetic wave as the propagation of the orthogonal TE and TM modes may exhibit different prohibited bands; unpolarized light will exhibit a full bandgap only at those wavelengths where these prohibited bands overlap.

Photonic bandgap Crystals are complex structures and hard to analyse analytically although many of its features may be extracted intuitively from their analogy with the behavior of electrons in a crystal. A software program for computing the band structures and electromagnetic modes of periodic structures is freely available for download from the MIT website www.ab-initio.mit.edu/mpb/. The range of wavelengths, which absolutely cannot propagate across the lattice, is usually narrow.

Figure 6:
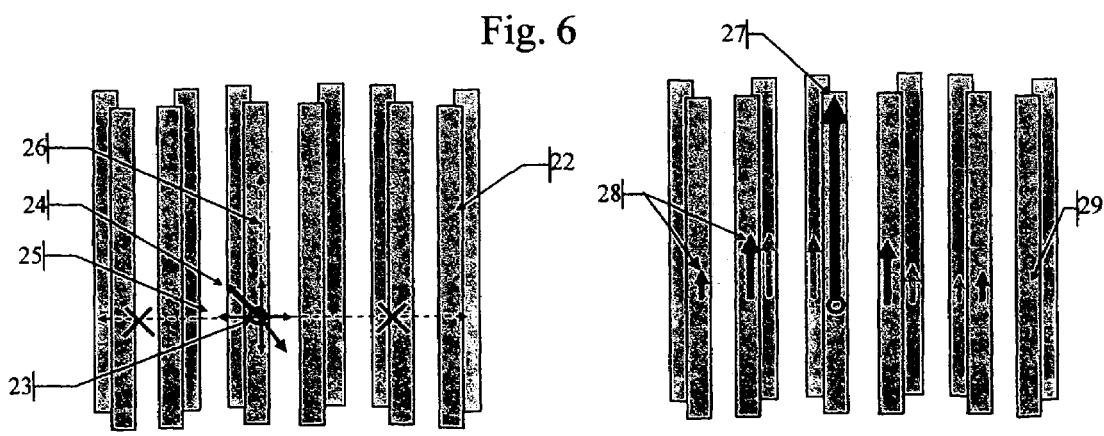
FIG. 6 illustrates the consequences of a two dimensional bandgap inhibiting spontaneous emission of light on the lateral plane and reinforcing the spontaneous emission along the third dimension, orthogonal to the lateral 2D plane.
Figure 12:
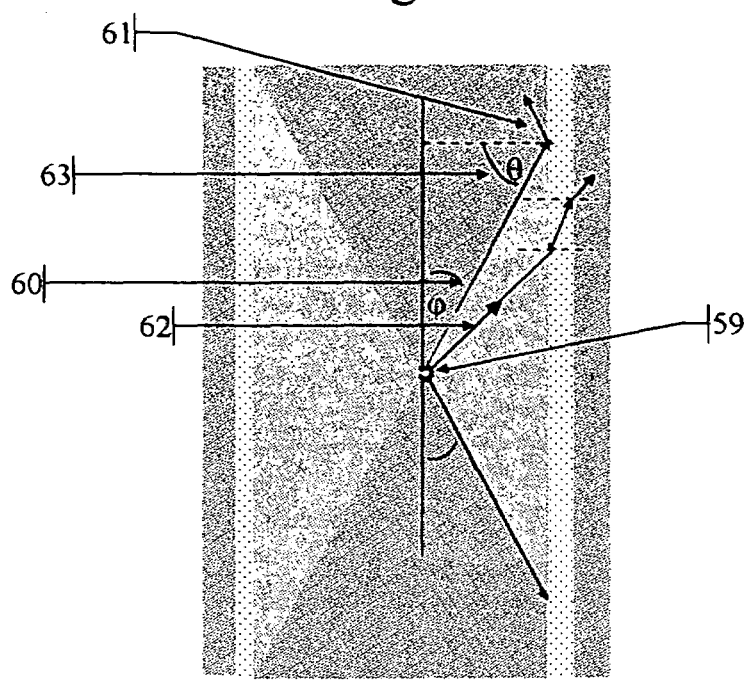
FIG. 12 illustrates the propagation of scintillations in a fiber in a low dielectric constant matrix.

In a scintillator filament, the scintillation light is emitted in all directions; however as illustrated in FIG. 12 "critical angle reflection" 64 given by sin $\theta$=1/$n_1$, causes the portion of the light within the cone defined by 2(90°−$\theta$) to propagate within the fiber up or down. For example in Scintillator fibers made of Lanthanum Chloride Bromide [La($Cl_{0.34}Br_{0.66})_3$:$CeCl_3$] having a refractive index of 1.9 surrounded by air (or an aerogel of density of 1.08), 48% (45%) in case of aerogel of the light will propagate up or down the fiber due to Total Internal Reflection (TIR). If as illustrated in FIG. 6 the surrounding structure is a PBCS lattice, propagation in the 2D plane will be prohibited from a quantum mechanical point of view. The omnidirectional spontaneous emission from excited states will be redistributed; emission through the lateral "guided modes" will be inhibited and the "vertical modes" enhanced, the propagation will only proceed in the "allowed" orthogonal directions. A simpler explanation is that scintillation photons 24 that might propagate in an angle to the 2D plane, may be viewed as having a lateral component 25 in the 2D plane which is prohibited and a vertical component orthogonal to the 2D plane 26, which is allowed to propagate. In a PBCS lattice as the cross section and separation of the fibers is smaller than the wavelength of the propagating light the vertically propagating electromagnetic wave will spread laterally and the evanescent wave will couple with one or more "rings" of adjacent filaments 28.

This process is similar to the behavior of guided light in PBC "holey" fibers, having a solid core surrounded by a multiplicity of air hole rings, that inhibit lateral propagation and force the electromagnetic wave to propagate along the core.

If the structure does not meet the distances and dimensions of a Photonic Bandgap Crystal, or if some of the scintillation spectrum falls outside the bandgap, the light 68 not guided bt TIR leaves the scintillator fiber, crosses the air (or aerogel) gap between the fibers and after being partially reflected, enters the adjacent fibers, is further scattered and ultimately exits the structure through the fibers around the fiber where the original scintillation occurred.

Figure 7:
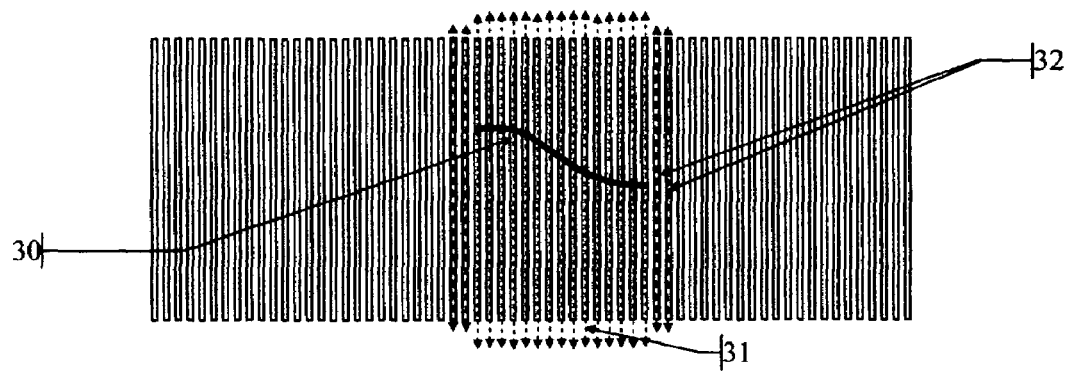
FIG. 7 illustrates the propagation of the scintillation photons engendered by an ionizing track, along the nanofibers of the PBC scintillator.

As illustrated in FIG. 7, unless there is a reflector on the top or bottom of the 2D plane, the light emitted by the deexcitation of the scintillator, following the excitation caused by an interaction with a charged particle 30, will exit the PBCS lattice through the $3^{rd}$ dimension 31, which is precisely what is needed for locating the coordinates of the interaction of the charged particle with the crystal, with a lateral spread of one or two periods 32 of the lattice.

Figure 8:
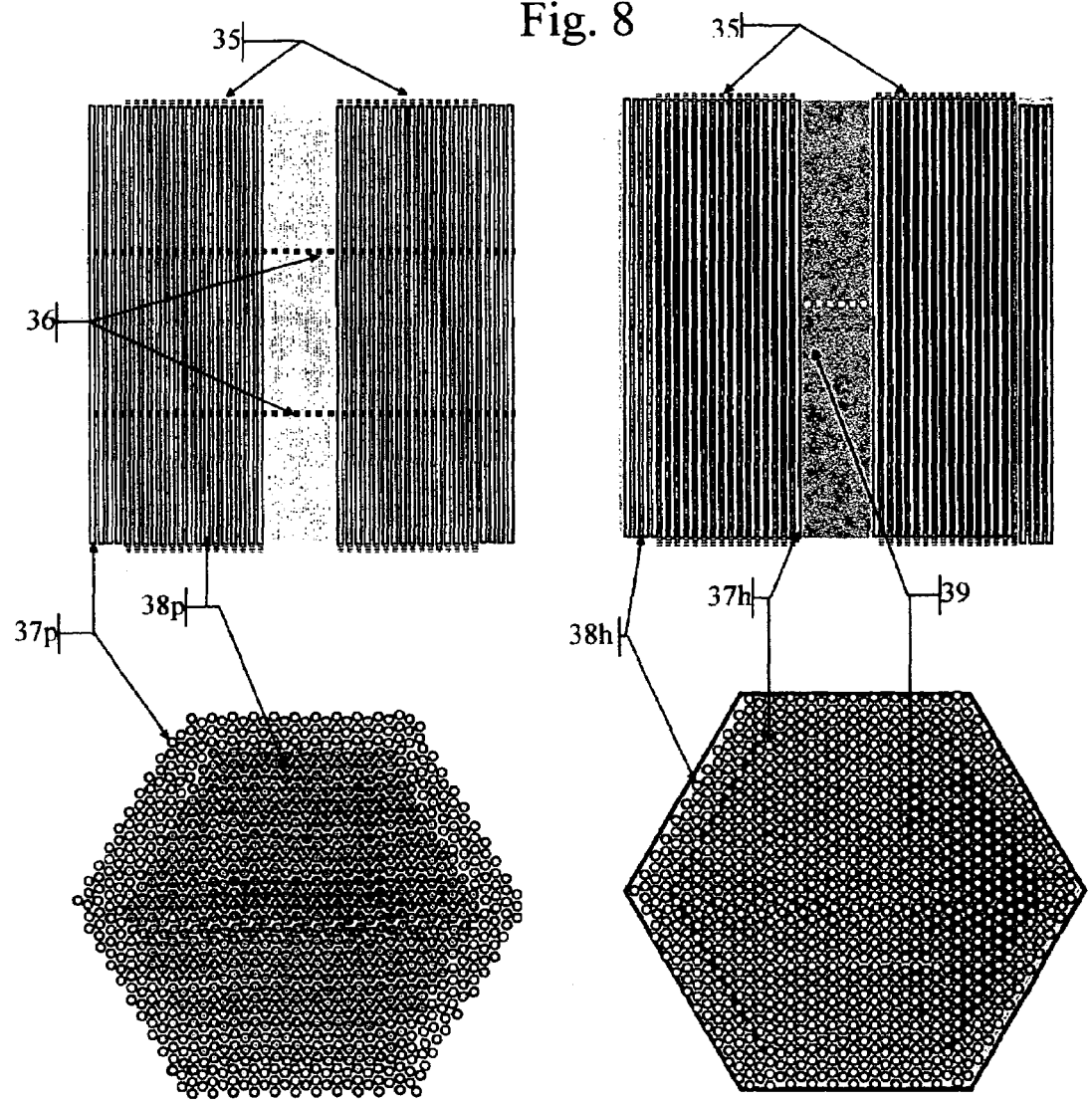
FIG. 8 illustrates PBCS arrays formed respectively by pillars or holes and surrounded at their periphery by non-scintillating photonic bandgap crystal guard strips.

FIG. 8 illustrates views from above and the side of 2 PBCS lattices formed by high refractive scintillator filaments in air 38p and holes 37h in a high refractive index matrix 39. The free standing scintillator filaments structure may be reinforced at several places 36 along their length to maintain rigidity of the structure or may be surrounded by aerogel with a density of 1.08 close to air. The scintillator structure may be surrounded by several rings of non-scintillating filaments 38p or a holey matrix 38h of the same refractive index, to serve as a conduit of the evanescent waves generated at the periphery of the scintillation structure. The top and/or bottom of the scintillating structures may be coated with dielectric or metallic mirrors to reflect back the desired part of the spectrum towards the other end.

Figure 9:
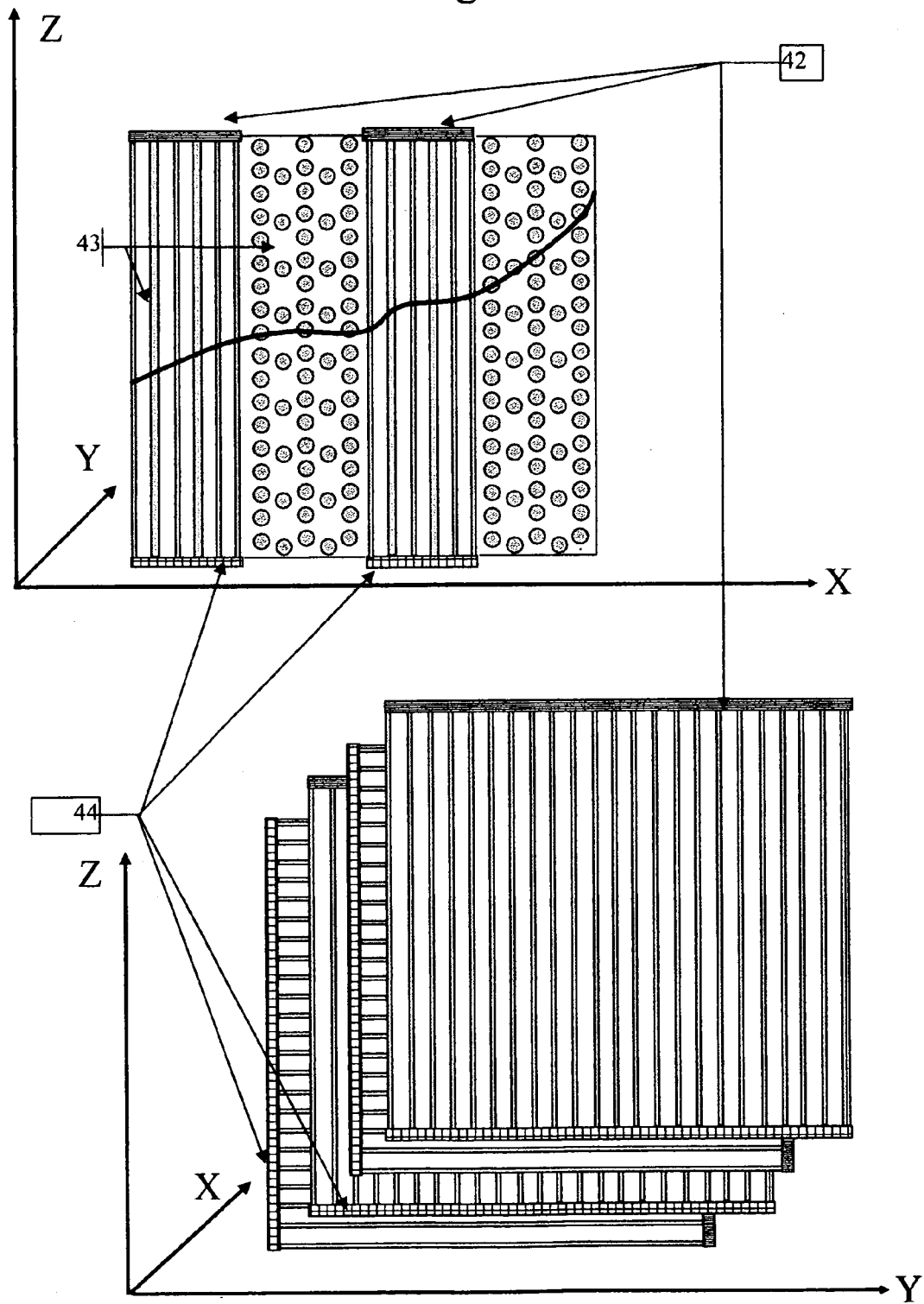
FIG. 9 illustrates two views of a 3D PBCS arrays formed by criss-crossed thin 2D PBCS open hexagonal lattices of nanofibers, coated at one end by mirrors and at the other end by photo-sensors.

FIG. 9 illustrates two views of a 3-dimensional lattice, in the form of 2D planes of PBCS layers 43 composed of scintillator fibers in an aerogel matrix stacked one on top of the other as a "wood-pile". The "wood-pile" is formed by piling sets of multiple 2D layers orthogonally, one on top of the other. If the "thickness" of a multilayer is of the order of several multiples of the number of periods needed to establish a "bandgap", a scintillation occurring within a multilayer, would only propagate in the vertical direction, orthogonal to the 2D plane and exit the multilayer at the edge of the crystal, where it can be sensed by a photodetector 44. At the interface between two multilayers, the photons would propagate across the boundary, from one multilayer to the next, which is orthogonal to the direction of the previous multilayer; however as this multilayer also has the same bandgap, albeit in an orthogonal 2D plane, the photons would be able to propagate there only in the "allowed" direction orthogonal to this 2D plane and would exit the multilayer at the edge 44 of the crystal, orthogonal to the exit direction of the previous multilayer. Thus a track of photoelectrons in a scintillator, say 100μ long, traversing 50 criss-crossed multilayers, each 2μ thick, would generate scintillations in 25 multilayers where the photons would propagate in the Z direction orthogonal to the XY plane, while the scintillations generated in the other alternating 25 multilayers would propagate in the Y direction orthogonal to the XZ plane. In this way the coordinates (x,y,z) of the track in space could be determined with an accuracy of up to the thickness of a multilayer, in this case 2μ.

Figure 10:
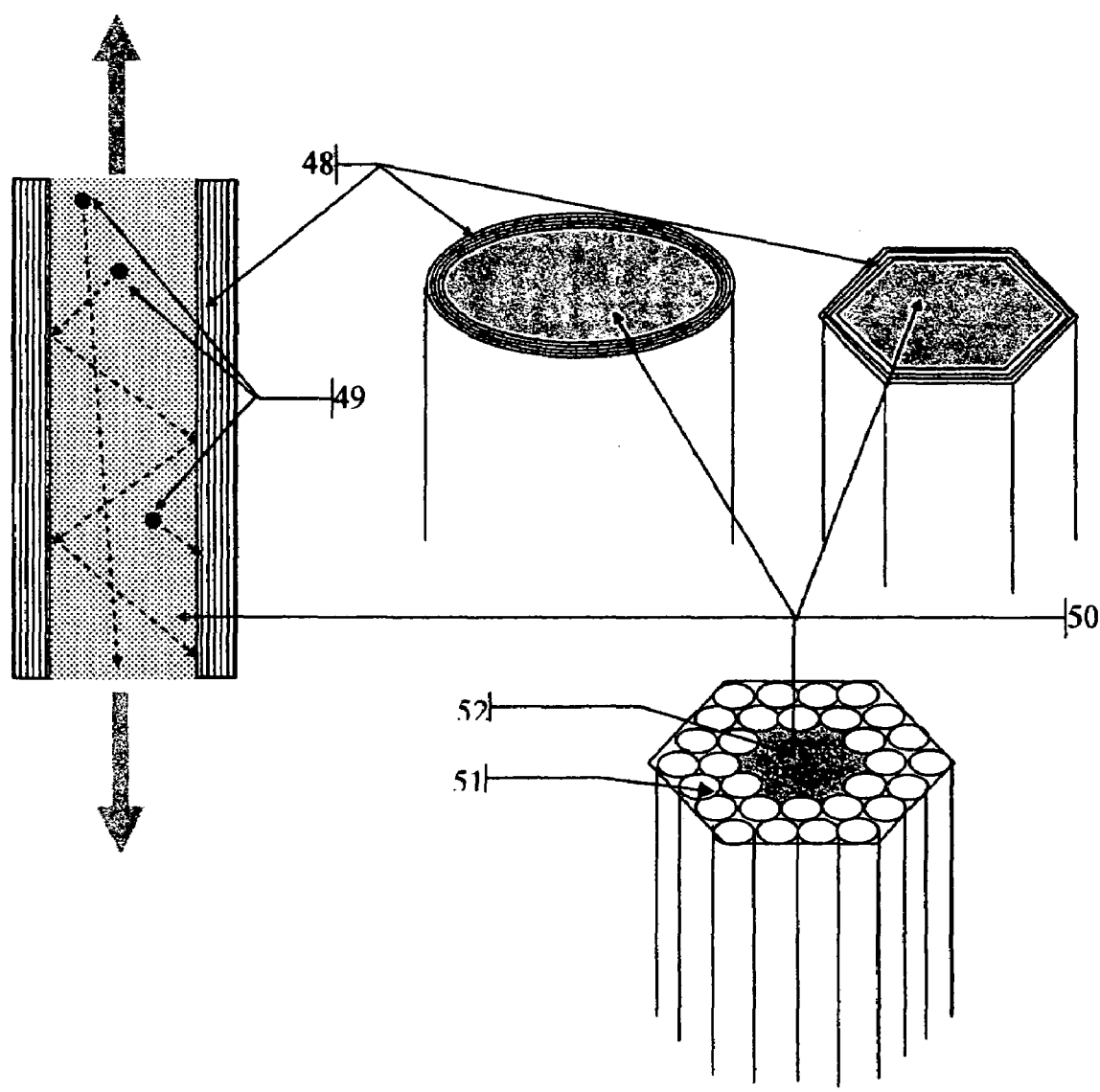
FIG. 10 illustrates several Photonic Crystal fibers whose cores are filled with scintillating material.

FIG. 10 illustrates omni-directional PBCS fibers whose cores 50 are filled with scintillating material. Photons 49 generated within the omnidirectional PBC fiber are reflected from the surrounding multilayer PBC cladding 48, notwithstanding the angle of hitting the wall. The multilayer cladding 48 surrounding the core is composed of alternating materials of high and low refractive indexes or air holes 51 around the core. For example if the core is made of a doped p-terphenyl plastic scintillator having a refractive index of $n_0=1.65$ and a scintillation wavelength $\lambda=425$ nm, the surrounding cladding may be an extremely holey structure or just an aerogel film. If the core is filled with Lanthanum Chloride Bromide $[La(Cl_{0.34}Br_{0.66})_3:CeCl_3]$ having a refractive index of 1.9 the cladding may be several consecutive layers of $SiO_2$ glass and $TiO_2$ having dielectric constants of $n_0=1.45$ and $n_1=2.2$ respectively.

The optimal thicknesses of the low and high index coatings which together are of the order of $\lambda/2 \sim 200$ nm have to be numerically computed in order to maximize the width of the bandgap and the angle of refraction. Scintillations occuring within the omnidirectional PBCS fibers, are reflected by the PBC cladding and propagate to one of the ends of the fiber, with minimal losses.

A structure composed of omnidirectional fibers poses certain advantages as it constricts almost all the emitted scintillation spectrum to propagate within the fiber. In designs where the claddings around the scintillator core are relatively large and high Z, they interrupt the tracks of photo-electrons traversing several cores, and waste part of the energy, thus reducing the energy resolution of the detector and the radiation detecting efficiency.

Figure 11:
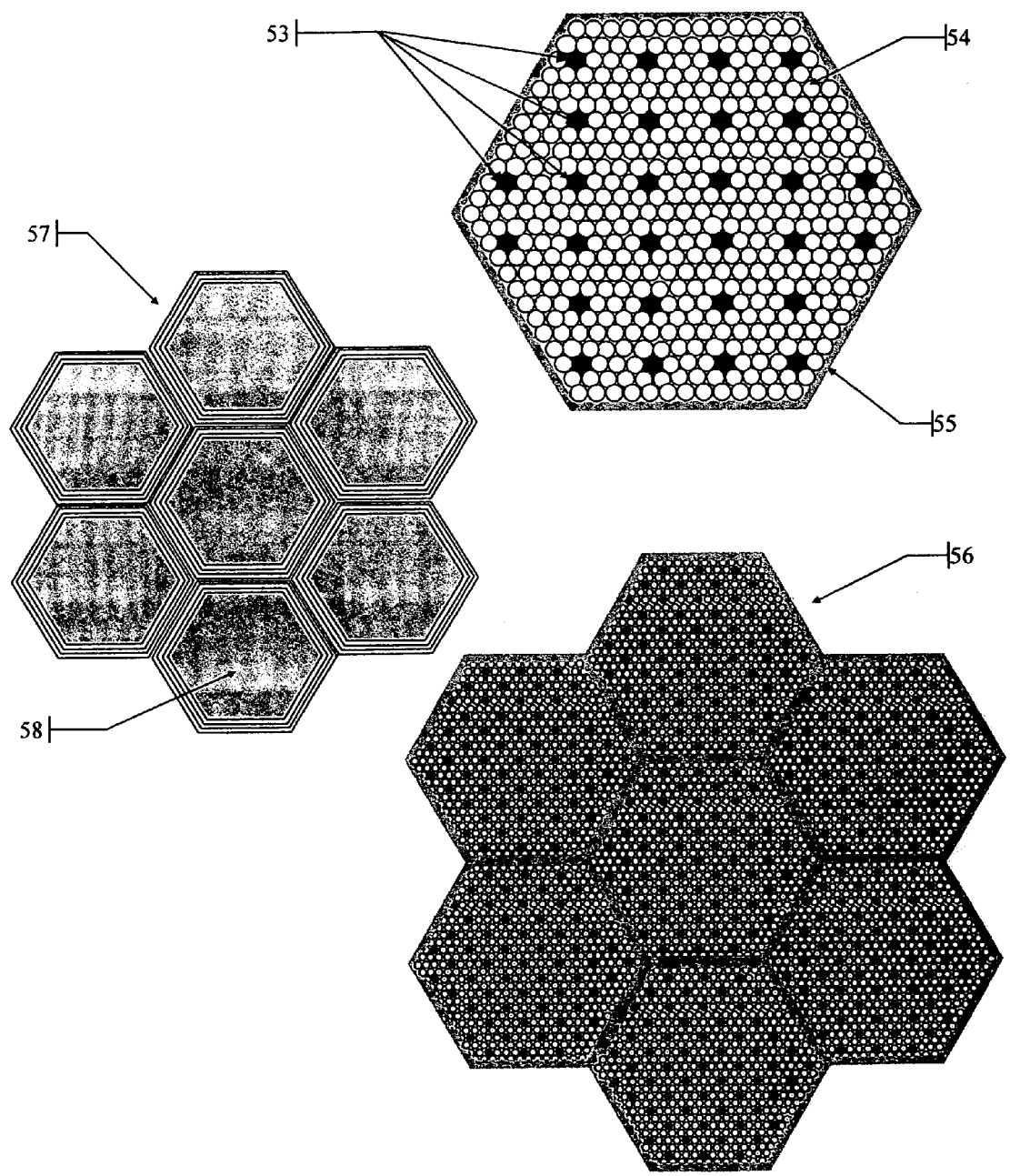
FIG. 11 illustrates several multi-core fibers formed by a multiplicity of close-packed scintillation Photonic Crystal nanofibers.

FIG. 11 ilustrates large omnidirectional PBCS plates composed by fusing together single PBCS fibers. The manufacturing process of a plate composed of omnidirectional PBCS fibers is relatively simple. First a relatively large rod of material having the required relative dimensions between the core and the claddings is prepared, for example by taking a rod of the core plastic scintillator, and coating it with alternating sheets of the coating materials of high and low refractive index, or fusing around the scintillator rod several rings of capillary thin walled glass tubes. After the core and the claddings are fused together, "pulling" the heated material under tension, gradually educes its cross section. When a certain cross section is reached, the elongated rod is cut into pieces which are fused together to form an approximately hexagonal rod with a multiplicity 53, 58 of scintilator cores. The new hexagonal rod is again "pulled" under heat and its cross section further reduced. The elongated hexagonal rod is further cut into pieces and fused together and pulled again under heat forming a larger plate 56 with relatively smaller cores. The process is repeated until the desired dimensions are reached. Large slabs can then be formed by fusing or gluing together smaller multi-fiber rods.

FIG. 12 illustrates the propagation of scintillation light in a loosely packed scintillation fiber surrounded by a thin layer of aerogel of density 1.08 close to that of air. If the refractive index of the scintillator is high enough, a large part of the scintillations 59 hitting the aerogel boundary at an angle larger than the critical angle θ will be fully reflected 61 and will propagate up or down the fiber. The rest of the light will exit the scintillation fiber and will partly enter adjacent fibers and partly will be scattered by them.

Figure 13:
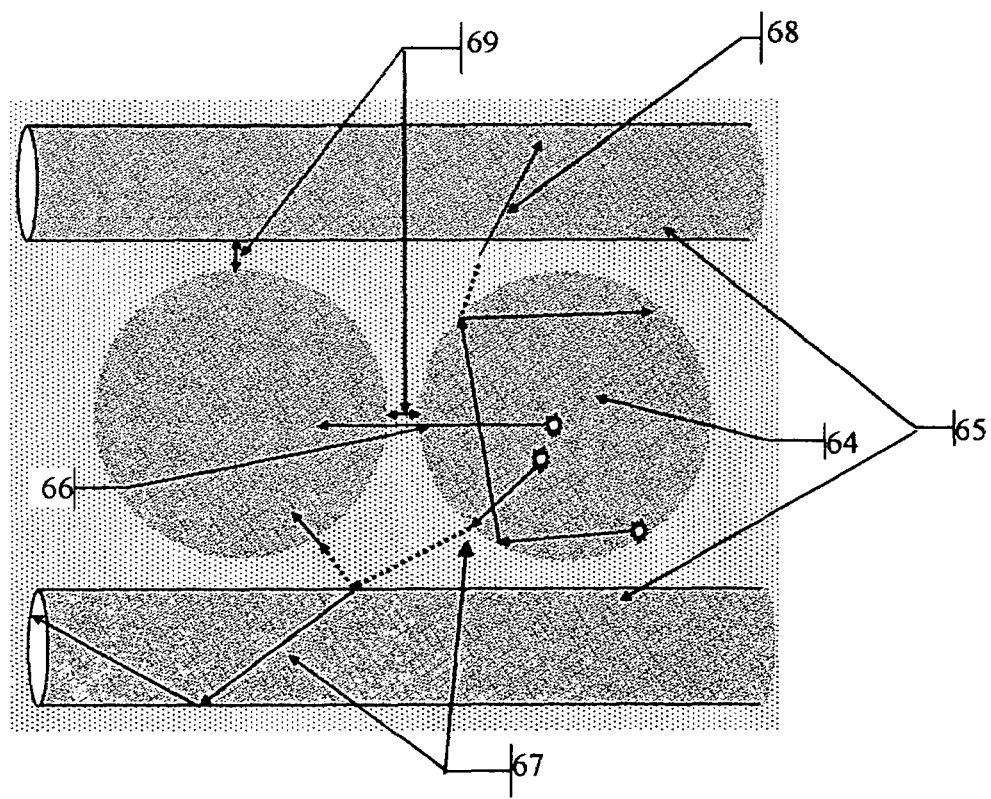
FIGS. 13 and 14 illustrate the propagation of the scintillations within an assembly of criss-crossed layers of 2D scintillation fibers.

FIG. 13 illustrates the propagation of the scintillation light not guided by critical angle reflection, in a loosely packed wood-pile array, 64, 65 where both the scintillation fibers and the scintillation fiber layers are separated by a thin layer of aerogel 69 of a thickness of at least one wavelength of the scintillation, in order to prevent the evanescent wave to cross over from one fiber to another and destroy the position finding scheme described below in conjunction with FIGS. 15 and 16. The fibers and the fiber layers are kept separate by mechanical means. The scintillation photons hitting the fiber/aerogel boundary at an angle smaller than the critical angle, will be partially reflected and refracted and will eventually enter the neighboring scintillation fibers, whether parallel 66 or perpendicular 65 to the original fiber. Some of the photons entering the perpendicular fibers will propagate along the fiber guided by critical angle reflection 67 and some will exit the adjacent fibers 68 and will be further scattered by more distant fibers.

Figure 14:
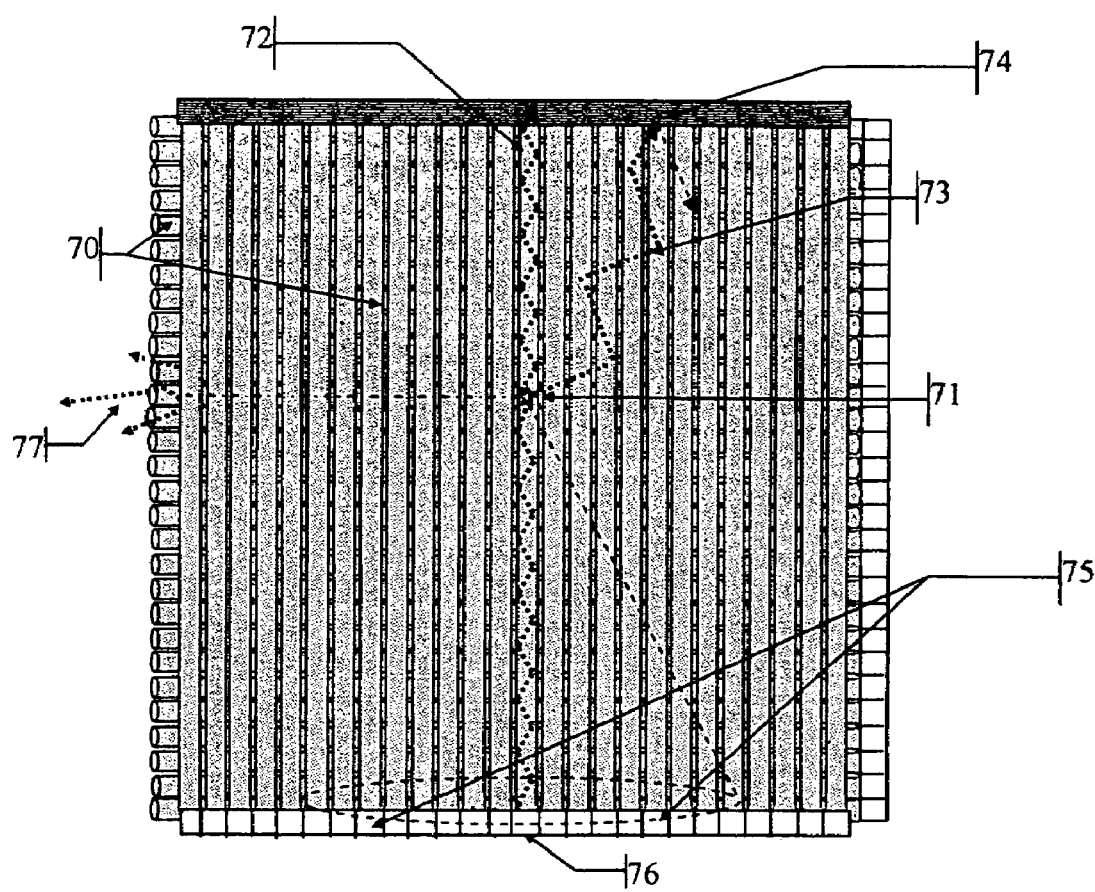

FIG. 14 illustrates the process, where a large part of the scintillation photons 71 propagate through the scintillation fiber guided by critical angle reflection and reach both the top or bottom ends; if one of the ends is coated with an efficient mirror 74, the reflected photons travel to the other end and are detected there by a photo-electric sensor 76. As mentioned above, the photons that hit the scintillation fiber at an angle smaller than the critical angle will be scattered by the neigboring fibers and will exit the scintillation array through both the parallel 75 and perpendicular 77 scintillation fibers surrounding the scintillation spot 71.

Figure 15:
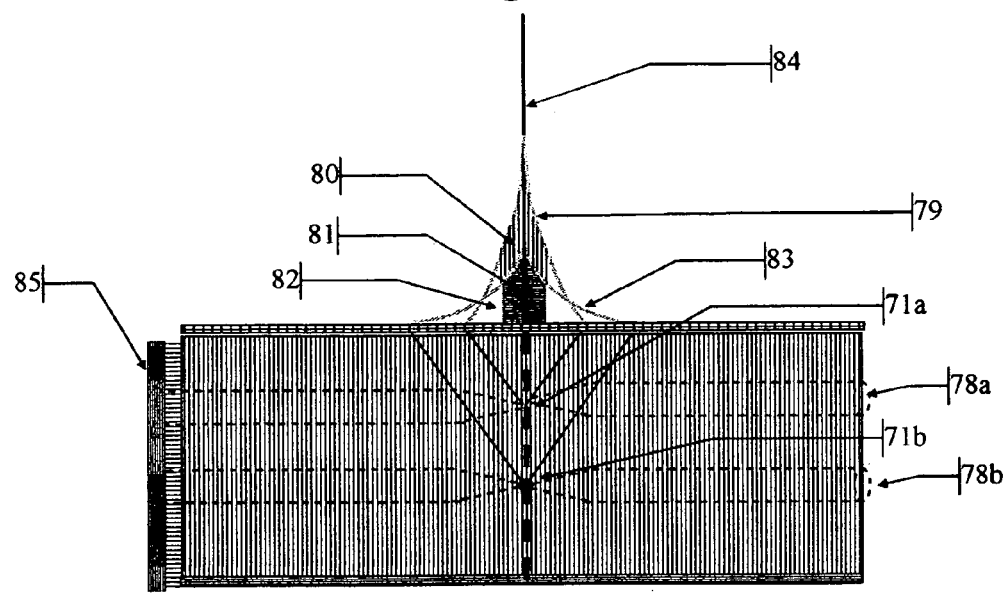
FIGS. 15 and 16 illustrate methods for finding the coordinates of a scintillation event in a structure composed of a "woodpile" of 2D layers of fibers stacked one orthogonal to the other.

FIG. 15 illustrates the distribution among the neighboring fibers of the scintillation light engendered within a scintilation fiber, that traverses the fiber/air or fiber/aerogel boundary at a subcritical angle, is scattered by the adjacent fibers and reaches one of the ends of the array where photo sensors detect the respective intensities. The photons reaching the other end if reflected back, will contribute to the intensity distribution, although it may not enhance much the asymety of the distribution, due to the larger distances forth and back and consequently the increased amount of scattering. The photons that propagate through the neighboring fibers to the end, are spread over with an intensity distribution decreasing from the center to the periphery. This distribution is narrower 79 when the scintillation occurs nearer the end of the fiber 71a, than the distribution 83 which is wider and shallower when the scintillation occurs farther away 71b from the end of the fiber. Thus the position of the scintillation along the fiber can be determined by the "shape" of the "penumbra", the intensity distribution of the photons exiting the adjacent fibers. The exact "shape" and "relative intensity" of the distribution as a function of distance from the end (d) of the fiber is dependent on many parameters. These parameters include the refraction index contrast between the fiber and the surrounding material that determine the portion of the scintillations leaving the fiber and their angles of exit, the distances of the adjacent fibers and their distribution, the length of the fibers that determine the distance that the reflected photons have to travel on their way back to the other end of the array and the amount of scattering they experience, and the nature of the side walls of the array that may reflect, scatter or absorb some of the photons. All these factors dictate that the "shape" and "relative intensity" of the distribution of photons exiting the bottom of the array have to be empirically determined for each specific array of fibers.

On a first approximation, as the proportion of photons propagating by critical angle reflection and reaching the photo sensor is independent of the position along the fiber, the ratio between such number of photons and the aggregate number of photons exiting through the nearby (2-3) rings of surrounding fibers, is a good measure of the distance. Similarly a ratio of the photons exiting through the first "$n_0$" rings 80 or 81 and those exiting from the rest of the surrounding rings (N–$n_0$) 82 is also a good measure of the distance (d) of the scintillation from the end of the fiber; the number of the "$n_0$" rings has to be determined empirically so as to maximize the sensitivity of the measurement ($\partial d/\partial n_0$). In case the scintillator fiber array is structured as a wood-pile where each layer of vertical fibers has before and after it, a layer of lateral fibers, and vice versa, the neighboring fibers also include fibers running orthogonally to the direction of each fiber. Thus some of the subcritical angle photons exiting the original fiber, will enter these orthogonal fibers and part of them will propagate by critical angle reflection to both ends of such fibers 78a, 78b. Although the proportion of such laterally propagating photons is relatively small, detecting them and finding their center of gravity, will give the position of the scintillation event on the original scintillation fiber.

Figure 16:
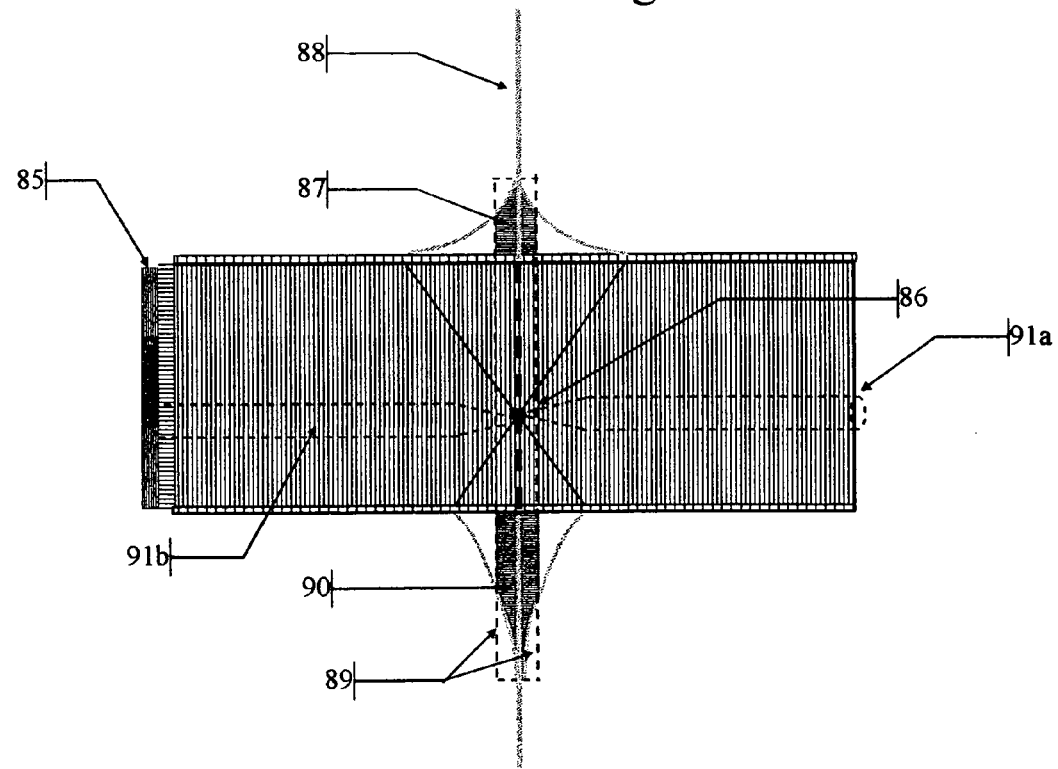

FIG. 16 illustrates another mode of determining the position 86 of the scintillation along the fiber, by measuring the distribution of the photons that exit the fiber at subcritical angles and after multiple scatterings, exit the wood-pile fiber array from both ends of the lateral and vertical fiber layers. As explained above in connection with FIG. 15, the "shape" and "relative intensity" of the distribution of photons exiting the fibers surrounding the fiber where the scintillation occurred, from each end is a function of distance of the scintillation position. from the respective end. Thus, as explained above, after calibrating empirically the distance as a function of the "shape" and "relative intensity" of the distribution of photons, the distance of the scintillation from each of the ends may be determined independently. As explained above, the ratio of the photons exiting an empirically determined number ($n_0$) of surrounding rings 89 of fibers, from the top 87 and the bottom 90 is a function of the location of the scintillation event along the scintilation fiber. In this geometry too, the center of gravity of the laterally propagating photons 91a, gives an additional measure of the position of the scintillation event on the original scintillation fiber.

Figure 17:
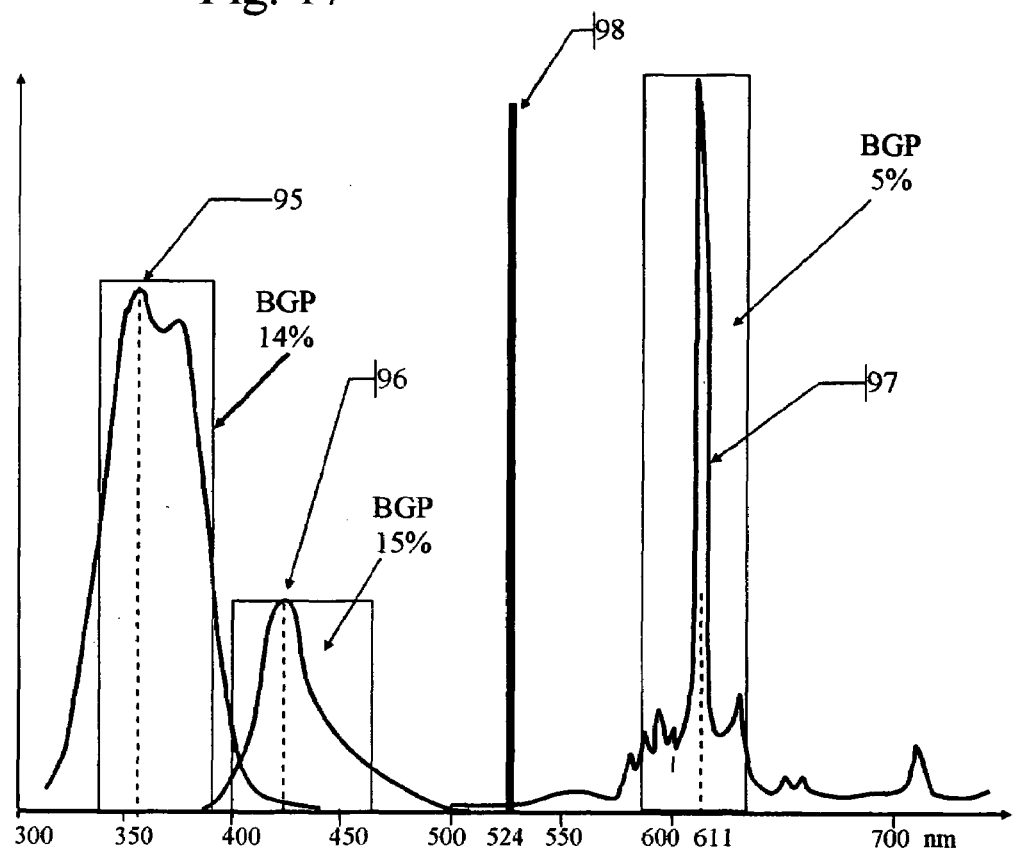
FIG. 17 shows the spectra of several exemplary scintillators suitable for PBCl structures, whose spectra illustrates the required bandgap bandwidths.

FIG. 17 shows the spectra of several exemplary scintilators that could be used for building Compton Cameras able to determine the direction of the incoming gamma rays. Cerium doped Lanthanum Chloride Bromide [La$(Cl_{0.34}Br_{0.66})_3$:CeCl$_3$] 95 has the highest light yield of 82 photons/kev and is commercially available, although not in fiber form. The plastic scintillator doped p-terphenyl 96 has allegedly a high light yield of 27 photons/keV and is also commercially available, also not in fiber form. Manufacturing suitable fibers of both materials is explained below. However both scintillators have wide spectra and a need for a lattice with a bandgap larger than 15%, which is difficult to realize. On the other Europium doped Yttrium Gadolinium Oxide ($Y_{0.46}Gd_{1.54}O_{0.04}$:Eu$^3$) 97, has a high light output of 50 photons/keV and a narrow spectrum around 611 keV that may be covered with a narrow bandgap of the order of 5%; however its decay time is very high and cannot be used but in very low counting rate applications; moreover it is not commercially available at this stage.

ZnSe(Te) crystals are used in relatively thin layers, as their self absorption is high. Their light output is very much dependent on the size of the crystal. However in PBCS structures, as the cross section of a filament is less than 1μ$^2$, the only absorption of interest is the one along its length; thus filaments of up to 10 mm will exhibit little absorption. Their light yield is expected to reach and even exceed the 80 photons/keV when self absorption is minimal. Their high refractive index of 2.6 makes them suitable for large bandgaps; the small critical angle when surrounded by air or aerogel (22.5°), enables a large proportion of the scintillations (62%) to be conducted by TIR. Its long decay time however limits its use to low counting rate applications.

Table 2 gives the main specifications of scintillators that could be used in PBCS cameras.

TABLE 2

| Scintillator | Peak λ nm | Decay time nsec | density g/cm$^3$ | Light yield ph/kev | Melting/ sintering temp. ° C. | refractive index (n = ε$^{1/2}$) |
|---|---|---|---|---|---|---|
| Pure Cesium Iodide CsI | 310 | 300 | 4.51 | 17 | 621 | 1.8-1.9 |
| Bismuth Germanate Bi$_4$Ge$_3$O$_{12}$ | 480 | 300 | 7.13 | 8.5 | 1,050 | 2.15 |
| ZnS:Ag | 450 | 200 | 5.27 | | 1.525 | 2.6 |
| Lutetium Iodide (LuI$_3$:Ce) | 474 | 23-31 | 5.6 | 50 | 1,050 | 1.9 |
| Lutetium Oxyorthosilicate Lu$_2$SiO$_5$:Ce$^{3+}$(LSO) | 420 | 40 | 7.4 | 30 | 2,200 | 1.82 |
| Lutetium Yttrium orthosilicate (LYSO) (LU$_{2(1-x)}$Y$_{2X}$)SiO$_5$:Ce | | 40 | 6.5 | 32 | | 1.9 |
| Lutetium Aluminate, (LuAlO$_3$):Ce | 365 | 17 | 8.34 | 17 | | 1.94 |
| Lanthanum Chloride Bromide La(Cl$_{0.34}$Br$_{0.66}$)$_3$:CeCl$_3$ | 355 | 25 | 5.3 | 82 | 950 | 1.9 |
| Lanthanum Bromide LaBr$_3$:Ce | 380 | 35 | 5.3 | 63 | 950 | 1.9 |
| Lanthanum Chloride La Cl$_3$:Ce | 350 | 25 | 3.8 | 46 | 950 | 1.9 |
| Yttrium Gadolinium Oxide Y$_{0.46}$Gd$_{1.54}$O$_{0.04}$:Eu$^3$ | 611 | ? | 7.33 | 50 | 1400 | |
| Yttrium Gadolinium Oxide..Y$_2$Gd$_2$O$_3$:Eu | 610 | ? | 5.95 | 40 | 1400 | |
| Yttrium Aluminum Perovskite YAlO$_3$:Ce$^+$YAP | 370 | 27 | 5.55 | 18 | 1,875 | 1.95 |
| Gadolinium Orthosilicate Gd$_2$SiO$_5$:Ce | | 40 | | 12 | 2,050 | |
| Calcium Fluoride CF$_2$:Eu | 435 | 600 | 3.18 | 23 | 1,360 | 1.44 |
| Doped P-terphenyl C$_{18}$H$_{14}$ | 425 | 3.7 | 1.23 | 27 | 214 | 1.65 |

TABLE 2-continued

| Scintillator | Peak λ nm | Decay time nsec | density g/cm³ | Light yield ph/kev | Melting/ sintering temp. ° C. | refractive index (n = ε^(1/2)) |
|---|---|---|---|---|---|---|
| ZnSe(Te) | 610-640 | 3-30 μs | 5.42 | 30-80 | 1790 | 2.6 |
| Glass scintillator SiO$_2$:Ce$^{3+}$ | 465 | 50 | | 25 | 1,400 | 1.46 |
| P-47 powder-Y$_2$SiO$_5$:Ce$^{+3}$ | | | | | | |
| (C$_3$H$_3$NH$_3$)PbBr | | 0.16 | | | | |
| (C$_n$H$_{2n+1}$NH$_3$)$_2$PbX$_4$), (C$_6$H$_{13}$NH$_3$)$_2$PbI$_4$ | 524 | 0.045 | 3.3 | High ?? | | |

A recently discovered perovskite-type organic/inorganic hybrid scintillator (C$_6$H$_{13}$NH$_3$)$_2$PbI$_4$ which is a combination of an organic (C$_6$H$_{13}$NH$_3$) cation and an inorganic PbI$_4$ anion which is a semiconductor, has an extremely short lifetime of 45 psec and a very narrow single emission line at 524 nm, which could be suitable for covering it with a narrow bandgap. Having a medium density of 3.3 g/cm³ and an average Z of 41 it looks as suitable for high energy Compton cameras and as a PBCS gamma detector for positron emission tomography (PET).

Figure 18:
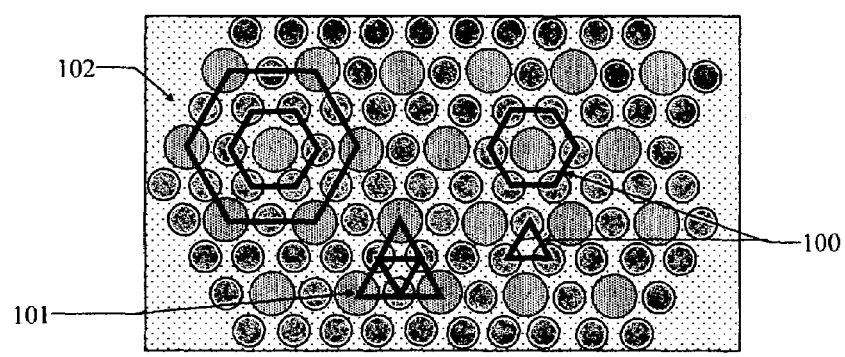
FIG. 18 illustrates two intertwined PBCS lattices each with a different Bandgap.

FIG. 18 illustrates two methods of structuring two bandgaps at different wavelengths in a PBCS Scintillator Crystal, which may be adjacent and thus together form a wider hybrid-bandgap. One such structure consists in one hexagonal/triangular periodic lattice nested within a second periodic lattice which has a larger period. The dielectric constant of the matrix around the first lattice is a mixture of the common matrix 102 and the dielectric constant of the "pillars" of the second lattice and varies along the propagation route. The dielectric constant of the matrix around the second lattice is a mixture of the common matrix 102 and the dielectric constant of the "pillars" of the first lattice and also varies depending on the propagation route taken by the scintillation photons. Such a structure is complex to analyse, but as the period of one lattice is larger than the other one, it will show two bandgaps.

Another way to structure two adjacent bandgaps is to structure the Photonic Bandgap Scintillation Crystal out of adjacent "islands" 103 and 104, where each "island" having different sized columns (or holes) and different periods, will have a Bandgap for a different set of wavelengths. The physical dimensions of the columns (or holes) and the period of the lattice may be tuned so that the bandgaps will be adjacent or even will overlap. A lightwave traversing one "island" that has a bandgap outside its wavelength, will be reflected back by another section that prohibits it. The size and geometry of the "islands" has to be optimized so that a lightwave will always have to cross at least two different "islands", independently of its angle of propagation. This solution basically enlarges the diameter of the section through which the photons exit the crystal, to two "islands". If each "island" is 12 "periods" for example then the sideways propagating photon will be stopped at most within 1.5 islands, or 18 "periods". For a period of a$_1$=200 nm a$_2$=300 nm, it means that the photon cannot propagate laterally beyond ~5μ before being stopped. This may be acceptable for detecting the photoelectric event that follows the Compton scattering event where 5μ accuracy of the position of the scattered gamma's interaction with the PBCS crystal is more than acceptable.

This strategy while somewhat enlarging the cross section of the stream of photons that are forced to propagate orthogonally to the 2D plane, enables to channel more photons into the stream, towards the photo-detector.

Figure 20:
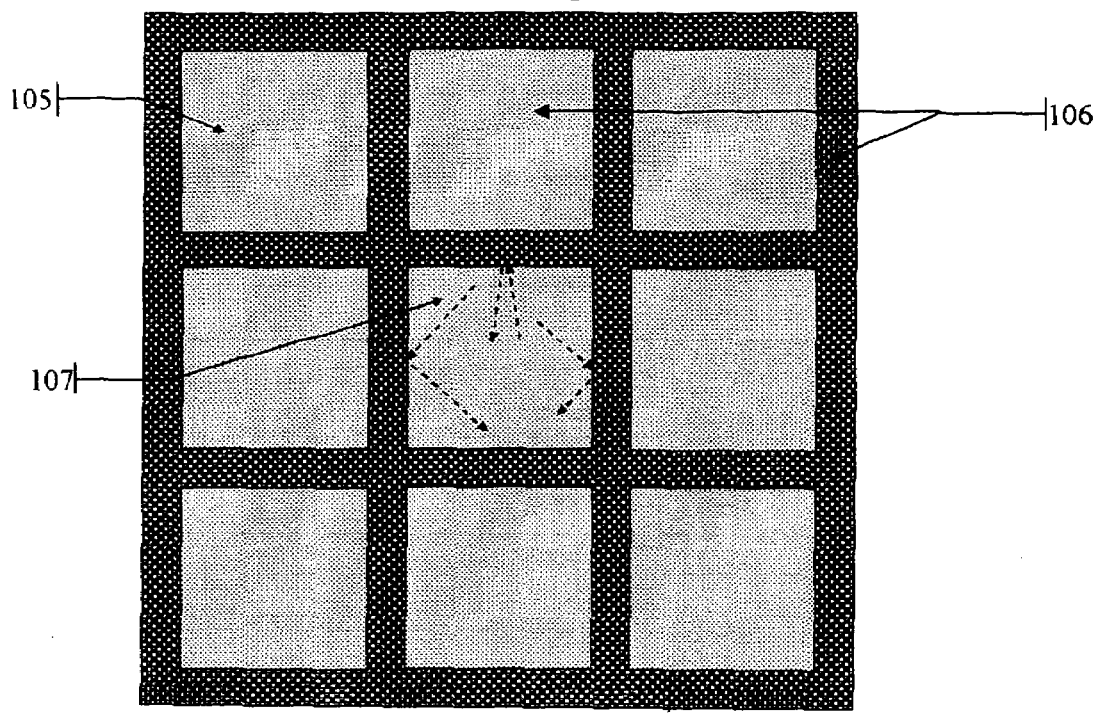
FIG. 20 illustrates two scintillator structures composed of large pixels surrounded by PBC strips, inhibiting the propagation of scintillation light from one sub-area to another.
Figure 20:
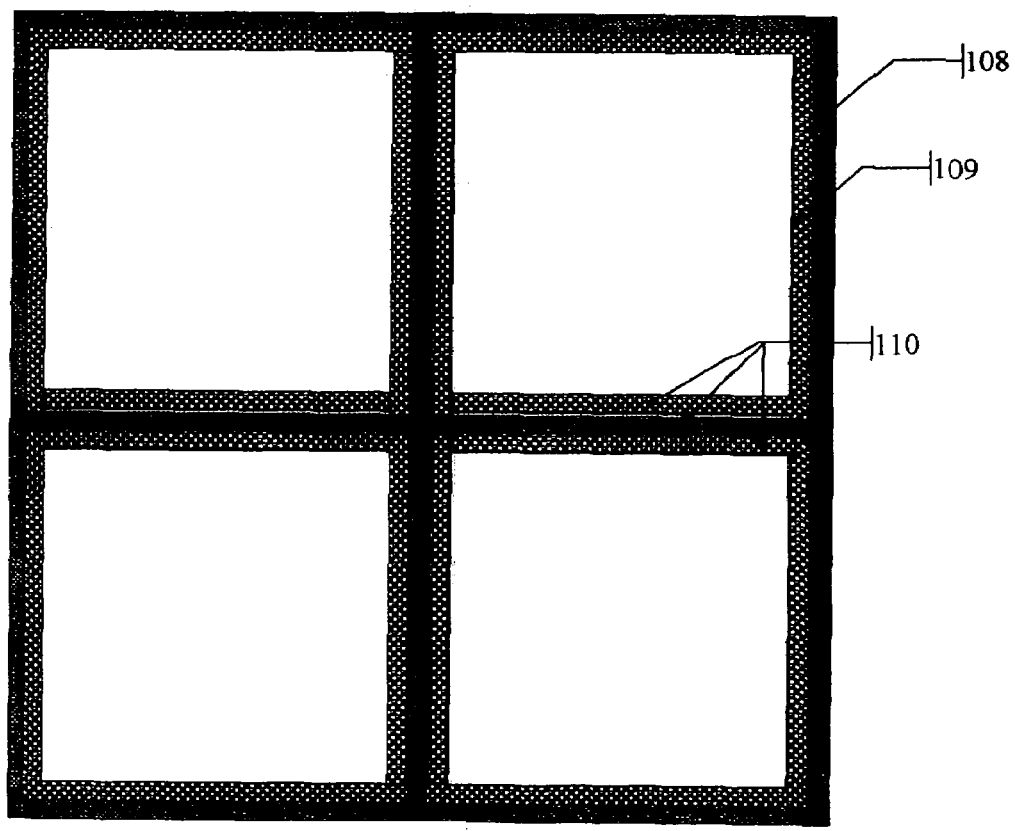

FIG. 20 illustrates the use of PBC virtual walls 106, 107, 111 with a single or two adjacent bandgaps surrounding relatively large pixels of scintillator 105, 110 of the order of several hundreds of microns to millimeters, to constrict the emitted scintillations within the pixel. Such PBC virtual walls come to replace thin metallic walls coated with TiO$_2$ for reflecting back the light within a scintilator pixel. A single bandgap virtual wall may be as thin as 4 layers or for a scintillator with an emission spectrum around 500 nm, approximately 1μ thick. A virtual wall around the pixels with a larger bandgap would require 3 strips, each four layers deep, and would be approximately 3μ thick.

Figure 21:
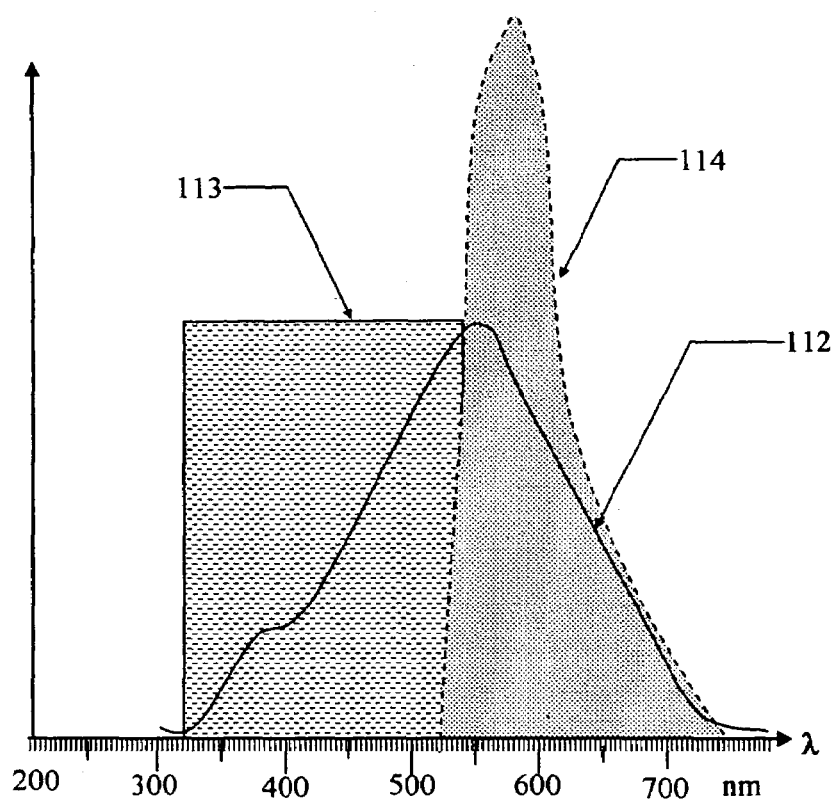
FIGS. 21 and 22 illustrate the narrowing of the spectrum of a scintillator in a 3D PBC lattice.

FIG. 21 illustrates a way to reduce the width of the emission spectrum of a scintillator, by partially inhibiting the emission of the scintillator at certain parts of the spectrum. Inhibiting emission at certain wavelengths will enhance population and subsequent decay through the non-inhibited energy levels, thus changing the emission spectrum and lifetime of the scintillator. FIG. 21 illustrates the original CsI(Tl) spectrum 112 spreading from 350 nm to 750 nm. If the CsI(Tl) scintillator is structured as a 3D PBCS with a bandgap covering the higher energy region of the spectrum, say from 350 to 525 nm, the respective excited levels forbidden to directly decay, will first decay to intermediate energy levels and from there to the ground states. Consequently the spectrum of the CsI(Tl) will spread from 525 nm to 750 nm with enhanced intensity at these wavelengths 114. A Photonic Bandgap Crystal Scintillator that exhibits a full bandgap in 3 dimensions may be used to "lock" the spontaneous emission of excited levels within the lattice and let them decay only through "allowed" states, through a momentarily "allowed" path. Such a momentarily "allowed" route may be formed, if the refractive index of the crystal, or parts of it, are "momentarily" changed either electrically or optically.

Figure 22:
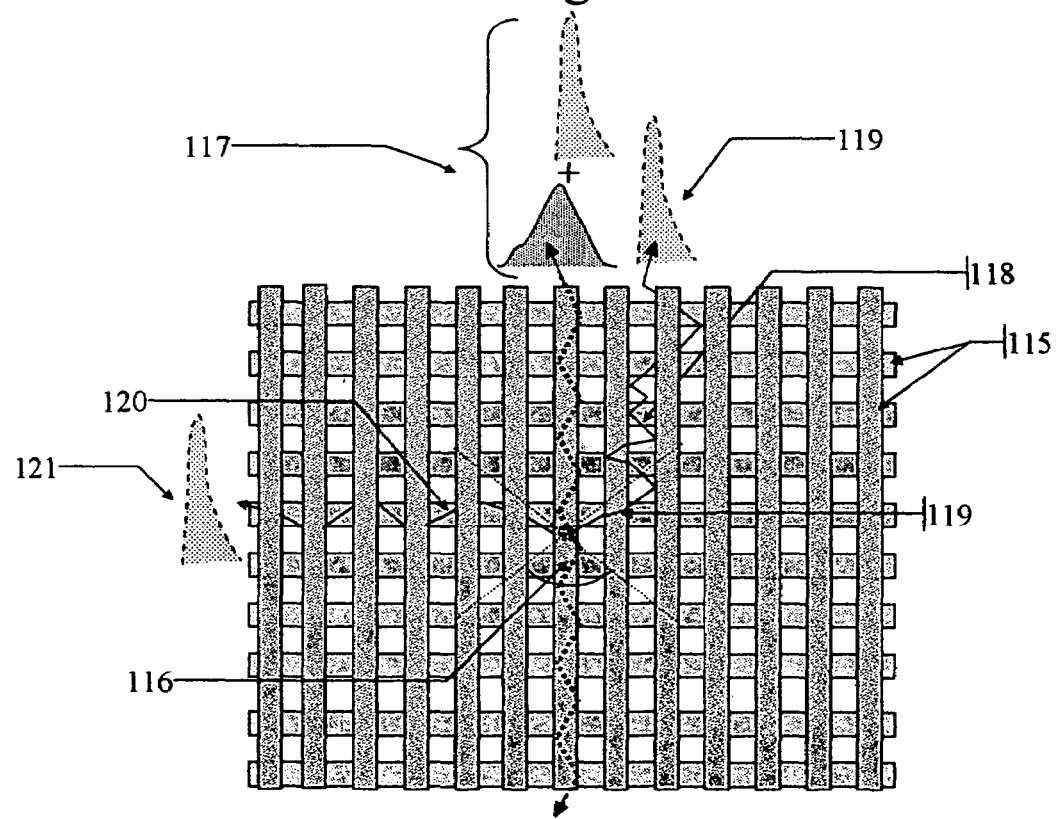

FIG. 22 illustrates a wood-pile criss-cross of aerogel separated scintillator fiber layers 115 that it is structured to have a bandgap in the higher energy region of the scintillation spectrum. Scintillation photons generated inside one of the fibers and within the cone formed by critical angle reflection 116, will propagate along the fiber, without being affected by the bandgap. However only photons outside the bandgap may propagate across the Photonic Crystal structure. These lower energy photons will propagate through the original scintillator crystal 117 as well as the neighboring fibers and interstices 119, 120 after being scattered 118, as explained in connection with FIGS. 15 and 16. Thus for a single ionization event occurring within a scintillator fiber, the spectra of the photons coming out of the fiber where the scintillations occurred and those coming from the adjacent fibers are different. These differences may be utilized to confirm the precise position of the ionization event in the PBCS stucture.

Figure 23:
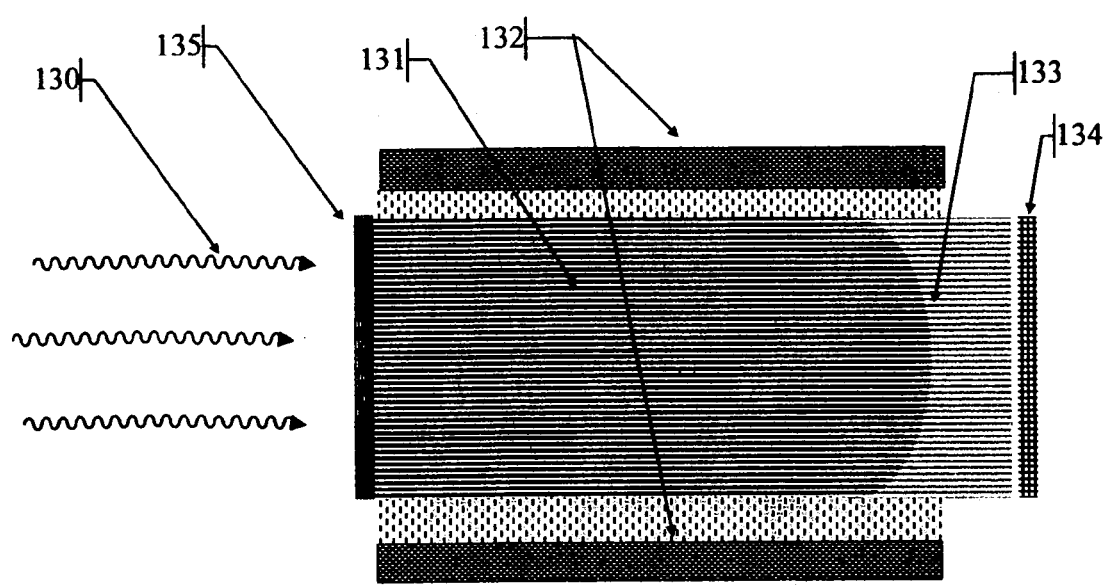
FIG. 23 illustrates a 3D PBCS lattice where the scintillations are amplified by stimulated emission.

FIG. 23 illustrates a method to internally amplify the number of photons produced in a PBCS following an ionization event using a stimulated emission. Population inversion of excited levels in scintillators activated with rare-earth dopants such as Ce and Eu may be achieved by irradiating them with electromagnetic waves (light) of the appropriate energy. Thus in Cerium activated Glass, Lanthanum Chloride Bromide or Lutetium Iodide scintillators, the Cerium energy levels leading to scintillation, may be stimulated by illuminating them with a UV source 132, such as a AlGaN UV diode laser emitting at 340 nm. Thus an original photon created when a scintillation level excited by an ionizaton event is de-excited, causes when traveling along the fiber 131 to the emission of multiple photons, effectively amplifying the scintillation pulse. The amplification is obviously proportional to the number of rare earth dopants encountered during the propagation; thus a long fiber will result in higher amplification. In general this poses a problem as scintillations close to the exit end will experience less amplification than those far away; the resulting dispersion in pulse height would make the energy determination impossible. However in the fiber structures where one of the ends of the fibers are coated with a fully reflecting mirror 135, the photons generated in a scintillation event will always travel an average distance equal to twice the length of the fibers, irrespective of their position on the fiber. Thus the total amplification will be constant. If instead of reflecting back the photons from one of the ends, both ends have photo sensors, as illustrated in FIG. 16, then the amplified signals have to be added for determining the pulse height of each event. A second problem that arises when illuminating the PBCS fiber array with a UV diode laser bar 133 is that the illumination may not be uniform and the same for all the fibers. This problem may be remedied by illuminating the fiber structure uniformly by surrounding it with diode laser bars and compensating for the reduced UV light reaching the internal fibers, by lengthening them appropriately 133. The photo sensors 134 are in this case, connected to the respective scintillation fibers by variable length, non-scintillating fibers 133. A PBCS fiber array is particularly suitable for such amplification as there is no need to coat the individual fibers for preserving propagation along the fiber.

Figure 24:
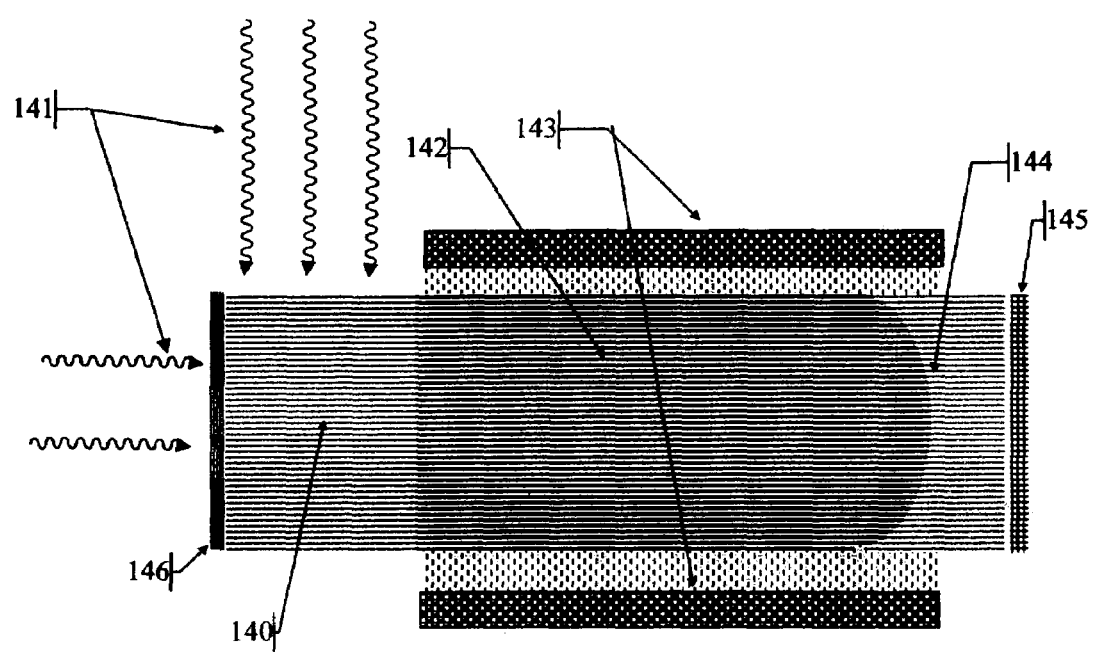
FIG. 24 illustrates a 3D PBCS lattice where the scintillations are amplified in a follow-up stage of properly doped fibers juxtaposed to the scintillation fibers.

FIG. 24 illustrates a different scintillation amplification scheme, where the fiber structure includes scintillation fibers 140 seamlessly connected to non scintillating fibers 142 which are doped with the same rare-earth dopant as the scintillating fibers. In this method all scintillation photons independently of their location along the scintillation fiber get the same amplification per unit length, in the second non scintillating fiber section. In this method too, the fiber structure is uniformly illuminated by surrounding it with diode laser bars and compensating for the reduced illumination reaching the internal fibers, by lengthening them appropriately 144. One of the advantages of this scheme is that it allows the non-scintillating fibers to be non-linear, for example from chalcogenic glass, enabling to generate the sum of the impinging radiation. Thus diode lasers in the 600 nm region that are abundant and low cost, may generate the required 300 nm UV photons for stimulated emission. This geometry also facilitates the aligning of the fiber array either in line or perpendicular 141 to the radiation to be detected.

Figure 25:
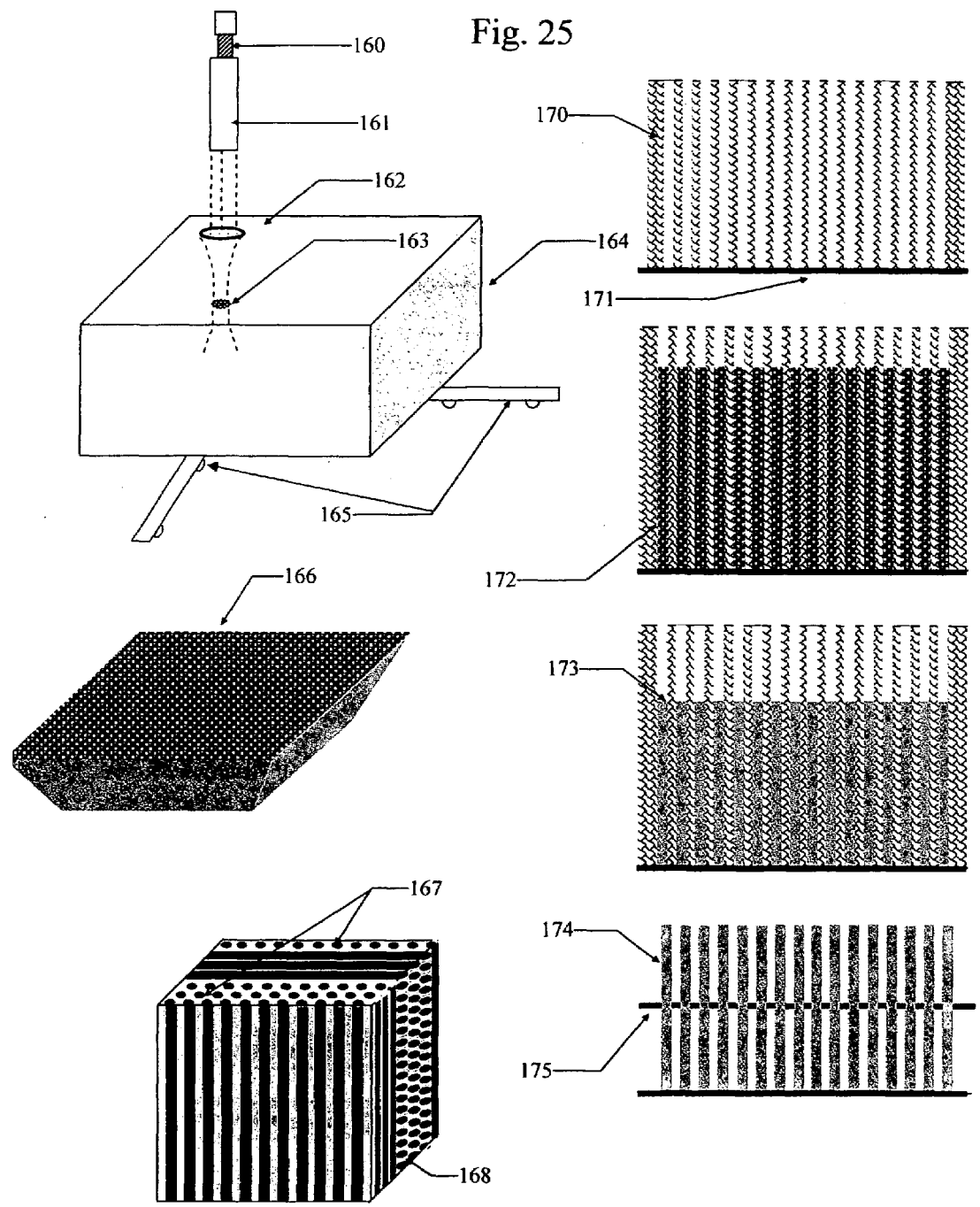
FIG. 25 illustrates a method of manufacturing a Photonic BandGap Crystal by drilling sub-micron sized holes in a matrix with a high intensity femtosecond laser, that ablates the material
Figure 26:
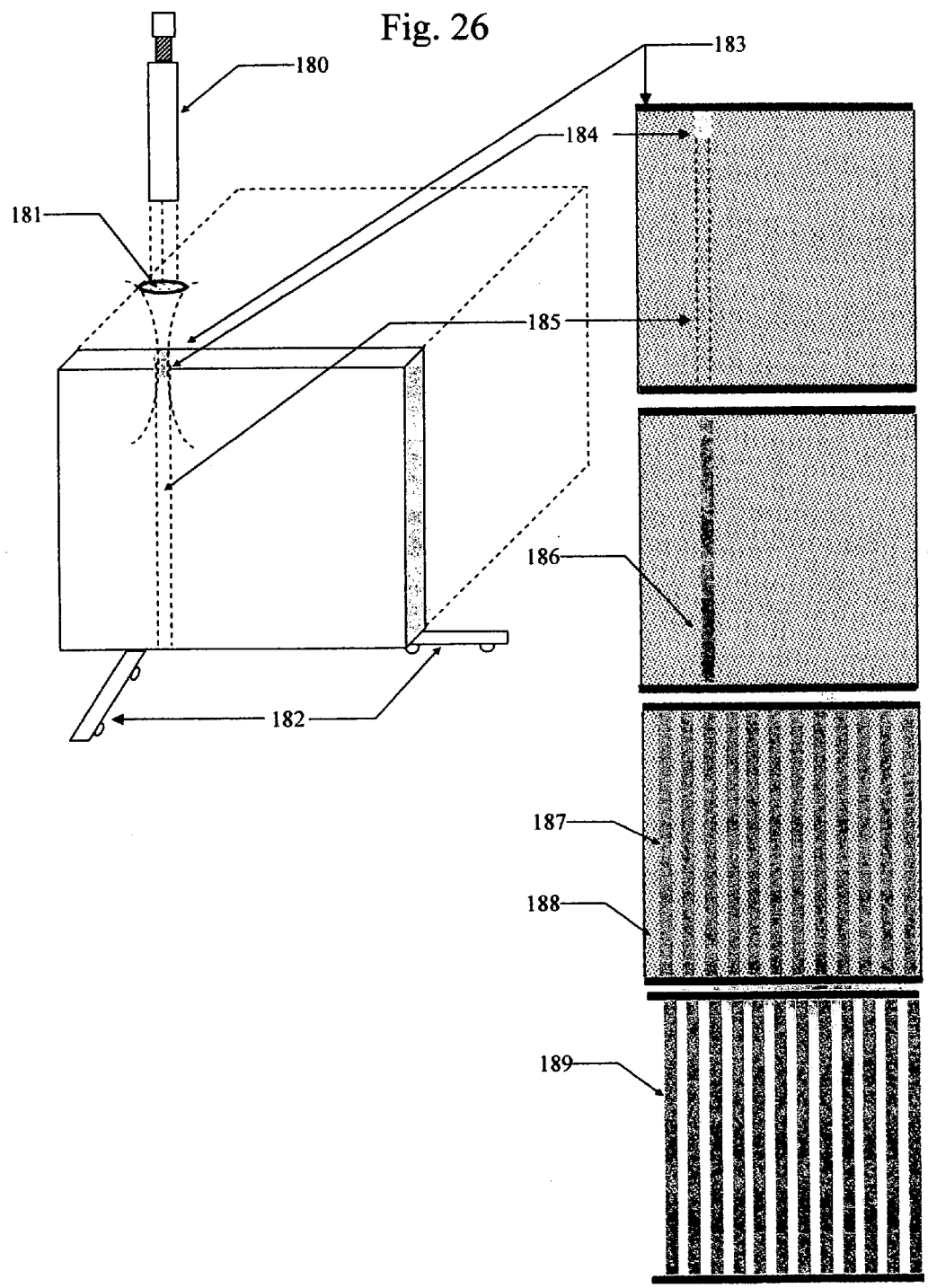
FIG. 26 illustrates a 2D Photonic Bandgap Crystal of long pillars manufactured by polymerizing a tubular section of a photopolymer solution with a UV laser beam followed by extraction of the non-polymerized solution between the polymerized pillars with an appropriate solvent.
Figure 27:
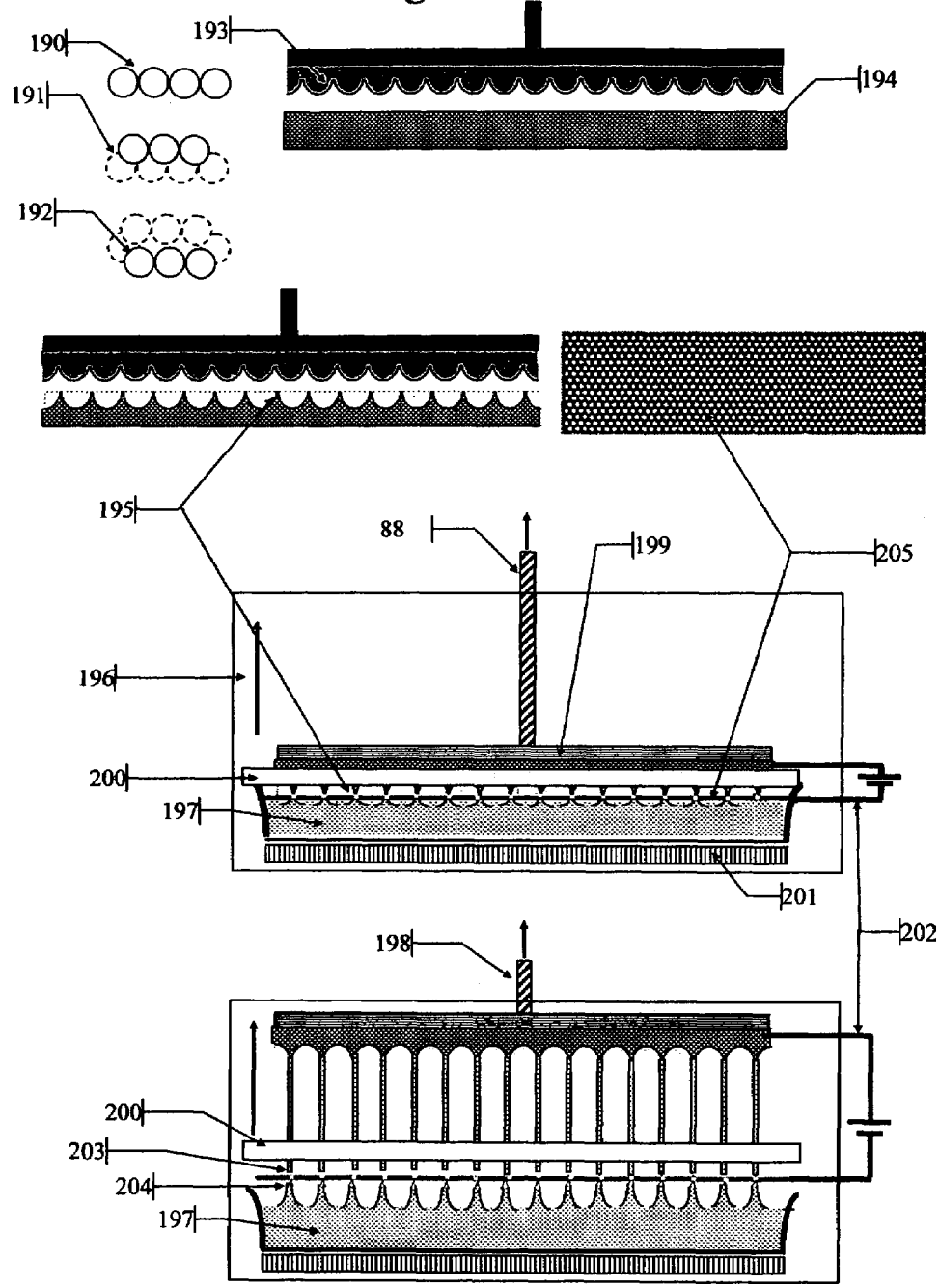
FIG. 27 illustrates the preparation of an array of ultra-sharp needles and the pulling of arrays of columnar filaments out of superheated liquefied material using such an array of needles.
Figure 28:
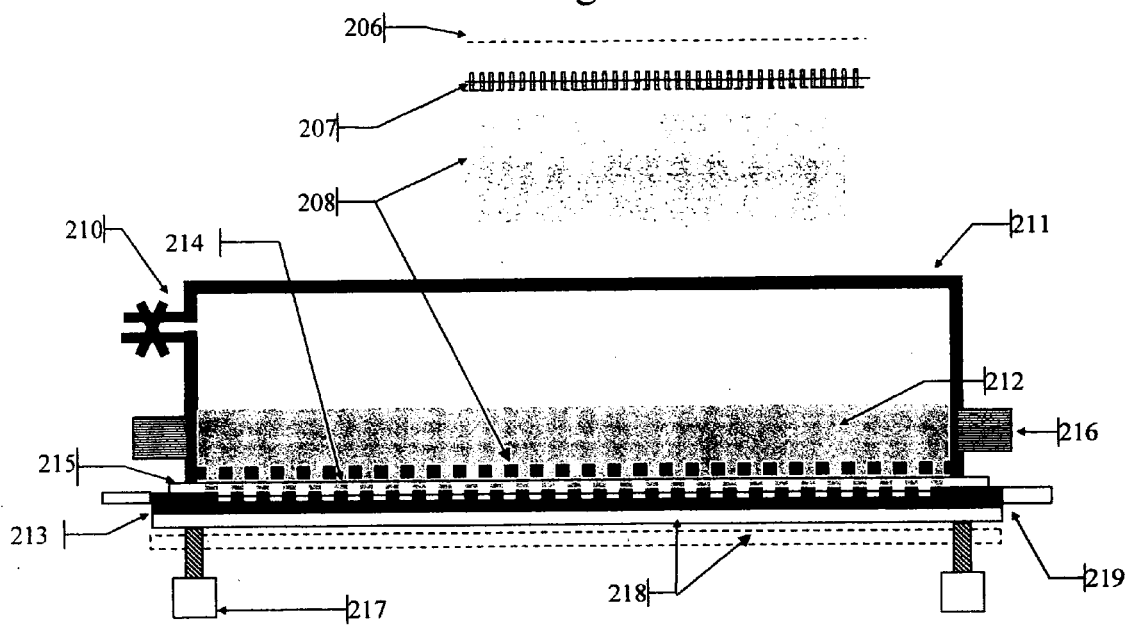
FIG. 28 illustrates the process of forming a 2D array of nano-filaments by pressing a light curable solution through the sub-micron holes of a template and subjecting the filaments seeping through the sub-micron holes to an intense light that cures them on the fly.
Figure 29:
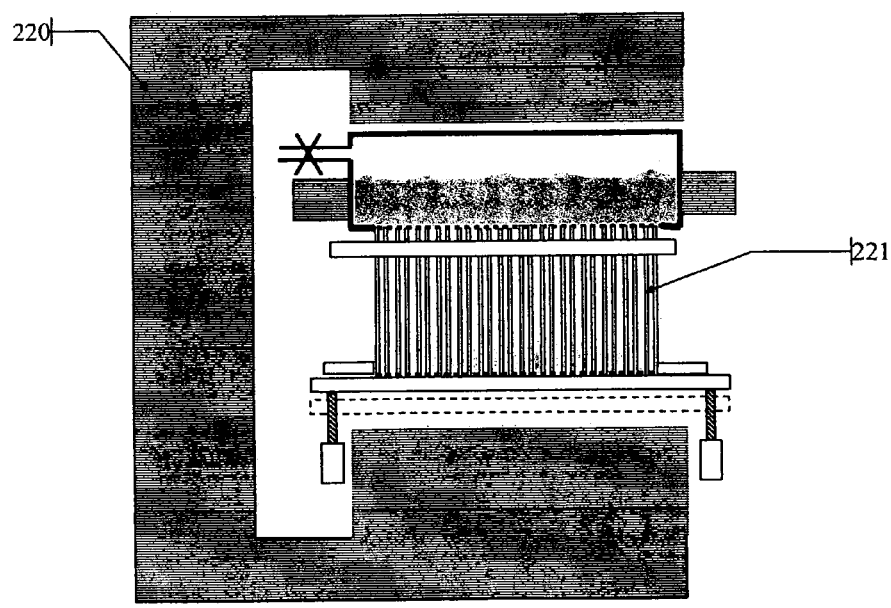
FIG. 29 illustrates the process of forming a 2D array of nano-filaments by pressing a melt of ferro-magnetic material dissolved in a polymerizable solution through the sub-micron holes of a template situated under the poles of a magnet and subjecting the ferro-magnetic filaments seeping through the sub-micron holes to an intense UV radiation that polymerizes them.
Figure 30:
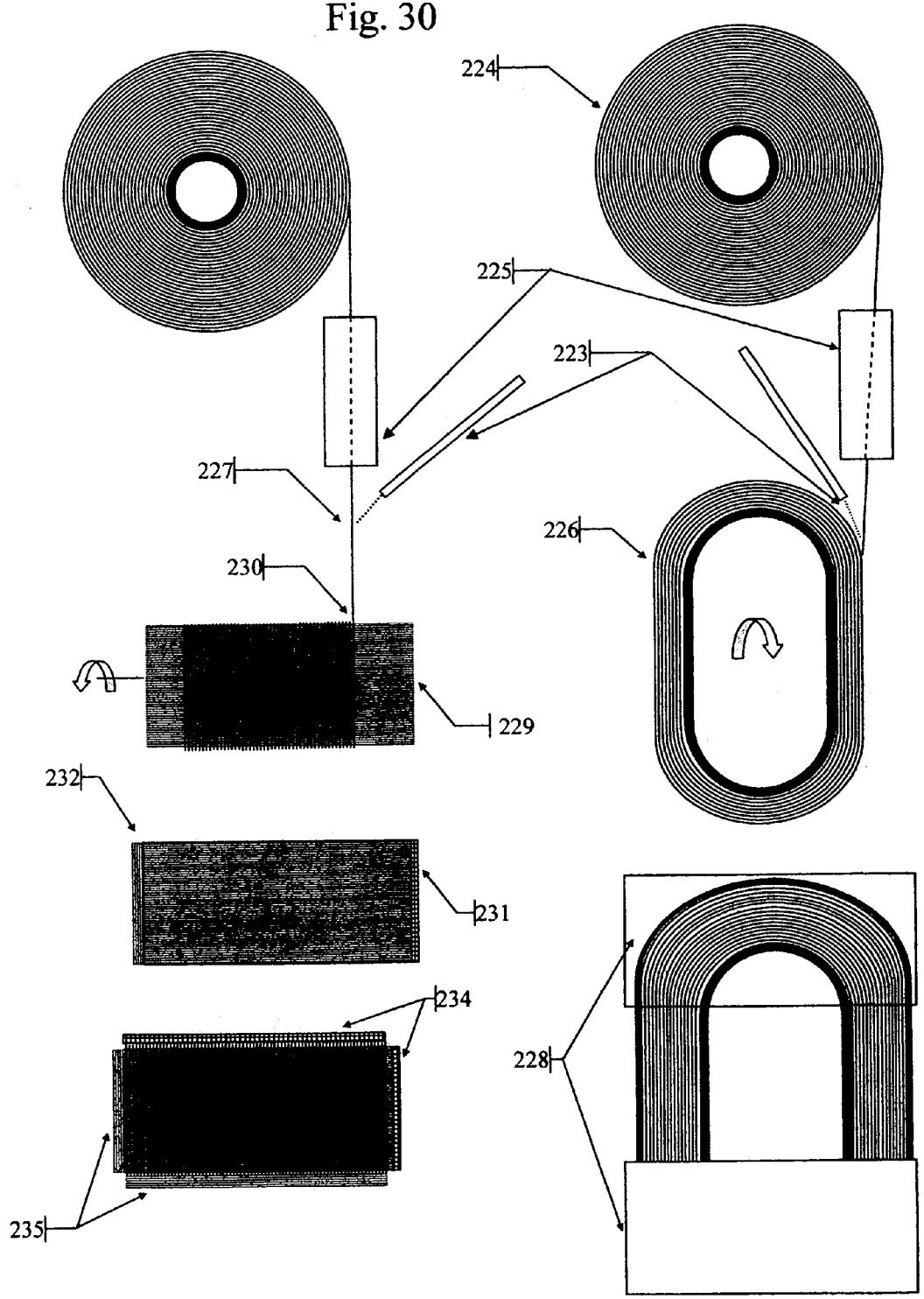
FIG. 30 illustrates the process of forming arrays of 3D vertical fibres by wrapping of a continuous fibre around a forming mandrel and cutting out the vertical sections.
Figure 31:
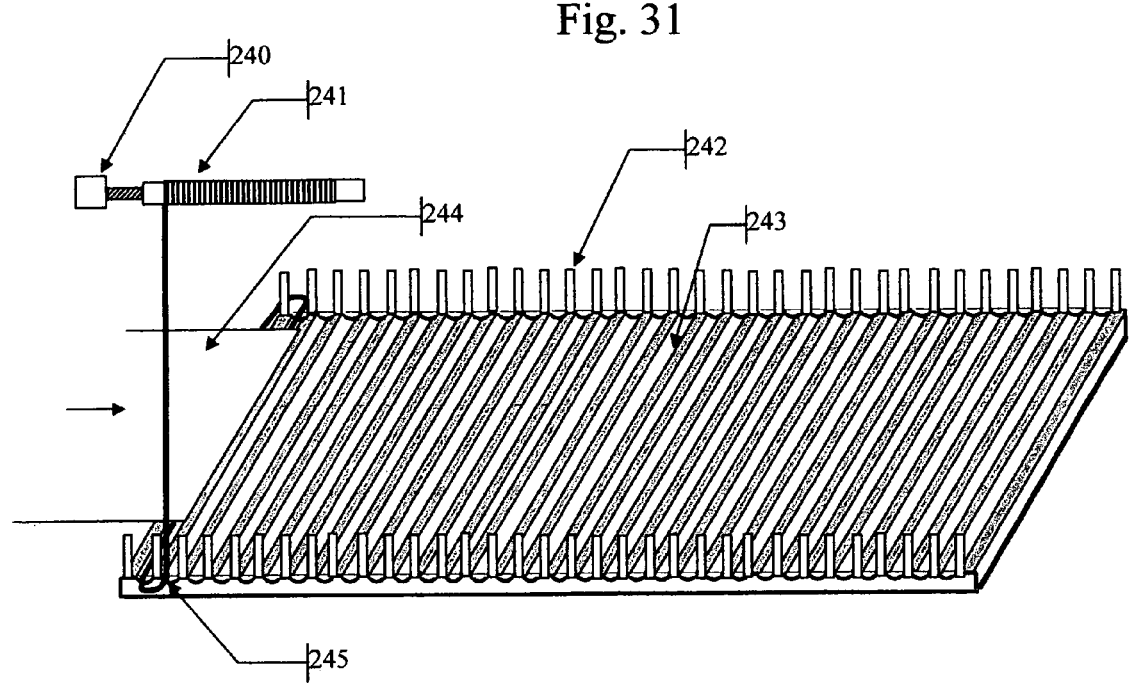
FIG. 31 illustrates the process of forming a criss-crossed array of nano-fibres by threading a nano-fibre filament continuously between studs situated at the periphery of the structure.
Figure 31:
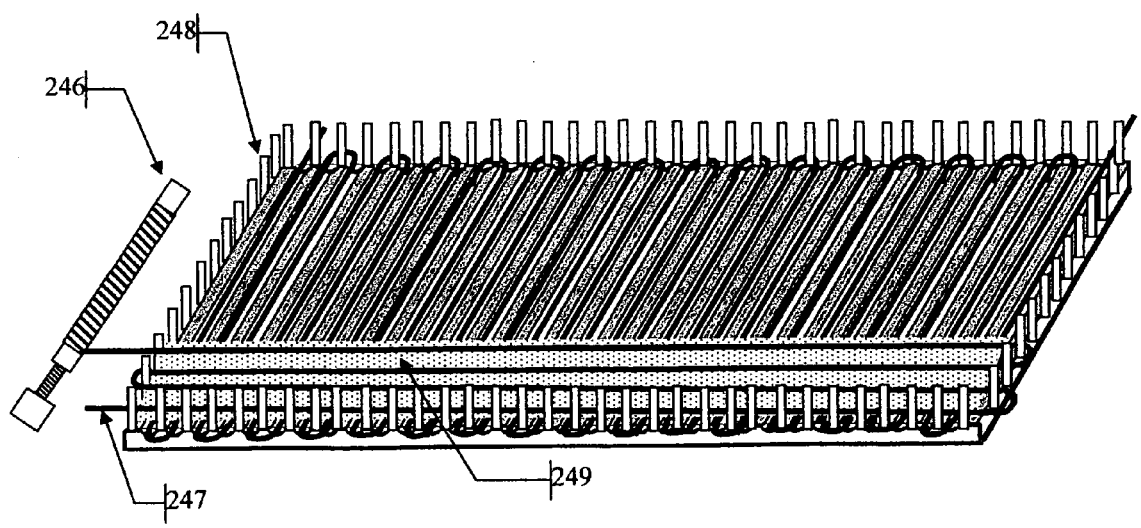
Figure 32:
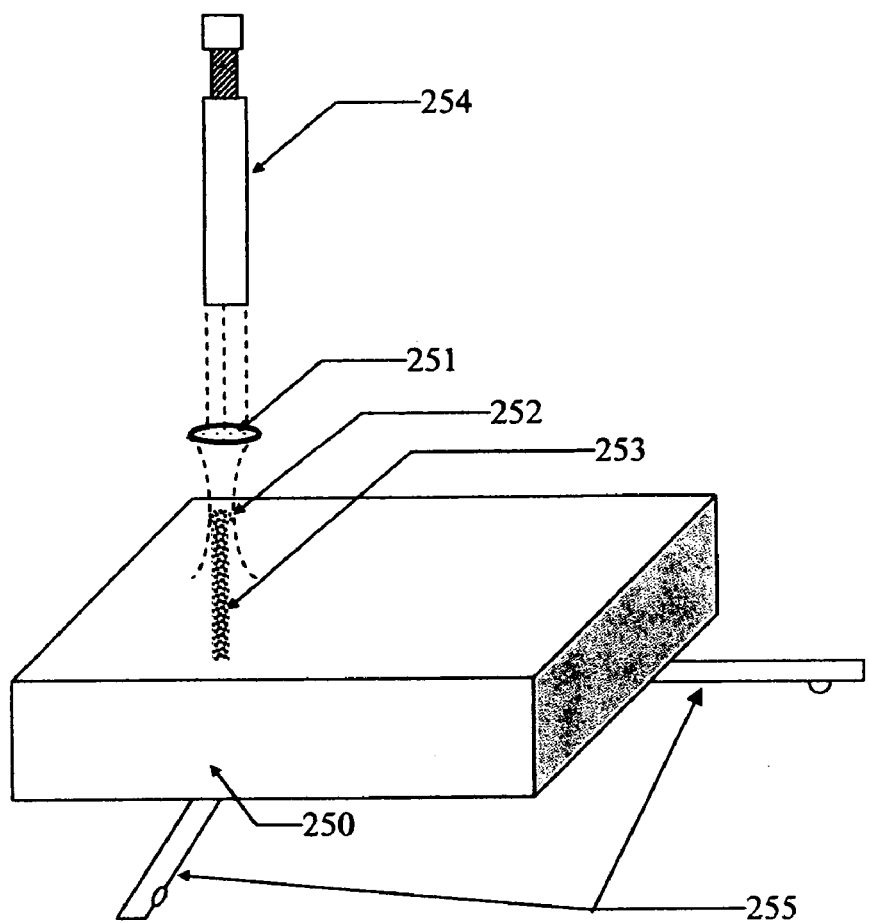
FIG. 32 illustrates the process of forming sub-micron holes in glass by irradiating the desired pattern with a UV beam and etching out the sections of the glass weakened by the UV radiation.
Figure 32:
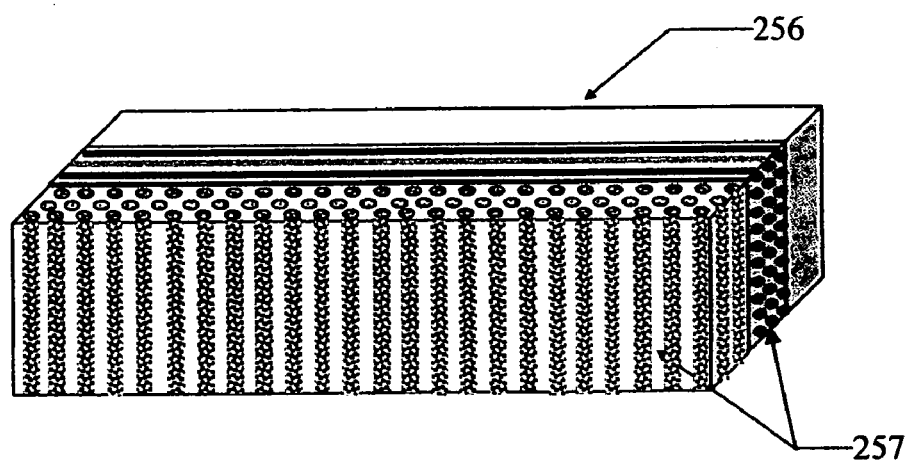
Figure 33:
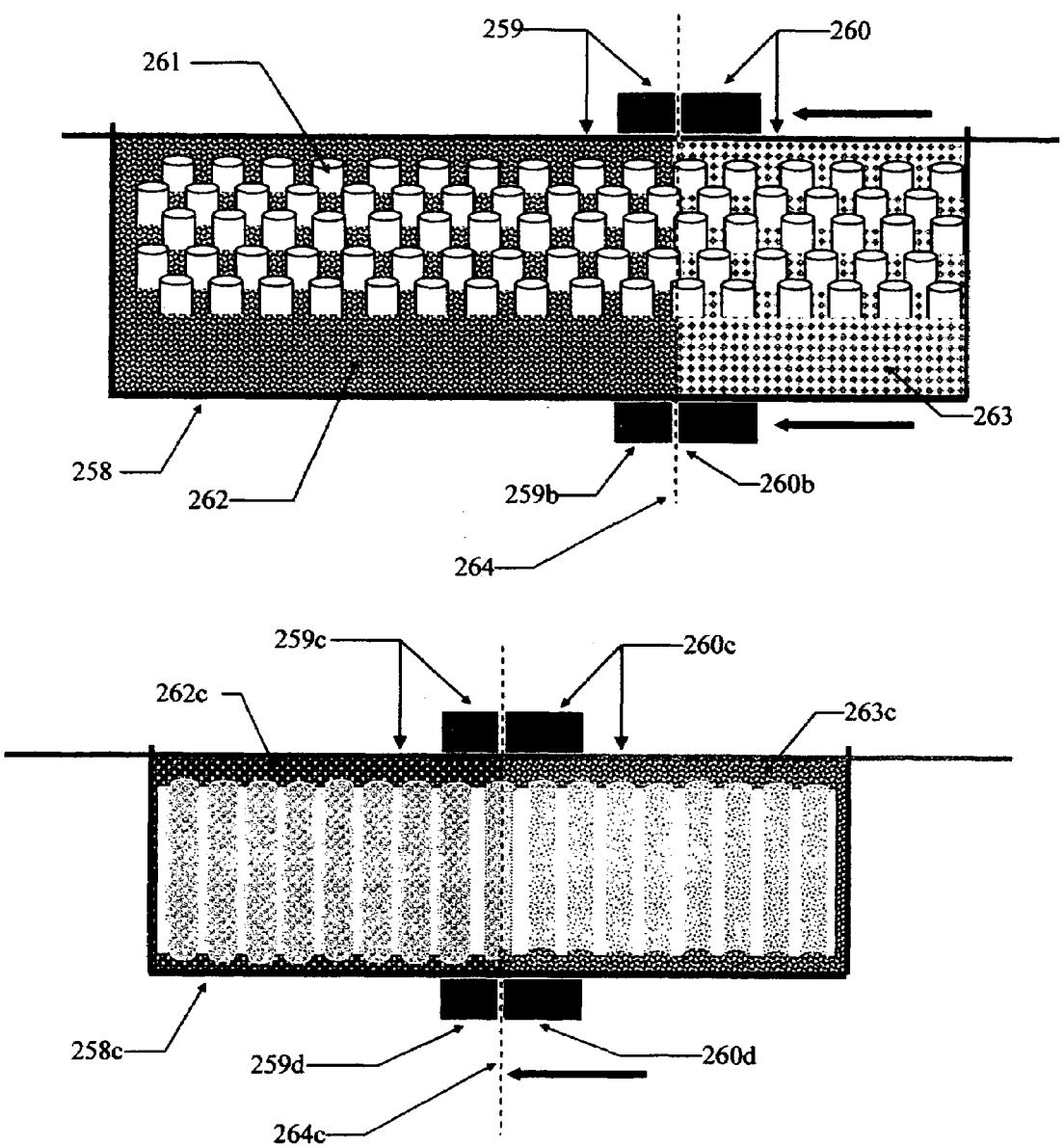
FIG. 33 illustrates the process of crystallization of scintillator powder to form PBCS structures
Figure 34:
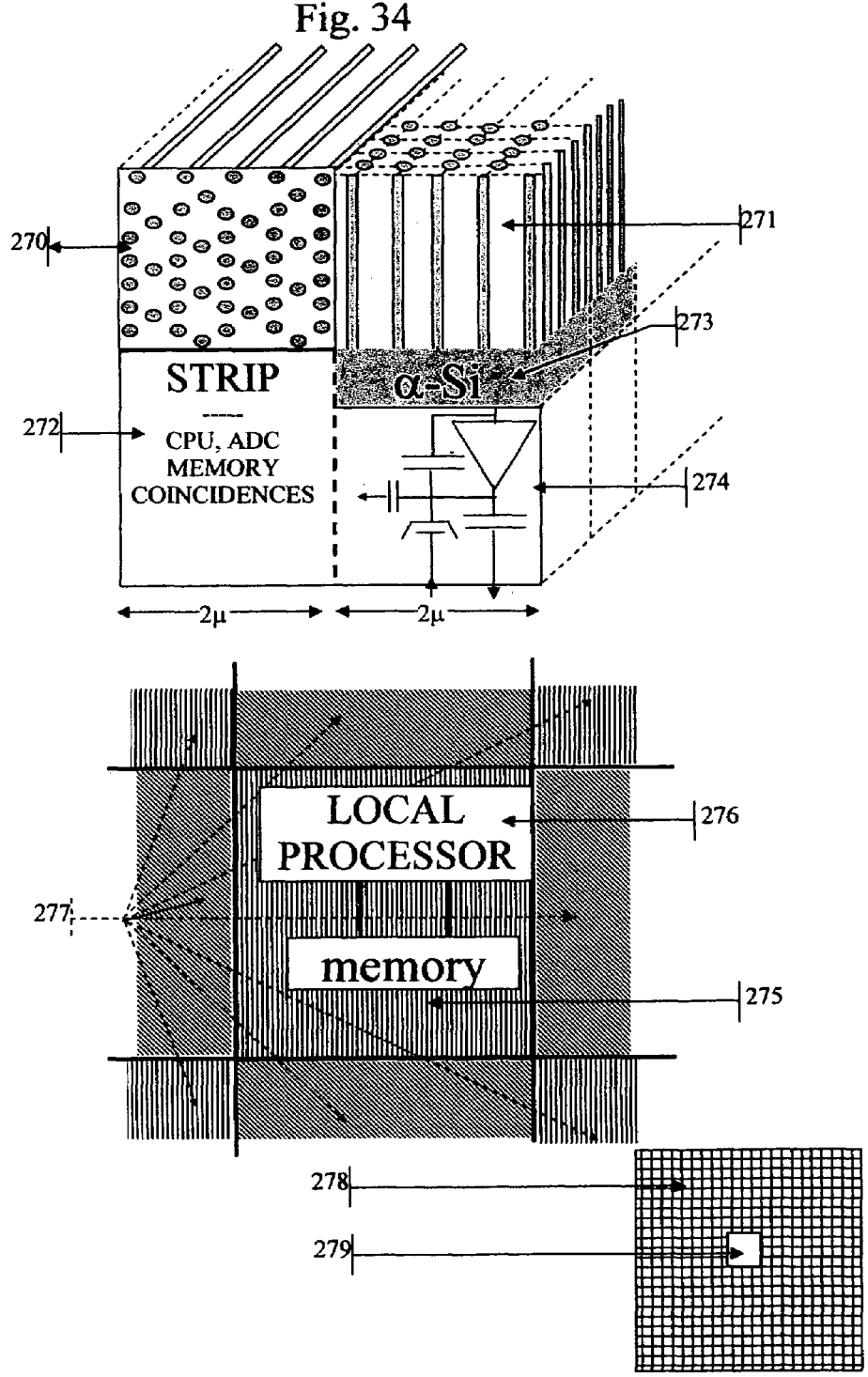
FIG. 34 illustrates an array of photoelectric converters juxtaposed to the ends of the fibres forming the PBCS, backed by active signal processing electronics.

FIGS. 25 through 34 illustrate manufacturing methods of PBCS and fiber scintillator structures. FIGS. 25, 26 and 34 illustrate manufacturing methods of one column at a time and are suitable for thin and small arrays, while FIGS. 27, 28 and 29 illustrate methods of manufacturing whole arrays in parallel. FIGS. 30,31 and 32 illustrate manufacturing of PBCS arrays out of scintillation nanofibers that have been premanufactured previously.

FIG. 25 illustrates a method of manufacturing a Photonic BandGap Crystal by drilling sub-micron sized holes in a matrix 162 with a high intensity, 100 Mhz femtosecond laser 161 that ablates the material, a method known to experts in the art. Holes of smaller diameter than the cross-section of the beam may be drilled by focusing the beam with lenses so that the effective intensity at the narrower "waist" 163 of the focused beam, is much higher and enables to ablate the material, without heating it. The plate may be moved in the X and Y directions by piezo-electric motors 165 that have positioning accuracy down to several nanometers, so that the desired geometry of holes may be drilled by quickly moving the plate under the femtolaser beam in small, for example $0.5\mu$ steps and repeating the process time and again, lowering the laser in the vertical direction after each sweep with a high accuracy piezo-electric motor 160. Thus sweeping a 10 cm line in $1\mu$ steps with a 100 Mhz laser in 1 sec will deposit $10^3$ pulses in each of the $10^5$ holes. $10^5$ linear sweeps will cover a 10 cm×10 cm plate in $10^5$ seconds or in approximately in 1 day. It has been empirically found that a 1 W femtolaser will ablate $(1.5)10^{-2}$ mm$^3$/sec (1.5)$10^7\mu^3$ of material in 1 sec; thus to ablate a hole of $0.5\mu^2\times1$ cm=(0.5) $10^4\mu^3$ it will take $7.510^{-4}$ seconds. As the sweep we envisaged above stays on top of a hole $10^{-5}$ seconds we need 75 sweeps in order to ablate the $10^{10}$ holes, or approximately 75 days If however instead of regular glass, an aerogel plate which is ~30 times less dense, is drilled and ablated, and a higher power femtolaser used, this time can be reduced by a factor of 75 or approximately to one day, which means that we need only one sweep which takes a day.

For example if in an aerogel block 166, 1 cm deep holes are ablated, a template for structuring 1 cm high pillars is formed. However as the aerogel consists of interconnected pores, in order to close the pores open to the walls of the drilled holes, they are first electrochemically coated. for example a Photonic Bandgap Crystal Scintillator is formed by filling the holes with a liquid scintillator. Alternatively the holes may be filled with a scintillator precursor material 172 which has a lower melting point than the silica aerogel which has a melting temperature of around 1200° C. The scintillator precursor may be for example a ultrafine powder of LaClBr:Ce (melting temperature 950°) or doped p-terphenyl that melts at 214°. Upon heating the structure 172 above the scintillator melting temperature and letting it to slowly cool, it will density and crystallize in the form of columns 173, separated by very low density walls. If desired, the silica aerogel walls may be removed by first fracturing and shattering the delicate pore walls by ultrasound and then sucking away the debris, leaving the scintillator columns 174 separated by air or aerogel. The filaments may also be supported mechanically by gluing them laterally at the base and several heights above 175.

This method may also be applied to the manufacturing of "woodpile" type 3D PBCS structure, first drilling holes on a set of slices on one of the faces 167 and then a second set of slices 168 on the orthogonal faces. More complex PBCS structures may be formed by using the structure of columns obtained, as a sacrificial template and filling the interstitial space between the columns with a fine scintillator powder that is then pressed, sintered or melted and crystallized. The sacrificial columns are then either etched away or ashed depending on the materials and their melting temperature.

FIG. 26 illustrates a 2D Photonic Bandgap Crystal of long pillars manufactured by polymerizing a tubular section 185 of a photopolymer solution with a laser 180 beam strongly focused 181. The high intensity at the waist of the focused beam 184 will polymerize the photopolymer solution but leave it transparent to the wavelength of the laser. In this method sweeping the laser beam linearly across the vessel containing the photopolymer in small 1μ steps and then sequentially line after line, will polymerize the top layer of the photo-polymer in discrete spots. Physically lowering the laser with piezo motors in small nano-steps, after each lateral sweep of the vessel, will polymerize the photopolymer, layer after layer, in discrete tubular sections 187. The polymerized pillars are held mechanically from the top 183 of the vessel. The level of the non-polymerized solution 188 between the growing pillars 187 may gradually be lowered after each sweep to prevent contact with the polymerized sections that may cause further growth of their cross sections. After the desired length of pillars is reached the array 189 is cleaned with an appropriate solvent to remove the remaining non-polymerized solution and the pillars mechanically secured at their two ends. This manufacturing process may be suitable for forming plastic scintillator arrays.

FIG. 27 illustrates a process of forming a two dimensional columnar array, by depositing the whole structure slowly out of superheated liquefied material, like a PVD (Physical Vapor Deposition) process. This method is suitable for forming arrays of crystallized scintillators. The process is started by forming an array of very sharp, needle like extremities around which the crystalline array will aggregate. A two dimensional array of needle-like elevations above a plate may be nanoimprinted by first embossing by pressure, an array of semi-spherical elevations 193 on a substrate. This substrate is then used to nanoimprint staggered semispherical depressions 190, 191, 192 on another preferably conductive plate 194, thus forming a plate 195 with sharp elevations.

A second electrically conducting plate 205 of sub-micron sized holes defining the desired two-dimensional periodicity of the structure is formed, as explained below in conjunction with FIG. 28. This "holey" plate 205, is placed at some distance over the surface of a superheated melt of material 197 heated by convection 201, and an electrostatic field 202 is applied between the two plates. The evaporated molecules of the melt pass thru the "holey" plate 205 and are attracted towards the photo-voltaically cooled 200 sharp points of the upper plate 203, where the electrostatic field is the greatest and start to accumulate on them. The upper plate 198 is slowly retrieved upwards as the evaporated molecules accumulate one on top of the other in thin fibers 203. The rate of retrieving the plate from the surface of the superheated melt, determines the diameter of the accumulated material columns. To start the crystallization process the tips of the elevations of the template may first be coated with nano crystals of the same substance, for example by first coating the tips with some glue and causing the template of tips hover over and touch a powdery layer of nano-crystals of the same material.

This method may also serve to build a polymerized array. In this case a UV source may be directed to the tips of the columns to cure and polymerize the gradual build-up of material. Such an array so formed may then serve as a sacrificial template to build a Photonic Bandgap Crystal Scintillator.

FIG. 28 illustrates the process of forming a 2D array of long pillars by extruding a curable and preferably electrically conductive substance, such as a metallic nanocomposite sol in the process of being gelated, an epoxy or a photopolymer solution, through the nano holes 208 of a plate.

Templates of nano-holes may be formed by first nanoimprinting, by pressure, a recessed pattern of holes 206 on a masked substrate and then plasma etching the recessed pattern with highly directional reactive-ion etchant. The reactive-ion plasma is directed at the mask along the perpendicular axis, and vertical channels of the desired shape are created in the substrate. The resulting array of elements defines the desired two-dimensional periodicity of the structure. The holes of the thin plate are then covered with a resist that can later be dissolved and the plate thickened and structurally reinforced by electro-plating the areas around the holes. The thickened "holey" plate 208 is then incorporated onto the bottom of a vessel 211 that may be slightly pressurized without damaging the holey plate 208.

A second plate 213, the negative of the "holey" plate, having elevations at the places where the "holey" plate has holes, is placed on top of a retrievable table 218 movable up and down by precision piezo nano-motors 217, and pressed against the holey plate at the bottom of the pressurized vessel. The vessel 211 is filled with the light curable substance 212 and pressurized 210 to start extruding the material through the nano-holes. The opposite plate with the elevations 213 is cooled by a thermoelectric cooler and a light source 215 which may be a set of diodes are placed around the bottom of the vessel, their beams directed at the exit holes 214. An electrostatic field may be established between the melt 212 and the plate 213 supporting the exiting nano-filaments.

Slowly retrieving the table 218 that supports the cooled plate with elevations 213, enables the photo-polymer or the sol-gel seeping through the holes 214 of the pressurized vessel 211. The pressure may be controlled by a valve 210 that links the pressure vessel to a pressurized gas source The substance passing through the nano-holes of the plate 218 is immediately polymerized, cured or gelated and dried by the appropriate radiation and solidifies supported by the plate 213.

The melt may also consist of a plastic scintillator that polymerizes at the exit. The viscosity of the melt may also be reduced by a solvent that immediately evaporates after traversing the holes. If the melt is electrically conductive the electrostatic field between the seeping material and the plate with elevations will keep the exiting material in the vertical direction. The support table holding the plate with elevations is retrieved by a set of high precision piezo nano-motors 217, at the same rate that the melt exits the holey plate. The array of nano-filaments may be reinforced by embedding it into an aerogel matrix formed by a sol-gel process.

FIG. 29 illustrates a similar extrusion process of forming a 2D array of of long pillars as explained in conjunction with FIG. 28 above, with the difference that the extruded filaments are ferromagnetic and the entire process is performed between the poles of a magnet 220. Pressing a ferromagnetic melt through the nano-holes of the plate as explained above, helps keep the direction of the extruded nano-filaments 221 straight.

FIG. 30 illustrates the process of forming parallel or criss-crossed arrays of plastic glass or omnidirectional scintillator fibers, starting from prefabricated fibers of the desired material, refractive index and cross sections. The PBCS structures are obtained by placing the individual fibers at the proper distances. The fibers originally coming in a round drum 224 are first, thinned by heating and pulling under tension 225 until the desired cross section is reached. The fiber is then wrapped around a forming mandrel 226 having straight sections, at proper distance one turn from another, while injecting a layer of soluble film 223 between fibers and layers of fibers to achieve and maintain the desired separations that determine the Bandgap. Arrays of vertical fibers are obtained by wrapping around the desired number of turns and then cutting out the curved sections 228, leaving the straight ones. Structures of criss-crossed arrays may be obtained by first wrapping a planar array of the desired number of turns, and then turning the mandrel by 90°, wrapping around the previous layers 229 a second array of layers 230 perpendicular to them, while injecting a thin film 223 between the layers. The process is repeated the desired number of times and at the end the curved sections are cut out and the straight sections constitute the desired structure. Once the structure is finalized the ends of the layers are mechanically secured, 231, 232, 234, 235 and the separating films are chemically dissolved.

FIG. 31 illustrates an alternative method to that explained above in conduction with FIG. 30 of forming parallel or criss-crossed arrays of plastic glass or omnidirectional scintillator fibers, starting from prefabricated fibers of the desired material, refractive index and cross sections. In this method the distances between fibers is determined by studs 242, 248 situated at the periphery of the structure. The fiber originally wrapped around a drum 241 is threaded forth and back between consecutive studs 242 while a piezo nano-motor 242 advances it in steps. After each layer a thin film 244 is evaporated and the following layer is built upon it, threaded on the studs at the periphery of the structure. If a criss-crossed structure is desired, after a given number of layers in one direction the fiber is threaded between the studs 248 in the perpendicular direction upon a film 249 that separates the layers.

FIG. 32 illustrates the process of forming a PBC lattice consisting of approximately 200 nm holes 253 in a glass block 256 by irradiating the desired pattern with a narrow and focused 254 UV beam, for example with an excimer laser. The UV irradiation destroys the bonds of the glassy structure along a tubular section 253. The glass block may be moved in the lateral plane by high precision piezo nano-motors 255. The weakened tubular sections may then be etched out with a weak solution of hydrofluoric acid. The glass block may be irradiated and then etched from two orthogonal directions 257, thus forming a wood-pile like criss crossed PBC structure. If the glass block is a glass scintillator the end product is a PBCS array. The "holey" glass structure may also be used as a sacrificial negative template to form a PBCS of pillars as illustrated in FIG. 33 below.

FIG. 33 illustrates the process of crystallization of scintillator powder inserted between the pillars 261 of a 2D photonic bandgap structure produced as described in conjunction with FIGS. 27, 28 and 29 or within the holes of a sacrificial template, such as the structures illustrated in FIGS. 25, 26 and 32. The ultrafine scintillator powder composed of nano crystals of less than 100 nm in diameter around the pillars 261 or within the holes 262c is heated and melt by the inductive furnaces 259, 260 and 259b, 260b. Then a strong temperature gradient 264 is formed between the furnaces 259 and 259b one one side that keep the melt at a temperature slightly higher than the melting temperature of the crystal, keeping the crystal liquefied and the furnaces 260 and 260b that keep the temperature of the melt below the melting temperature, where crystallization starts. The inductive furnaces 259 and 260 on one side and the furnaces 259b and 260b on the other side are placed across the narrowest dimension of the structure and vessel 258 in order to make the temperature gradient as sharp as possible. The temperature gradient may be sharpened by adding penetrating IR laser heating for example with several $10.6\mu$ $CO_2$ lasers directed at the mid points between the inductiv heaters where their reach is the least. The set of furnaces are extremely slowly swept along the long direction of the crystal to enable uniform crystallization without cracks until full crystallization of the interstices band holes melt is achieved. The crystallization process of the powder within the holes of a template is similar; sweeping slowly the furnaces 259c, 260c, 259d and 260d along the vessel 258c will crystallize the melt within the holes. It is noteworthy to mention that for the purpose of structuring a Photonic BandGap Crystal scintillator there is no need to achieve a "single crystal" structure across the entire crystal as the scintillations have to travel only along the pillars or interstices between the holes of the PBCS structure to the edges, so that multi-crystalline structures are acceptable. Obviously the template material must have a higher melting temperature than the scintillation crystal and consisting of a material that does not interact with it. For example a glass PBC template that melts above 1200° C. is suitable as a template for forming a PBCS structure for Lanthanum Chloride Bromide that melts at 950°. The template may be eliminated chemically without damaging the crystallized structure as is the case with glass or by shattering it with ultrasound as is the case with aerogels, and sucking away the debris.

FIG. 34 illustrates an array of photoelectric converters juxtaposed to the ends of the fibres 271 forming the PBCS and backed by active signal processing electronics. The stream of photons propagating from their source down (or up) in orthogonal direction from are converted to photo-electrons by a thin amorphous silicon film 273 that can achieve quantum efficiencies above 80%. In general the high concentration of photons leaving the crystal through a basic resolution element enables to forego Amplified Photo-Detectors (APD) and thus reduces both complexity and costs. The photoelectrons exiting the amorphous silicon film 273 are collected by "active pixel" electronics 274 immediately beneath the film; they include an operational amplifier to integrate the incoming signal, a differentiator to determine its timing and a reset switch to reset the circuit when this information is relayed to the sub-array processor, all implemented in deep submicron technologies of $0.13\mu$ or lower. Current technology enables to implement these functions in a $[(2\mu) \times (2\mu)]$ pixel.

A $512\mu$ long strip 272 adjacent to the Y axis along the 256 resolution elements and $2\mu$ wide along the X axis, includes circuitry for further processing the outputs of the 128 pixels. The differentiated outputs of all the 256 elements are time stamped and the pulse height of the pixels are passed to an ADC that digitizes the pulse height and the corresponding timing information and stores them together in the local memory of the 256 pixel long strip. Then the local storage capacitors and the charge sensitive preamplifiers are reset to zero and stay ready to receive another pulse. 512 strips, each strip $512\mu$ long and $2\mu$ wide, servicing 256 resolution elements, form together a sub-array with a real estate of $512 \times 2(1024\mu) = (1024)^2 \mu^2 \sim 1$ $mm^2$ containing 512 strips. Each sub-array 275 has its own local processor 276 which analyzes the charge content of all the pixels in the sub-array, and constructs a possible "track" based on the spatial continuity of and the center of gravity of pixels that show a charge and were in coincidence. It then aggregates the charge accumulated by the pixels of the tentative "track" within a time window, to derive its "energy" and transmits this information and the coordinates of the "track" together with the timing information to the main processors that identify the transmitting array and relay this information to a main processor 279. In a 10"×10" array there are 256× 256=65.10³ sub-arrays 277 that are connected in 256 "rows" and 256 "columns" 278 to a main processor 279 servicing through the local processors and the strip electronics, a total of 86 megapixels. In case the 3D PBCS is built out of 2D lattices, each orthogonal to the other, as described above, there is a need for 2 such electronic arrays. Coincidences registered between one or more "rows" and one or more "columns", at both orthogonal faces of the PBCS structure, indicate a relevant event; their content is processed by the main processor for reconstructing the 3D coordinates of the event and its pulse height. The pulse height distribution in proximal events is analyzed to extract the coordinates of the track and the aggregate energy. This information is then transferred to a more powerful computer for analysis of the sequences of tracks and determining the plausible energies of the incoming γ rays as explained below.

In principle, the high concentration of photons leaving the crystal through a basic resolution element, allows an alternative optical solution to drastically reduce the number of photodetectors needed, by switching to a two dimensional optical matrix scheme. The 2D matrix structure may be implemented by dividing the stream of photons exiting each resolution element of the crystal to two branches, combining one of the branches of each element into "rows" and the second one into "columns" of wider optical light-guides. Each stream of photons exiting a resolution element, may be channeled by the light guides or optical fibers to a different photo-detector while coincidences between rows and columns determine positions of the resolution elements, while the sum of the signals in coincident pixels gives the amplitude of the event in the PBCS detector. The optical solution however poses some geometrical and optical problems such as the difficulty of bending lightguides or optical fibers and the inevitable losses in guiding the stream of photons into the lightguides or optical fibers.

Figure 35:
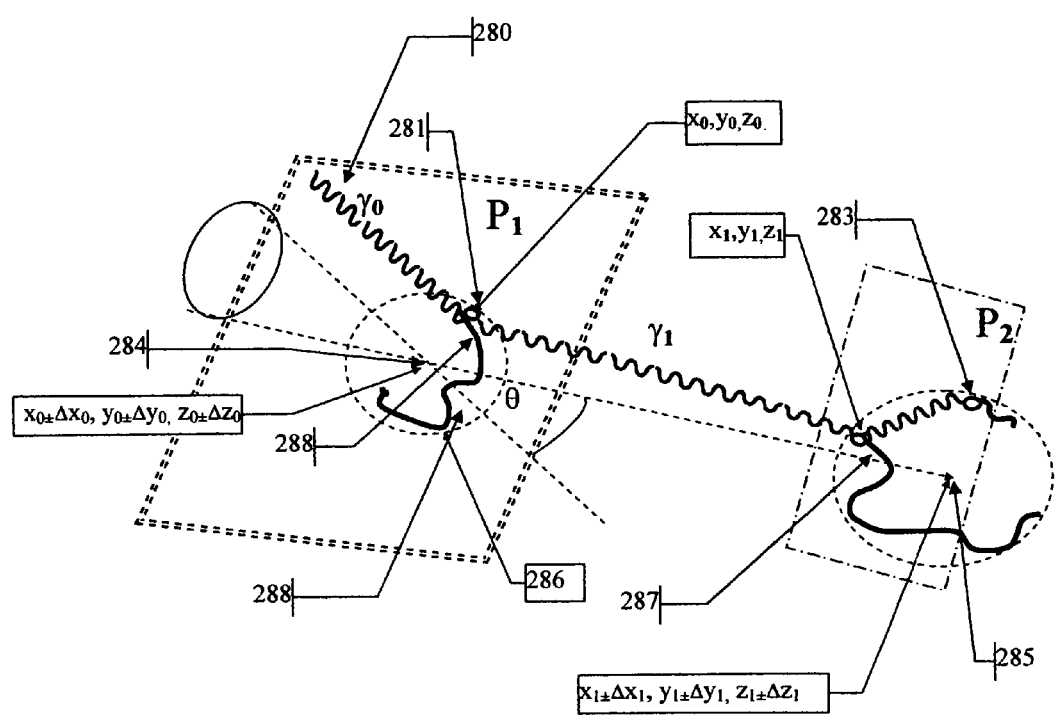
FIG. 35 illustrates the Compton scattering in 3D and the prior art of finding the direction of a γ ray.

FIG. 35 illustrates the Compton scattering process in 3D and the prior art of finding the direction of a gamma ray 280. The parameters that have to be determined in a Compton Camera are the coordinates of the initial Compton scattering 281, the following scattering (photoelectric or a second Compton) event 287, the energies of the scattered gamma ray and the recoil electron 286, and the recoil electron's direction 288 or the coordinates of another point on the "scattering plane". The accuracy of these parameters determine the accuracy of the calculated direction of the incoming gamma ray. In the prior art the direction of the electron is not measured as the Coulomb scattering given below causes the electron to start deviating by $\theta^{rms}$ from its initial direction, within a distance (z) smaller than the spatial resolution of the legacy detectors, $$\theta^{rms}=(14 \text{Mev}/cp)(z/L_r)^{1/2}$$

where $\theta^{rms}$ is the average deviation of an electron scattered by the Coulomb interaction with the stopping atoms, at a distance z from the impact, c is the velocity of light, p the momentum of the electron and $L_r$ the radiation length of the electron and given by $$[(hc)^2\{4Z(Z+1)\alpha^3 N_0/A m_e^2\}\ln(183/Z^{1/3})]^{-1}$$

where A is an empirical constant.

The measured parameters in most prior art experiments are the positions of the initial 286 and follow-up 283 scatterings, both limited by the extent of the tracks in 3D and the spatial resolution of the detector, and the energies of the knocked-off electrons. Not knowing the direction of the recoil electron gives rise to the "cone ambiguity" as explained in the Background section above. But measuring only the energy of the recoil electron, still leaves a very large indeterminacy as to its real position, equal to the extent of the electron's track. Thus the ill definition of the coordinates of the initial 281 and following 283 scatterings contribute a large indeterminacy to the direction of the "line" connecting them. The indeterminacy Δθ to the direction θ of the scattered gamma ray is compounded if the two events are close by, within the same detector for example. Using two detectors far apart, reduces this indeterminacy at the price of decreasing the effective solid angle covered by the detectors, strongly reducing the efficiency of a Compton camera. Some heroic attempts to measure the direction of the recoil electron with silicon or gas detectors have suffered both from the unsufficient spatial resolution of the detector and coverage of a limited solid angle of the scattering.

Figure 36:
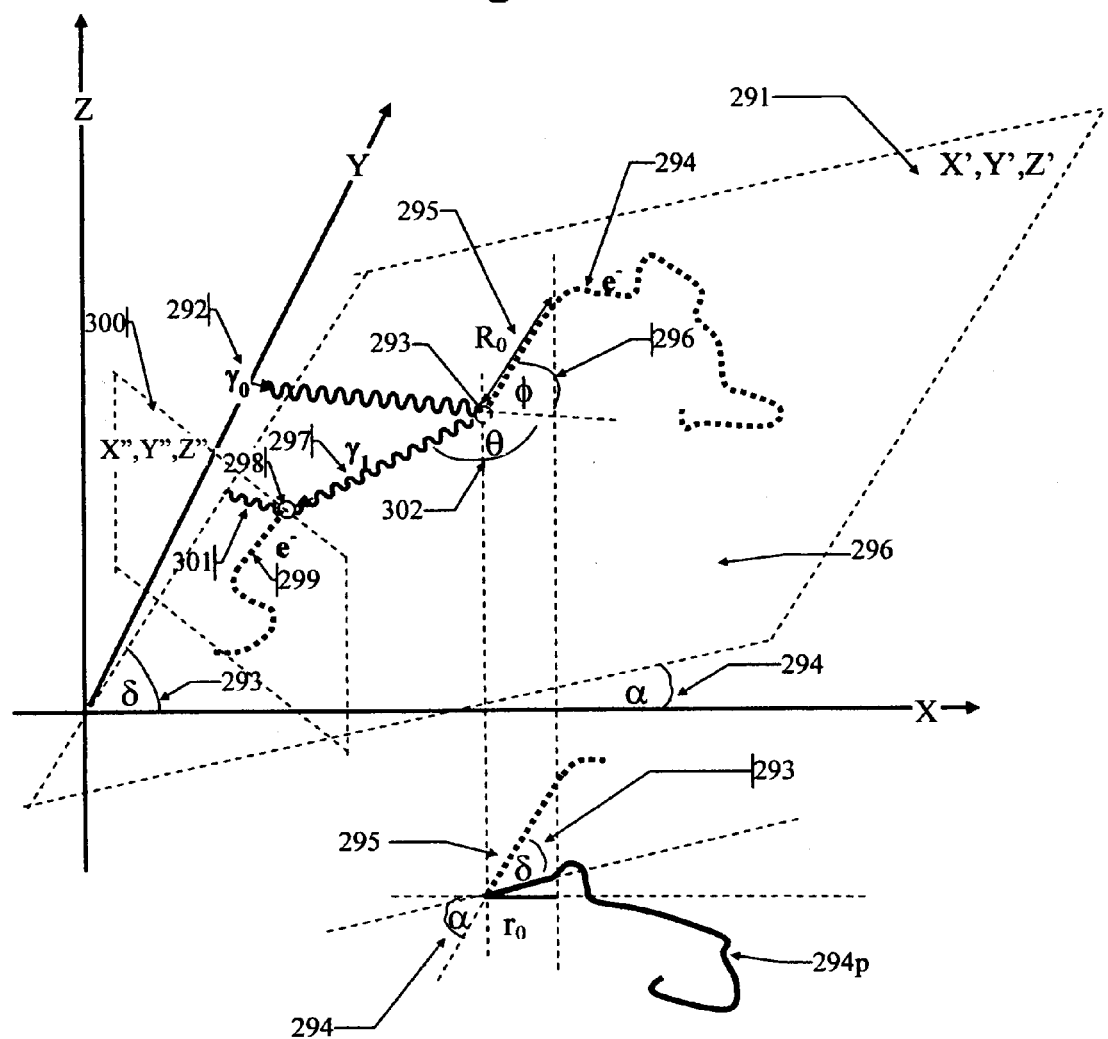
FIG. 36 illustrates the way to find the direction of the recoil electron after a Compton scattering.

FIG. 36 illustrates a method to find the direction of the straight section 295 of the recoil electron in a 2D PBCS structure, where only the projection of the track onto the (X,Y) plane is known. The length of the track projected on the (X,Y) plane, ($r_0$) is related to the length of the track ($R_0$) 295 in the "scattering plane" (X',Y',Z') 291 by $$r_0 \cos\alpha = R_0 \cos\delta;$$

where α 294 and δ 293 are the inclination of the "scattering plane" (X',Y',Z') 291 in the (X,Y,Z) space.

However the angle α 294 on the X,Y plane and the length ($r_0$) can be measured, while the true length $R_0$ of this portion of the track can be calculated theoretically, by the Continuous Slow Down Approximation (CSDA), knowing the stopping power of the material and the energy of the electron. Thus the inclination δ of the "scattering plane" 293 can be obtained from $\cos\delta = \cos\alpha \, (r_0/R_0)$;

In this way the direction of the recoil electron in the absolute (X,Y,Z) space can be determined, thus resolving the "cone ambiguity" of the Compton scattering event.

The key to a precise determination of the direction of the incoming gamma rays is finding the direction of the recoil electron with a high resolution PBCS radiation detector. Thus it is important to try to minimize the Coulomb scattering of the electron and its deviation form a straight line, at least at the beginning of the track. Selecting a scintillator with a low excitation energy, so as to slow the recoil electron in small "steps", and increasing the mean free path between two interactions. The result of both requirements is to lengthen the track of the recoil electron and obviously the initial part of this track. The low density requirement is greatly helped by the PBCS structure, if it consists of a scintillator having large, "holes" or small fibers in an open hexagonal geometry, as illustrated in FIG. 3. Thus for example if the hole's diameter is 95% of the hole-to-hole distance, the scintillator will occupy only 18% of the volume, meaning an effective fivefold reduction of the density or fivefold lengthening of the electron's track, including its very beginning. A low excitation energy dictates organic scintillators. A doped p-terphenyl plastic scintillator for example has mean excitation energy of 71 eV, as compared with 382 eV for a Lanthanum Chlorine Bromide which has a high light output and in general would be preferred over the doped p-terphenyl scintillator.

Doped p-terphenyl scintillator with a low mean excitation energy of 71 eV, has the highest light output of 27 ph/keV of organic scintillators and is therefore the best candidate for minimizing the multiple Coulomb scattering deviation. To increase the width of the Bandgap and the effective critical angle reflection the p-terhenyl plastic scintillator may be coated with thin ($\lambda$/4) layer of $TiO_2$, ZnO or $ZrO_2$ to increase the refractive index contrast from 1.65:1 to above 2:1.

In the CSDA (Continuous Slow Down Approximation) the length of the track of a 44.6 keV recoil electron engendered by a 140 keV gamma ray back scattered at 135°, in a 82% empty p-terphenyl plastic scintillator, is 169µ. At a 71 eV mean loss of energy per interaction, this means 3.7 interactions per 1µ or an interaction every 270 nm. The deviation of 44.keV recoil electron from its initial direction $\Delta\theta$ as a result of Coulomb scattering with free electrons, losing each time 71 eV on the average (0.16%) although minimal, is however cumulative and can be estimated using Moliere's scattering theory. As the variance $\Delta\theta$ is random and has a semi-gaussian distribution, the deviations of the track can be fitted with a gaussian distribution and its average estimated. Thus the 44.6 keV recoil electron will undergo 64 scatterings in 17µ while losing 10% of its energy. The deviations being distributed at random their variance will be of the order of $(64)^{1/2}=8$ deviations which can be estimated using the empirical formula above. At a low energy of 44 keV, a single deviation $\theta^{rms}$ being of the order of 0.1°, the total deviation in 64 scattering events may be as high as 6°-7° but the variance in determining the direction of the low energy recoil electron in the 82% empty p-terphenyl plastic scintillator is 0.8°<1°.

However the variance in determining the direction of the recoil electron is also a function of the spatial resolutions of the beginning and end of the "straight" part of the track, and at low energies where this "straight" part is rather short, the spatial resolution may be the dominant factor. Thus to minimize the variance of the spatial resolution in finding the beginning and the end of the "straight" section of the track, the resolution elements ought to be as small as possible and the positions ought to be determined by finding the "center of gravity" of all the resolution elements surrounding the beginning or end of the "straight" sections.

Figure 37:
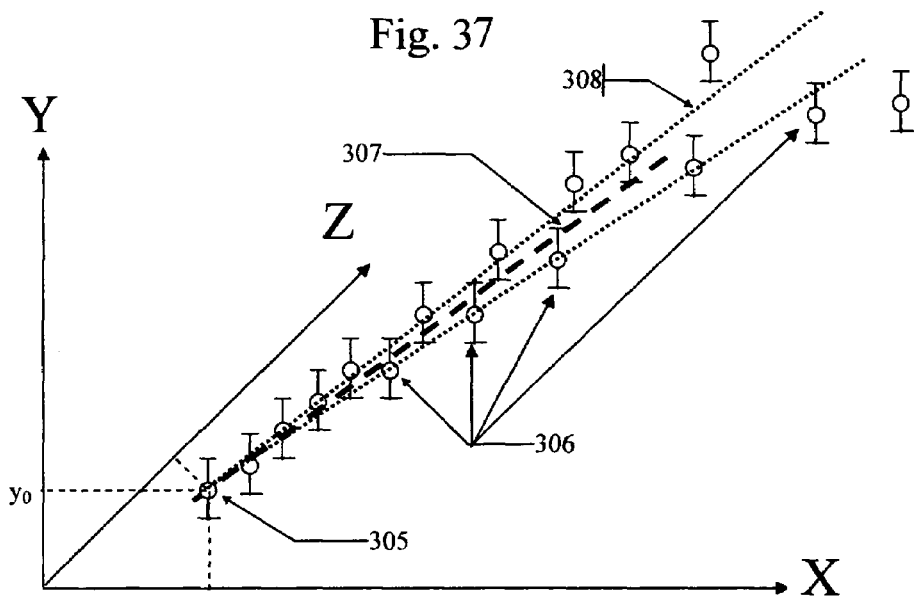
FIG. 37 illustrates the method of finding the initial position of the recoil electron following a Compton scattering

FIG. 37 illustrates the measured deviations 306 of the track of the recoil electron from a straight line 307. The mean value of the initial direction of the track may be interpolated from its position while losing approximately 10% of its energy, by finding the best fit to a straight line that minimizes the deviations, and a variance 308 from the average direction may be calculated. In the example given above of the 44.6 keV recoil electron in a 82% empty p-terphenyl scintillator, 10% of the energy is spent in 17 scattering events. The positions of these 17 scattering events enables to find the mean direction of the recoil electron and even to find a more accurate position of the initial first scattering event 305, as the first point may already have had a large deviation and what counts is the average deviation.

The coordinates of the interaction point between the scattered gamma ray and the photo-electron whose track starts on the scattering plane but may propagates out of it are also found in the same way, by finding the best fit with a straight line of the initial part of the track and extrapolating this line to the beginning of the track.

Thus the high spatial resolution of PBCS radiation detectors, also enable to reduce the distance between the Compton scatterer and the Photo-electric detector thus greatly improving the efficiency. At low energies it even enables to have the same PBCS detector to detect both events, thus achieving a $4\pi$ solid angle.

At medium and high energies above 500 kev forward scattering is dominant, while at low energies the cross section at back scattering angles, increases appreciably. Table 3 shows for a Compton scattered incoming gamma ray of 140 kev, the energies of the gamma rays scattered, fully backwards (180°), at 135° backwards, at right angle (90°), at 45° forward and straight forward at 0° and the corresponding scattering angles of the recoil electron and its respective energies.

TABLE 3

| $E_0$ = 140 keV $\alpha$ = 0.274 | $\theta = 180°$ | $\theta = 150°$ | $\theta = 135°$ | $\theta = 90°$ | $\theta = 89°$ | $\theta = 85°$ | $\theta = 45°$ | $\theta = 5°$ | $\theta = 0°$ |
|---|---|---|---|---|---|---|---|---|---|
| $E\gamma 1 = E_0/[1 + \alpha(1 - \cos\theta)]$ | 90.439 | 92.64 | 95.38 | 109.9 | 110.30 | 112 | 129.4 | 139.85 | 140 |
| $\phi \cot\phi = (1 + \alpha) \tan \theta/2$ | 0° | 12° | 18° | 38° | 38.5° | 40.5° | 62° | 87° | 90° |
| $E_e = E_0 - E_1$ | 49.561 | 47.36 | 44.62 | 30.1 | 29.69 | 28 Kev | 10.6 | 0.15 | 0 keV |

The table above illustrates the problems encountered when trying to assess the direction of an incoming low energy gamma ray, by measuring the energies and directions of the scattered gamma ray and the recoil electron. At first sight it looks like that the direction of the incoming gamma ray would be best assessed by looking solely at the energies of the scattered gamma rays and finding those events where the energy corresponds to 180° back scattering. However as $[(\partial\theta/\partial E)\sim 1/\sin\theta]$ which for $\theta=0$, $(\partial\theta/\partial E)\sim\infty$ it requires a very small $\delta E$ or measuring the energy with infinitely (!) high accuracy. In practice an energy resolution of 1% of the back scattered gamma ray (900 eV) would determine the angle up to 15.5°; moreover not knowing the exact energy of the recoil electron would mean the indeterminacy of the direction of the incoming gamma ray would be up to a "cone" whose apex is ±15.5°.

Measuring the energy of the backscattered gamma ray at 135° reduces the differential angular indeterminacy $(\partial\theta/\partial E)$ to 4.3°/kev and for a resolution of 1 keV to a cone whose apex is ±4.3°.

Eliminating the "cone ambiguity" requires determination of the "scattering plane" and consequently the determination of the recoil electron's energy and direction as discussed above in conjunction with FIG. 9. Thus it is essential to measure the energy of the scattering gamma at an angle that corresponds to an optimal $(\partial\theta/\partial E)$ that leaves enough energy for the recoil electron so that its direction $\phi$ too, can be assessed with an accuracy $\partial\phi$ of the same magnitude as that of the gamma ray. The optimal scattering angle that allows determination of the direction of the incoming gamma ray is a complex function of the energy of the incoming gamma ray, the energy and spatial resolutions of the detectors and the stopping power of the media. At low energies the optimal angles are around 135° backscattered gamma rays, while at medium and high energies the optimum is around 45° forward angles.

Figure 38:
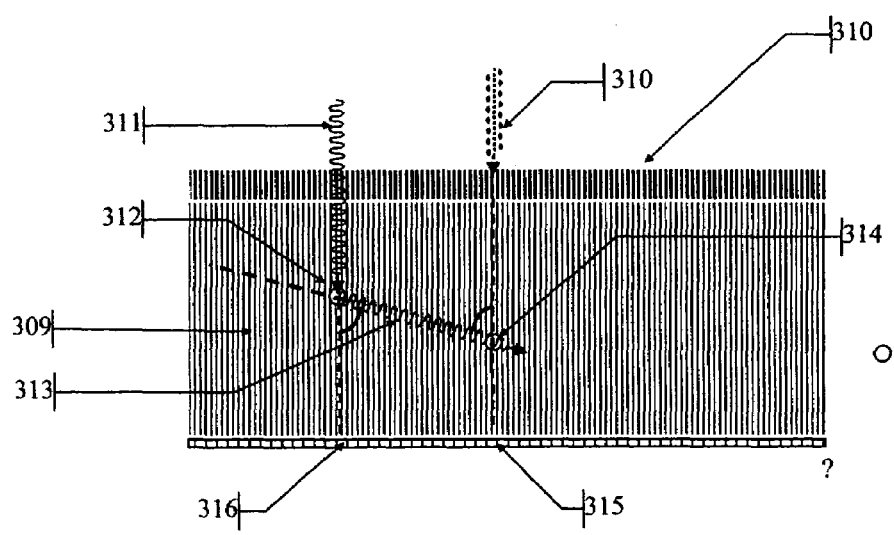
FIG. 38 illustrates a collimated gamma camera composed of an array of fibers and a method for determining the position of the initial Compton scattering

FIG. 38 illustrates the Compton scattering event followed by a Photoelectric event occurring in the scintillator of a gamma camera composed of an array of scintillation fibers 309 which may have the PBCS structure or may also be loosely packed structure of scintillation fibers, having a cross section larger than the effective range of the knocked-off electrons, and guide the scintillation light by critical angle reflection. The PBCS lattice will give better spatial resolutions but is less efficient due to its large holes and more expensive to fabricate. A 10 cm thick array will have an efficiency of ~60% to stop the 140 keV gamma rays through Compton effect interactions. The lateral positions of the two events, 312 and 314 occurring practically simultaneously, is known from the positions, 316 and 315 respectively, of the scintillation fibers on the photo sensor array. The vertical position along the fibers may be found from the "penumbra" around the main fibers as illustrated in FIG. 15. The separate energies of each of the events may be found by integrating the photons exiting each of the fibers and their immediate "penumbra". The question of which of the events 312 or 314 occurred first is resolved by the kinematics of the scattering at low energies, as the maximal energy ($E_e$max) that the incoming gamma ray with energy E can transfer to the electron is given by $E_e$max=[E/(1+511/2E)], showing that up to E=255 keV $E_e$max<127.5 keV. Thus as can be seen from Table 3 for the popular $Tc^{99m}$ radio-pharmaceutical emitting the E=140 keV the maximal energy of the electron $E_e$max=49.561 keV and that of the scattered gamma ray is $E_1$=90,439 keV. Thus the event with the smaller energy is the first.

For higher energy radioisotopes such as the 360 keV of $I^{131}$, looking which of the events is closer to the entry plane resolves the problem which is first as the energy of the scattered gamma ray is given by
$E_1$=511/[1+cos$\theta$+(511/$E_0$)] and for $E_0$=511 keV and cos$\theta$=$_0$ the energy of the scattered gamma ray is $E_1$=511/[1+(511/$E_0$)]=255 keV which is equal to that of the knocked-off electron. Thus limiting the place of entry of the gamma ray with a rough collimator 310 will set the geometry right; the event closer to the plane of the collimator is the back-scattered gamma ray and will have a higher energy than the energy of the knocked-off electron which also points to the direction of entry of the gamma ray. What the collimator does, is in effect limit the "cone ambiguity" to that of the aperture of the septum of the collimator.

As explained above in conjunction with FIG. 36 at low and medium energies it is of extreme importance to maximize the energy of the recoil electron in order to increase the accuracy of assessing its direction. It is also important to minimize ($\partial\theta/\partial E$), the angular variance of the incoming gamma ray as a function of the scattered gamma ray's energy. A good compromise for low energies such as the 140 keV of $Tc^{99m}$ is to detect the gamma rays that are scattered from 90° to 135°, while for medium energies 245 keV to 511 keV one can allow to include a larger portion of the scattered gamma rays, from 45° to 135°.

Figure 19:
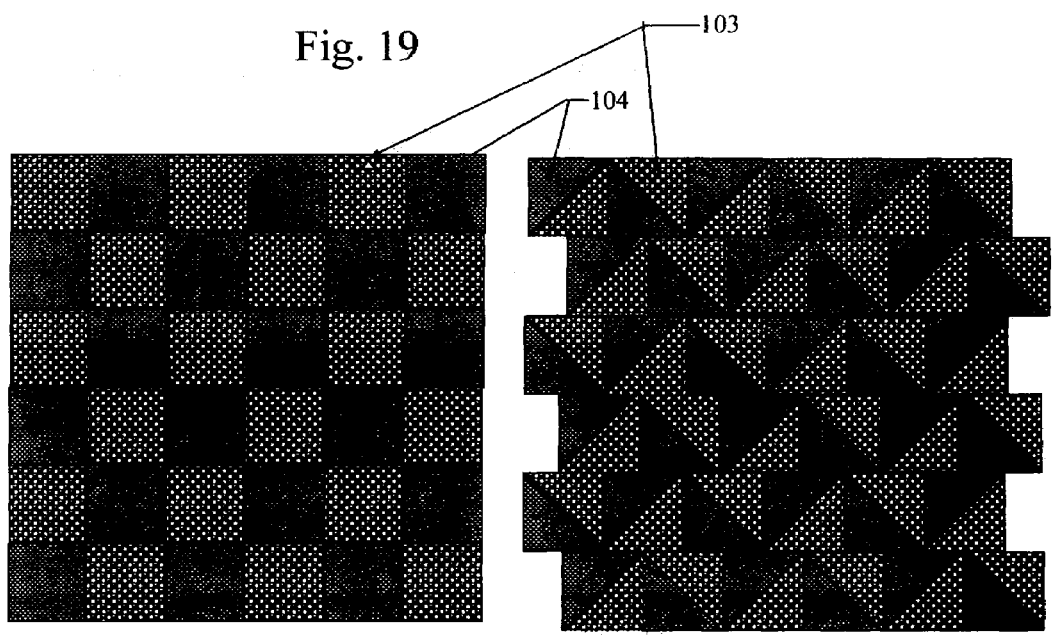
FIG. 19 illustrates a PBCS lattice formed by adjacent "islands" of PBCS scintillators, having adjacent Bandgaps.

As explained above a doped p-terphenyl PBC is the choice for a Compton scatterer. Although a triangular structure of very large holes will give the highest bandgap, the optimal structure is a "honeycomb" of fibers of diameter of ⅓ wavelength of the scintillator or approximately 140 nm, arranged in a periodically recurring open hexagonal geometry where the radius of the hexagon is approximately 410 nm. This geometry will result in a bandgap from 400 nm to 420 nm approximately. A second bandgap may be structured around 430 nm by enlarging the diameters of the fibers to 150 nm and that of the hexagon to 430 nm; this will result in a bandgap from 420 nm to 440 nm approximately. Consequently the PBCS lattices will be structured out of "islands" of hexagons as in FIG. 19 to cover ~75% of the p-terphenyl spectrum from 400 nm to 440 nm. If the dimensions of the islands are 5 lines deep in each direction, the effective spatial resolution will be ~2$\mu$.

Figure 39:
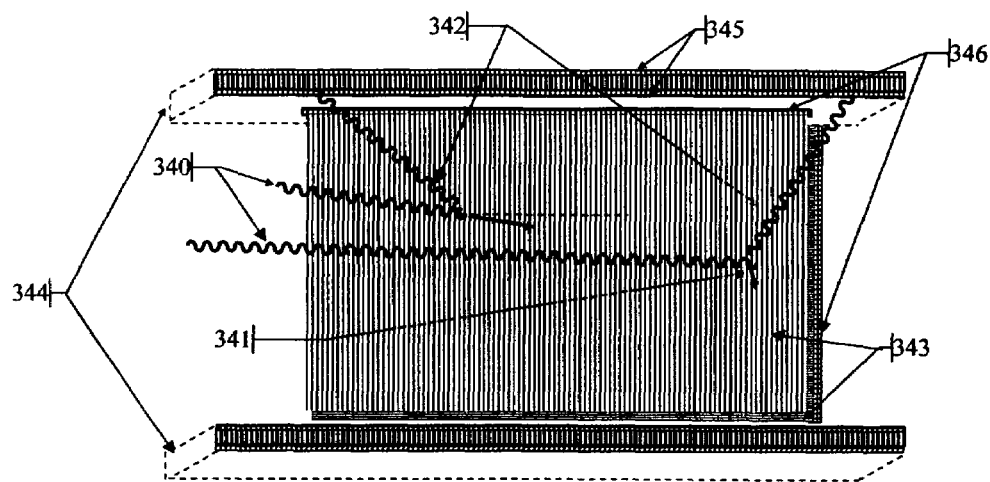
FIGS. 39, 40, 41 and 42 illustrate four different structures of a PBCS Compton cameras
Figure 40:
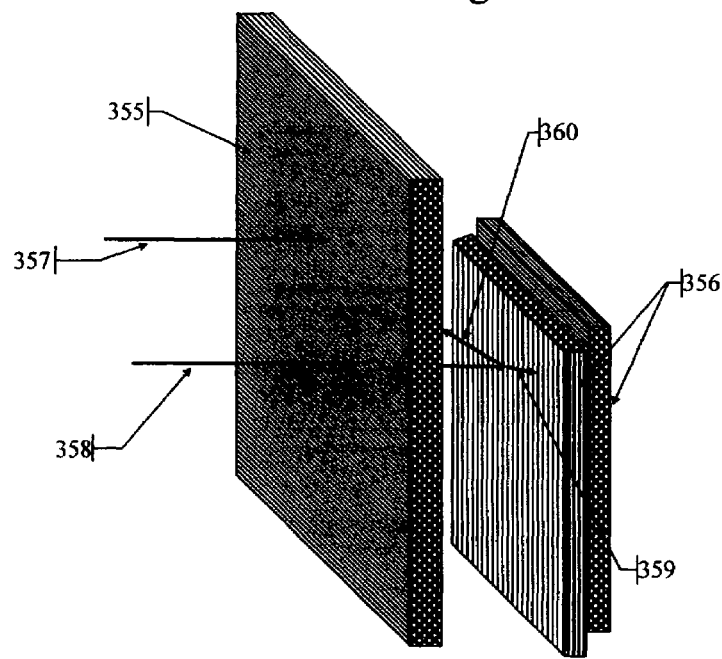

FIG. 39 illustrates a Compton camera with a scatterer structured as a wood-pile of PBCS lattices 343, each such lattice structured out of "islands" where the diameters of the fibers and respective distances change by approximately 10% from one "island" to the other. The preferred depth of the scatterer is 8" deep which will allow 37% absorption of the 140 keV gamma rays. The lateral dimensions depend on the aplication. The Compton scatterer is between two PBCS detector plates 344, above and below it, extending several inches beyond the Compton scatterer in both lateral directions so as to be able to detect the gamma rays back and forth scattered ±45°. The two PBCS detector plates consist of high Z scintillators, preferably of Yttrium Gadolinium Oxide that has a narrow emission spectrum around 611 nm and may be covered with a bandgap of 5%. Photo-electric sensors 345 cover both ends of the PBCS lattices 344 which needs to be only 4 mm thick for 75% efficiency to stop the scattered gamma rays having an energy from 95 keV to 135 keV FIG. 40 illustrates a low energy Compton camera where the scattered gamma detector 355 is in front of the scatterer 356 to detect only back-scattered 360 gamma rays. In this geometry the photoelectric event detector must let pass most of the incoming radiation through it to the scatterer, but be able to fully absorb the back scattered gamma rays 360. As the number of the initially absorbed photo-electric events 357 is much larger than the gamma rays back scattered from the Compton scatterer, the dead time of the photo-electric event recorder must be small. The Lanthanum Chlorine Bromide PBCS scintillator with a lifetime of 25 nsec fulfills these requirements.

Table 5 below shows the optimal angles where to measure the energies of the scattered gamma ray and the energy of the recoil electron. The energy resolution of the scattered gamma ray is obtained by the light output of the specific scintillator selected and the quantum efficiency (Q.E.) of the photo-sensors at the peak wavelength of the scintillator (60% at 350-450 nm and 80% at 600 nm). This energy resolution and the angular variance ($\partial\theta/\partial E$) at the given angle, determine the angular variance of the calculated angle $\theta$ of the incoming gamma ray in the "scattering plane". This angular variance is much larger than the geometric angular variance in the direction of the scattered gamma ray, obtained from the spatial resolution of the position of the events divided by the distance between the events. The angular variance in the direction of the recoil electron $\phi$, on the other hand is calculated geometrically given the length of the initial part of its track and the spatial resolution of the PBCS. The initial part of the track was assumed to be 10% of the CSDA length of it, at low energies and 5% at energies higher than 511 keV. The lateral variance in determining the direction of the track was assumed to be ~1$\mu$. While these assumptions are reasonable, their implications at low energies are far reaching. Table 5 shows two alternative choices for measuring the scattered gamma ray at low energies, one at 135° and the other at 80°. Measuring the scattered gamma ray at 135° maximizes the energy of the recoil electron and its range and consequently minimizes the variance of the direction of the recoil electron. Measuring the scattered gamma ray at 80° on the other hand minimizes the angular variance as a function of energy ($\partial\theta/\partial E$), but leaves less energy for the recoil electron which consequently has a shorter range and therefore a larger variance. It is therefore important to empirically find the actual length of the "straight" section of the recoil electron and the slope and variance of the linear best fit, for different energies, in order to find the best range of angles, between 80° and 135° to measure the direction of the recoil electron. The direction of the incoming gamma rays are calculated generating cones, whose apexes is the variance of the calculated angles $[(\Delta\theta)^2+(\Delta\phi)^2]^{1/2}$ and each cone is given a weight in inverse proportion to its variance, before back projecting them to find their intersections in space.

TABLE 4

| $E_0$ | 140*<br>YGO + Plastic | 140^<br>LaBr + Plastic | 186^<br>YGO + Plastic | 239**<br>YGO + Plastic | 375#<br>YGO + Plastic | 511#<br>YGO + LaBr |
|---|---|---|---|---|---|---|
| $E_{sc} \pm \sigma$ keV | 95.38 ± 1.54 | 112 ± 1.5 | 143 ± 1.9 | 193.7 ± 2.2 | 308.6 ± 2.02 | 395 ± 3.1 |
| °/keV | 4.3° | 2.27° | 1.43° | .9° | 0.43° | 0.32 |
| $E_e \pm \sigma$ keV | 44.6 ± 1.65 | 28 ± 1.3 | 43 ± 1.65 | 45.3 ± 1.68 | 66.4 ± 2.0 | 116 ± 1.55 |
| $E_0$ keV | 140 ± 2.2 | 140 ± 2 | 186 ± 2.5 | 239 ± 2.8 | 375 ± 2.9 | 511 ± 3.5 |
| $\sigma\theta_E$ | 135 ± 9.6 | 80 ± 3.4 | 80 ± 3.6 | 60 ± 2.5° | 45 ± 1.2 | 45 ± 1.1 |
| e⁻ track | 169μ | 75μ | 159μ | 174μ | 338μ | 332μ |
| 10% R | 3.3° | 7.6° | 3.6° | 3.4° | 1.7° | 1.7° |
| 5% R | | | | | | |

| $E_0$ | 583#<br>YGO + LaBr | 662#<br>YGO + LaBr | 769#<br>YGO + LaBr | 1001#<br>YGO + LaBr | 1461#<br>YGO + LaBr | 2614#<br>YGO + LaBr |
|---|---|---|---|---|---|---|
| $E_{sc} \pm \sigma$ keV | 437 ± 3.3 | 479.8 ± 3.5 | 534 ± 3.66 | 636 ± 4 | 795 ± 4.5 | 1045 ± 5.1 |
| °/keV | 0.25 | 0.14 | 0.14 | 0.1 | 0.07 | 0.04 |
| $E_e \pm \sigma$ keV | 146 ± 1.7 | 182 ± 1.9 | 235 ± 2.2 | 365 ± 2.8 | 666 ± 3.7 | 1569 ± 5.7 |
| $E_0$ keV | 583 ± 37 | 662 ± 4 | 769 ± 4.3 | 1001 ± 4.9 | 1461 ± 5.9 | 2614 ± 7.7 |
| $\sigma\theta_E$ | 45 ± .9 | 5 ± 0.6 | 45 ± 0.6 | 45 ± 0.5 | 45 ± .5° | 45 ± .5° |
| e⁻ track | 480μ | 679μ | 1009μ | 1923μ | 4329μ | 11,824μ |
| 10% R | | | | | | |
| 5% R | 2.4° | 1.6° | 1.2° | 0.6° | .3° | 0.3° |

*at 135°;
^at 80°;
**at 60°;
at 45°

One has to note that although the detection of the incoming gamma rays is determined at preferred angles, nothing excludes the detection of Photoelectric events of the same total energy and their inclusion in the statistics, for the purpose of measuring the intensity of the source. Thus a relatively a few events are needed that through back-projection can determine the location of the source, while the intensity of the source may be assessed by the bulk of the events scattered at all angles.

Figure 41:
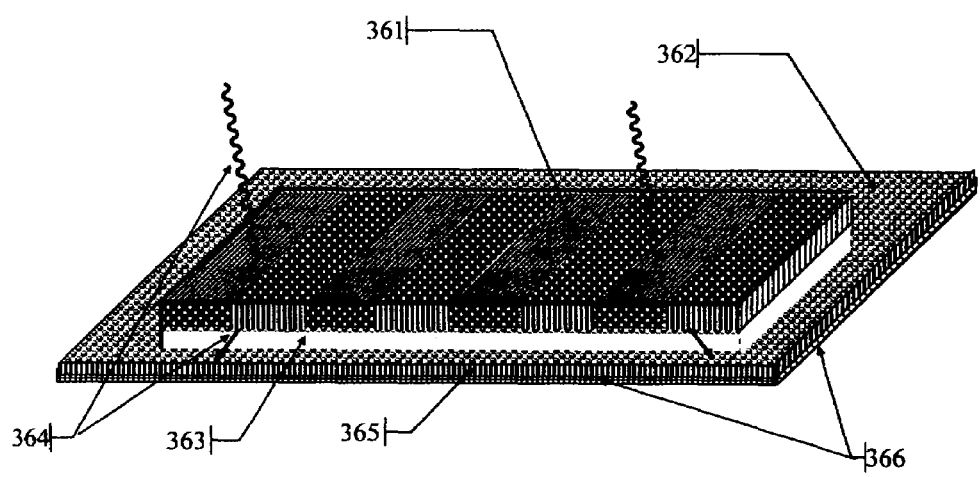

FIG. 41 illustrates a medium and higher energy Compton camera which consists of a PBCS Compton scatterer structured as a wood-pile of mutually orthogonal lattices 361 preferably a Lanthanum Chlorine Bromide PBCS which has a medium Z, and backed at some distance 363 by a larger, 10 mm thick, 2D PBCS scintillator 362 which serves as the detector for the scattered gamma rays and is preferably a high Z scintillator such as Yttrium Gadolinium Oxide that has a narrow spectrum at 61 mm. The lattices of the Lanthanum Chlorine Bromide PBCS scatterer have at one of their ends photo sensor arrays and the Yttrium Gadolinium Oxide detector has across its base a large array of photosensors 366. Medium energy, for example 511 keV, Gamma rays impinging on the Compton scatterer are scattered into all 47 directions; the larger photo-electric event detector 362 subtends approximately 3π/2 solid angle, however taking in account the preponderance of forward scattering, approximately 50% of the scattered gamma rays will reach the photo-electric event detector 362 and be detected, given its high detection efficiency. Table 4 below shows the energies of the scattered gamma rays and the recoil electrons for incoming 511 keV gamma rays, illustrating that the recoil electrons have sufficient energy down to 45° scattering, to have their initial part of their track substantially straight.

TABLE 5

| $E\gamma 0 = 511$ keV $\alpha = 1$ | $\theta = 180°$ | $\theta = 160°$ | $\theta = 135°$ | $\theta = 90°$ | $\theta = 89°$ | $\theta = 85°$ | $\theta = 45°$ | $\theta = 5°$ | $\theta = 0°$ |
|---|---|---|---|---|---|---|---|---|---|
| $E\gamma 1 = E_0/[1 + \alpha(1 - \cos\theta)]$ | 170.33 | 173.827 | 195.69 | 255 | 257.75 | 267.15 | 395.24 | 509.21 | 511 |
| $\phi \cot\phi = (1 + \alpha)\tan\theta/2$ | 0° | 5° | 11.5° | 26° | 27° | 28.5° | 51.5° | 85° | 90° |
| $E_e = E_0 - E_1$ keV | 340.77 | 347.654 | 315.31 | 255 | 253.25 | 243.85 | 115.79 | 1.79 | 0 keV |

Figure 42:
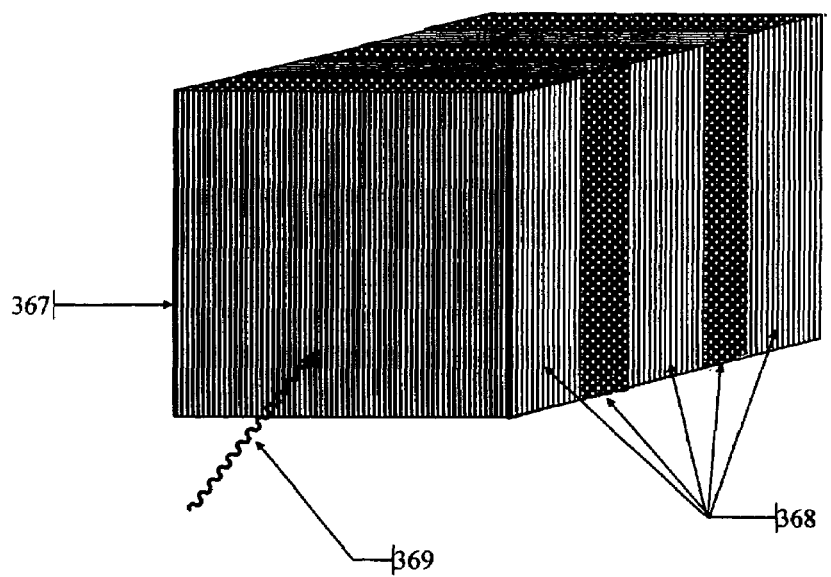

FIG. 42 illustrates a PBCS Compton+Pair camera 367 for high energies, of 1 Mev and up, structured as a wood-pile of mutually orthogonal lattices 368, where both the initial scattering and the following lower energy events have a high probability to occur in the same volume. For 1 Mev gamma rays the total probability to be absorbed in a [10"×10"×10"] PBCS camera of LaBr₃, is around 75% where 95% of it will be through the Compton effect. The subsequent, scattered lower energy gamma rays will have a distribution of probabilities to be Compton scattered again, or absorbed through a photoelectric effect. The secondary Compton scattered gamma rays will again be further scattered or absorbed. Thus multiple cascades of 2, 3, 4 or more simultaneous events, will develop that can be identified by the positions and directions of the knocked-off electrons and respective time coincidences, enabling the identification of the primary gamma ray and its direction. Obviously the variances for each event of the cascade are cumulative, albeit small at high energies.

Figure 43:
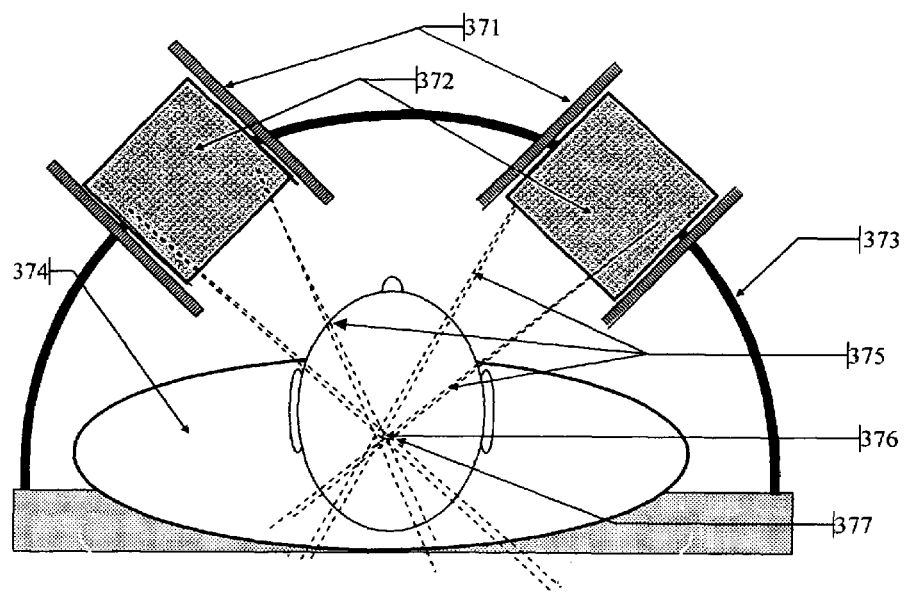
FIG. 43 illustrates a SPECT tomograph composed of two rotating PBC Compton Cameras

FIG. 43 illustrates a Single Photon Emission Computerized Tomograph (SPECT) using two low energy PBCSl Compton cameras substantially as described above in conjunction with FIG. 39. The cameras may be static or rotating on a gantry 372 around the patient 373, to better average the variances of the calculated directions of the incoming gamma rays. Table 6 below gives an indication of the dimensions of the Compton scatterers 370 which for low energies consists preferably of a woodpile of PBCS lattices of doped p-terphenyl and the photoelectric event detectors 371 which preferably consist of a single PBCS Yttrium Gadolinium Oxide lattice. Getting rid of the regular straight hole collimator as in legacy gamma cameras, increases the efficiency by a factor of $10^4$. On the other hand the absorption efficiency of an 8" thick p-terphenyl absorber is only 63% as compared simultaneous annihilation 511 keV gamma rays. that give only a line crossing the source up to an uncertainty of the mean free path of the positron.

The PBCS radiation detectors may be viewed as virtually pixellated detectors having any desired thickness to fully absorb Gamma or X-rays, with a spatial resolution down to $(1\mu)^3$ without any separating walls. Thus they are not limited by the sizes and thicknesses needed to detect a spectrum of radiations from x-rays to high energy gamma rays. Although the high spatial resolution is substantially independent of the scintillator material, the overall thicknesses of PBCS arrays, determining their absorption efficiency of the radiation, is obviously a function of their effective atomic number Z.

TABLE 6

|  |  | 26% p-terphenyl (d/a) = 0.9 ρ = 0.32 exc. energy 71 eV | 26% LaBr$_3$ (d/a) = 0.9 ρ = 1.38 382 eV | 26% YGO (d/a) = 0.9 ρ = 1.83 619 eV |
|---|---|---|---|---|
| 90 keV | Total attenuation coefficient μ/ρ | 0.165 cm$^2$/g | 1.72 cm$^2$/g | 3.63 cm$^2$/g |
|  | Photo-electric ratio | 0.91% | 88% | 93% |
|  | 63% absorption | 19 cm | 0.421 cm | 0.15 cm |
| 140 keV | Total attenuation coefficient μ/ρ | 0.146 cm$^2$/g | 0.58 cm$^2$/g | 1.17 cm$^2$/g |
|  | Photo-electric ratio | 0.267% | 74% | 85% |
|  | 63% absorption | 21.5 cm | 1.25 cm | 0.45 cm |
| 511 keV | Total attenuation coefficient μ/ρ | 0.0916 cm$^2$/g | 0.0895 cm$^2$/g | 0.107 cm$^2$/g |
|  | Photo-electric ratio | 6.5 10$^{-5}$ | 13.5% | 28.5% |
|  | 63% absorption | 34.1 cm | 8.09 cm | 4.9 cm | with 82% for (3/8)" NaI(Tl) crystal, for the Tc$^{99m}$ 140 keV gamma ray. The constraint of counting only gamma rays scattered between 80° and 135° compounded by the smaller solid angle covered by the Yttrium Gadolinium Oxide detectors 371, reduces the overall efficiency by a factor of $10^2$ leaving still an improvement factor of approximately $10^2$.

Figure 44:
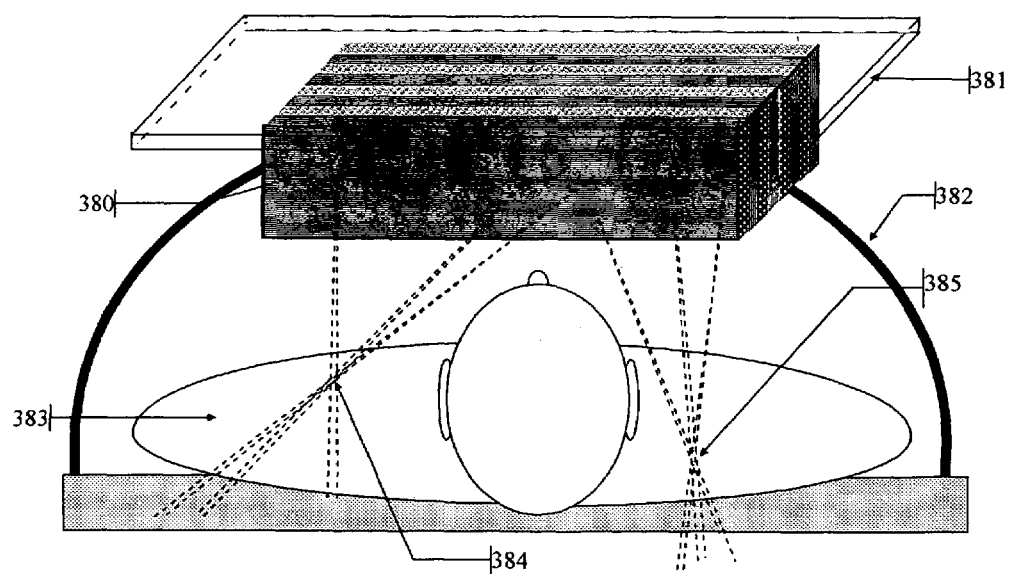
FIG. 44 illustrates a tomographic camera using a large PBCS Compton Camera

FIG. 44 illustrates the tomographic capabilities of a PBCS Compton camera for moderate energies as illustrated in FIG. 41 and consisting of a wood-pile like 2D lattices 380 of Lanthanum Chlorine Bromide scatterer and a 2D thin PBCS lattice of Yttrium Gadolinium Oxide 382 in order to better position it above the patient 383. The tomographic capabilities of the PBCS Compton camera result from the large angle tended by the camera when positioned very close to the source of radiation. Thus radiations originating from different depths 384, 385 of a patient's body can be located due to the Compton camera's ability to resolve direction with high precision. The Compton camera may be mounted on a circular gantry 382 for better positioning it symetrically above the desired area.

Figure 45:
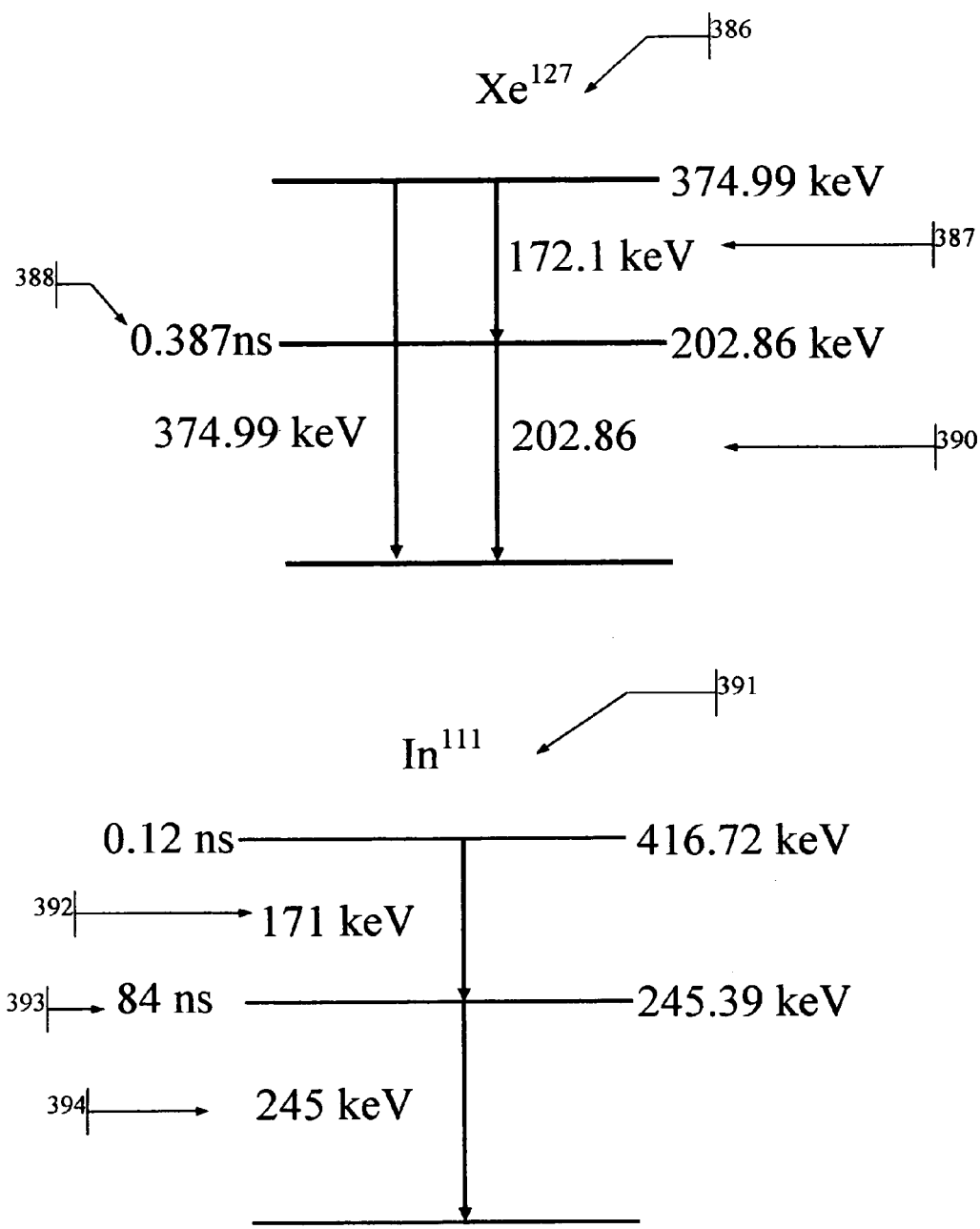
FIG. 45 shows the decay schemes of two radio-isotopes emitting a cascade of two gamma rays suitable for use in a tomographic gamma camera.

A most important corollary of the fact that a PBCS Compton Camera is able to determine the direction of the incoming gamma rays, is that it opens the door to a new tomography modality other than PET. Radio-isotopes emitting a cascade of gamma rays may be used to determine the location of the source. FIG. 45 shows the decay schemes of two radio-isotopes, Xe$^{127}$ and I$^{111}$ emitting a cascade of two gamma rays, suitable for use in a tomographic camera. Xe$^{127}$ emits a cascade of 172 keV followed after 0.387 nanoseconds, which for all practical purposes is simultaneously, a 375 keV gamma ray.

I$^{111}$ emits a 171 keV gamma ray followed after 84 nanoseconds a 245 keV gamma ray. The coincidence between the two gamma rays and the fact that their direction can be determined with the PBCS Compton cameras enables to determine their point of intersection and unequivocally gives the location of the source, unlike the detection of the Thus while for low energies, PBCS arrays consisting of plastic scintillator fibers are the choice, due to their relatively easy manufacturability, at medium and higher energies the scintillator of choice is Yttrium Gadolinium Oxide which currently is not available commercially.

Fast coincidences of the order of 1 nsec, between the outputs of the resolution elements may be used to confirm cascades of events, reject undesired scattering events or spurious background radiation.

An important consequence of the virtual pixellation of the PBCS radiation detector is the immense reduction of the total dead time of the array, as only the scintillation fibers guiding the photons are paralyzed during a scintillation event and unable to detect another simultaneous event. The rest of the array continuous to function normally. For example a 1 Mev gamma ray that after interaction with a half empty PBCS of Yttrium Gadolinium Oxide, produces a 1 mm long track will paralyze only $10^3$ fibers along the track (at 10.5μ fiber every 1μ) multiplied by at most a factor of 20 to account for the "penumbra" around the main fibers, or a total of 2.10$^4$ fibers. Taking in account that there are $10^8$ fibers per cm$^2$ of lateral surface, the number of affected fibers is infinitessimally small. The important consequence of this calculation is that scintillators that have long decay times such as Yttrium Gadolinium Oxide or ZnSe(Te), hitherto considered problematic for radiation detectors, are perfectly acceptable for use in PBCS detectors.

Thus, independently of their use in Compton cameras, PBCS radiation detectors, can replace the current radiation detectors used in different radiation detecting modalities, including Gamma Cameras, PET, CT and Digital Radiography. The direction finding, through the resolution of the "cone ambiguity" in the case of Compton scatterings, is an additional, albeit a very important, bonus.

Figure 46:
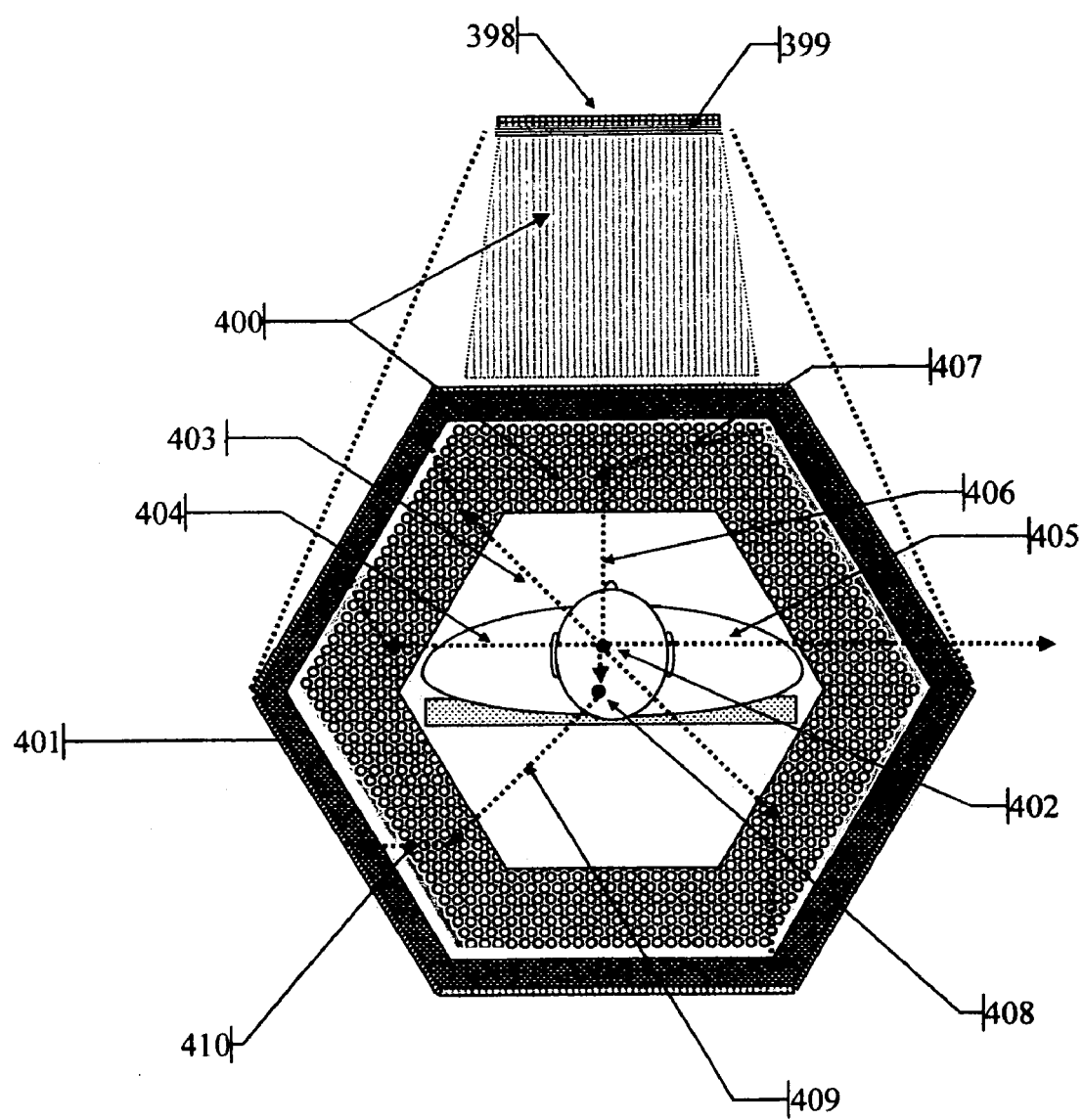
FIG. 46 illustrates an hexagonal PBCS Compton camera suitable for use in PET studies

FIG. 46 illustrates a section of an hexagonal Positron Emission Tomograph (PET) where the 511 keV gamma rays are detected by an array of high resolution PBCS radiation detectors consisting of a wood-pile of lattices of tubular scintillators 400. The criss-crossed PBCS lattices terminating with photo sensors 398, 399 enable, as explained above, to find the positions in 3D of the 511 keV gamma rays hitting the array, with micron accuracy. If used to detect only the coincident 511 keV gamma rays, the scintillators of choice are Yttrium Gadolinium Oxide or ZnSe(Te). The use of the PBCS radiation detectors will improve the determination of the virtual line connecting between the opposite and coincident events, due to the ability to determine the beginning of the electron track following the absorption of the 511 keV gamma rays with micron accuracy. This very high spatial resolution, enables to reduce the size of a PET as the distance between the opposite detectors can be reduced substantially, for example when used for "head" studies.

FIG. 46 illustrates the use of the PBCS Compton camera structure in a PET, with two PBCS detectors, one for Compton scattering the 511 keV gamma ray and the second for detecting the scattered lower energy gamma rays. In this case the scintillator of choice for the Compton scatterer 400 is Lanthanum Chlorine Bromide and the scintillator of choice for detecting the scattered gamma rays is Yttrium Gadolinium Oxide 401. The PBCS Compton camera structure, has additional benefits, in addition to those the high spatial resolution, as explained above, entails.

The ability of the PBCS Compton cameras to determine the direction of the gamma rays independently, serves to confirm the direction obtained by two opposite voxels at 180° each 403, and reject spurious events caused by scattering. PBCS Compton cameras may also confirm the direction of the original source, in case of a single scattering, where only one detector detects a 511 keV gamma ray 404 and the second 511 keV gamma rays escapes detection 405.

The important additional benefit that the PBCS Compton camera structure brings to a PET is the ability to use other radio-pharmaceuticals emitting a cascade of two or more gamma rays, in addition to positron emitters, as explained above in conjunction with FIG. 45. Detecting two gamma rays that do not have to be emitted opposite each of the other, and find the location of their source is an important development in Tomography.

Figure 47:
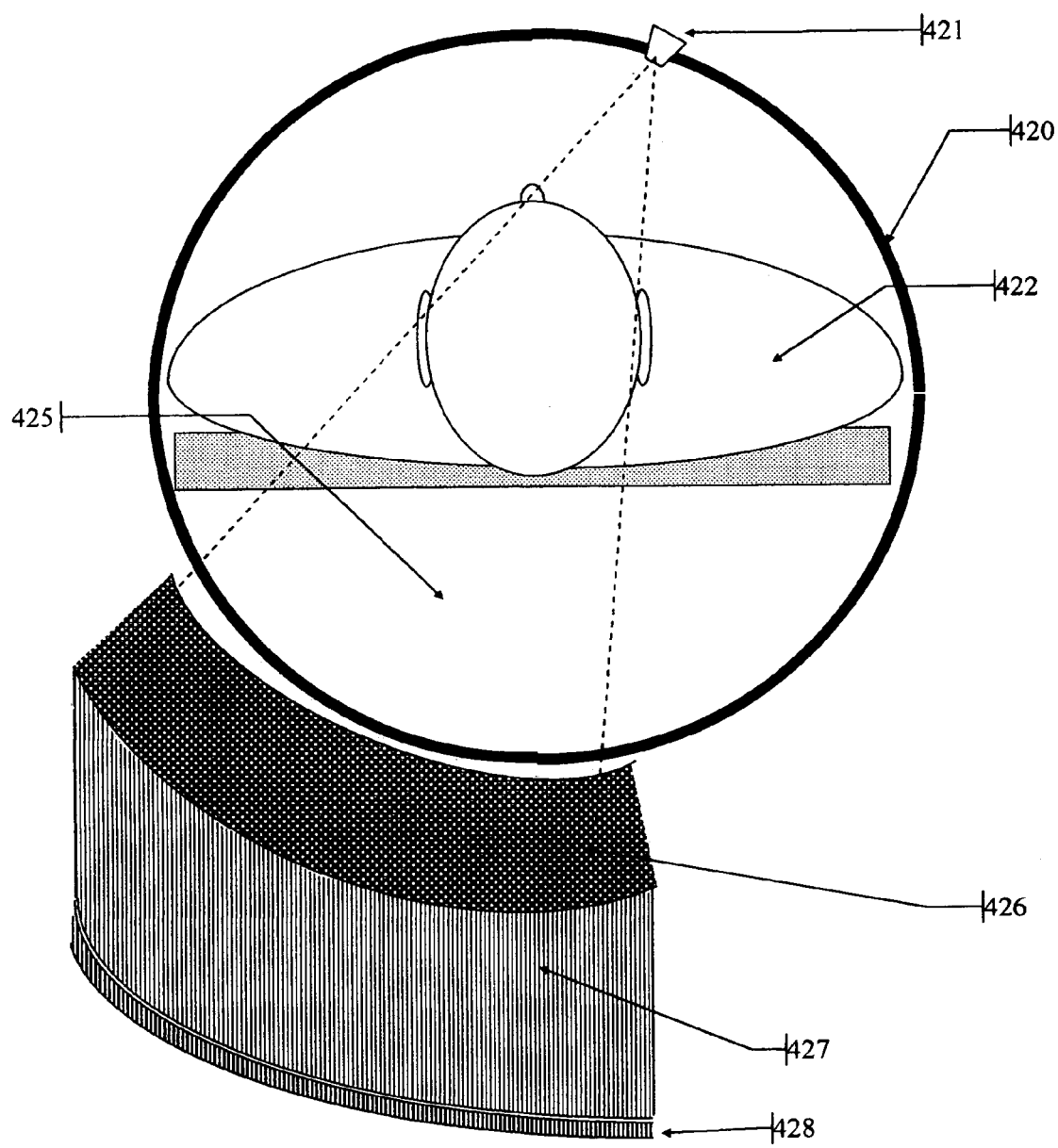
FIG. 47 illustrates a PBCS radiation detector used in a multi-slice detector in a CT.

FIG. 47 illustrates a CT scanner where the X-rays emitted by a rotating X-ray tube 421 traverse the body of the patient 422 and are detected by a PBCS radiation detector which may be straight or curved 426 covering the 3D fan beam 425 generated by the X-ray source. The detector structure is deep enough 427 to cover several contiguous slices of the scanned body irradiated by the X-ray source. The X-ray tube and the PBCS detector rotate together around a circular gantry 420. The PBCS radiation detector consists of criss-crossed lattices of Yttrium Gadolinium Oxide each 2-3μ thick and a total thickness of 6 mm, allowing to absorb 95% of X-ray radiation at 150 keV. One end of each of the fiber lattices 427 is covered with photo-electric sensors 428. The PCBS array enjoys all the advantages of virtual pixellation without physical walls, total absorption and spatial resolution of several microns, as explained above in conjunction with FIG. 46.

Figure 48:
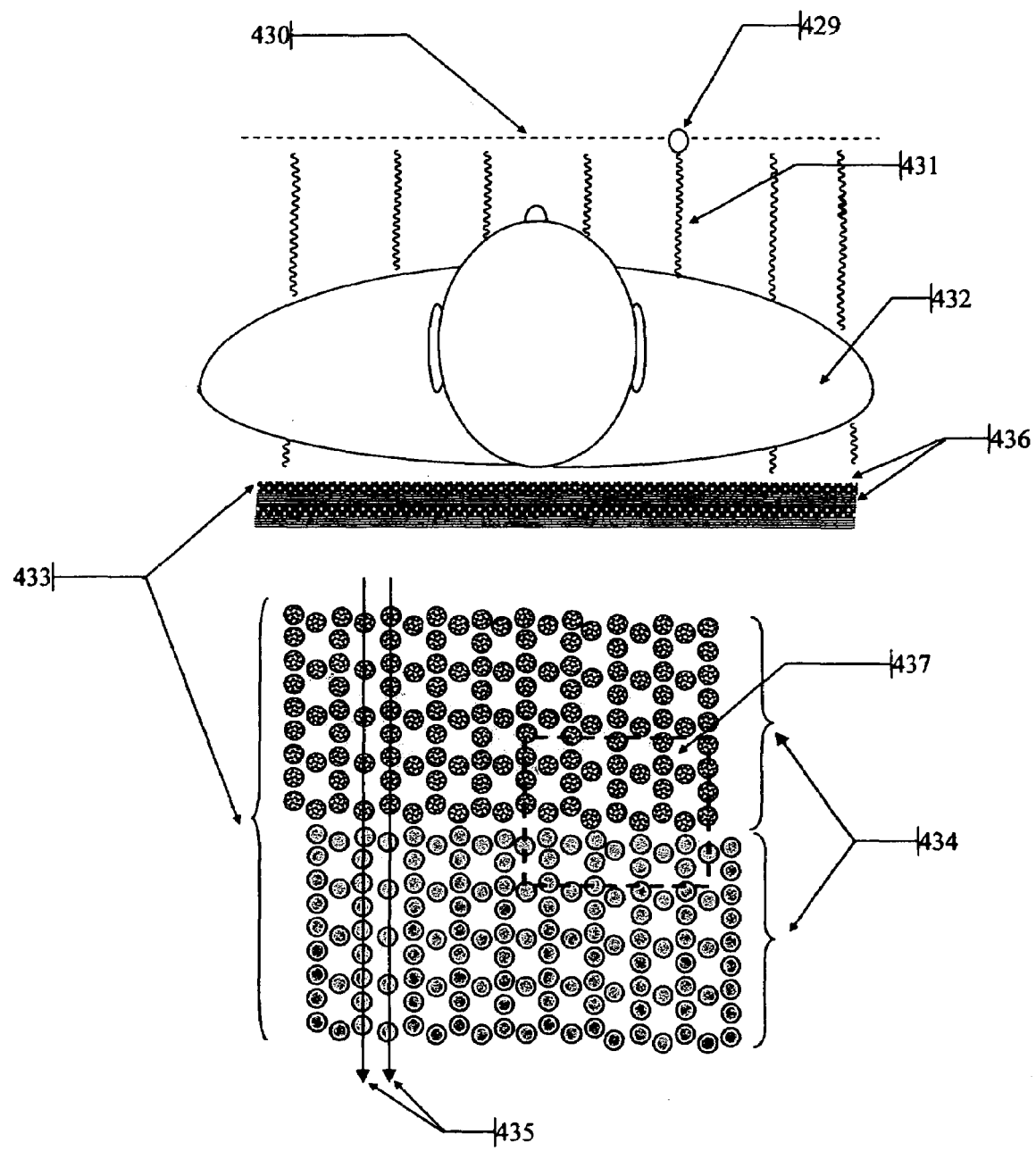
FIG. 48 illustrates an ultra-high resolution PBCS array used to detect X-rays traversing the body in a digital radiography system

FIG. 48 illustrates a digital radiography system using a 60-130 keV X-ray tube 429 traveling linearly 430 along a line and scanning the desired region of the patient 432 and a PBCS radiation detector as explained above, for detecting the radiation traversing the patient and thus imaging the absorption of the different organs in the body. The PBCS radiation detector 436 consists of criss-crossed lattices 433 of Yttrium Gadolinium Oxide, each 2.5μ thick and a total thickness of 5 mm, allowing to absorb 95% of the X-rays. The lattices 433 containing fiber layers arranged in a "honeycomb" like geometry, present towards the incoming X-ray radiation non-uniform paths, layers are staggered 434, so that incoming X-rays encounter the same number of fibers 435 when traversing a lattice. 2000 criss-crossed lattices, each 6 hexagonal units thick equaling 2.5μ have a total thickness of 5 mm and may extend up to 10"×10" in the lateral direction. The space between the fibers is empty or may be filled with aerogels. The advantage of the PBCS structures is the exquisite spatial resolutions of the order of 2.5μ attained as compared to 50μ (20 line pairs/mm) with the best current technology. It is noteworthy to note that, as the PBCS technology is able to identify the beginning of an electron track, as explained above, the range of the emitted K-photoelectron following a photo-electric absorption, does not represent the ultimate attainable resolution, as is the case with the current legacy technology.

Figure 49:
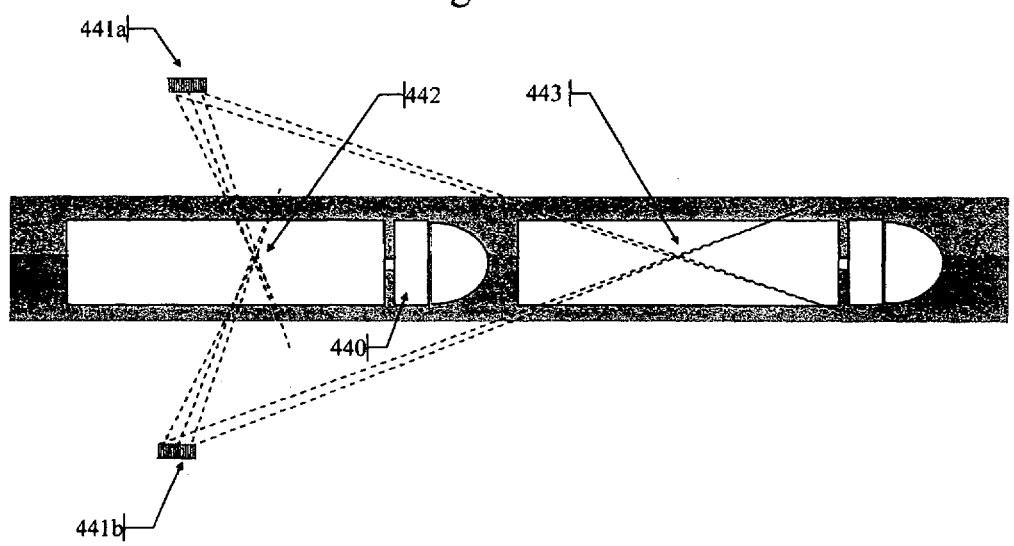
FIG. 49 illustrates a pair of PBCS Compton cameras for detecting moving gamma sources.
Figure 49:
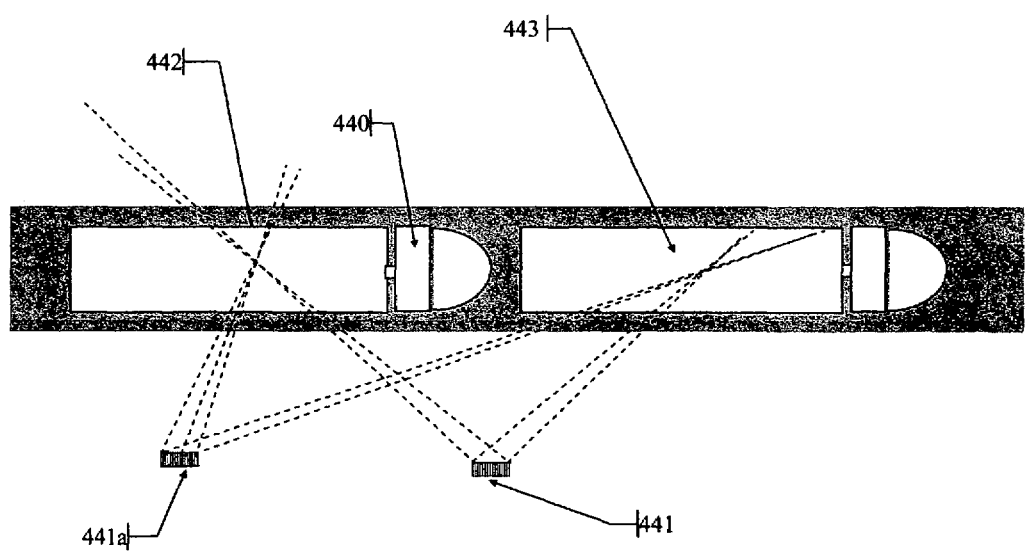

FIG. 49 illustrates the use of one or more PBCS Compton cameras 441a and 441b as stationary tomographic gamma detectors for detecting the position of a moving gamma emitter, for example a gamma emitter transported in a vehicle 440. In this application as the energies expected to be detected are medium to high, the Compton cameras of choice are either the Lanthanum Chloride Bromide Compton scatterer backed by a Yttrium Gadolinium Oxide photoelectric detector described in conjunction with FIG. 41, or the single block Lanthanum Chloride Bromide that detects multiple cascades.

The method consists in taking consecutive radiation maps of the scene, for all possible energies, at high spatial resolution by finding the intersection points of the direction rays and observing if there is a continuity of such intersection points. The odds that background, caused by cosmic rays for example, will show a continuous path in time is infinitessimally small.

Dynamic imaging at high frame rates using two Compton cameras, whether at two sides of a road 441a and 441b or on the same side of a road 441a and 441 at a distance apart, is a very powerful method for locating a low intensity radiation source 442 in a moving vehicle 440 amid high background. Two Compton cameras with very high directional resolution will locate the radiation source 442 with high confidence, with even a small number of events as it is sufficient for only two events, for finding the intersection of their directions. A high directional resolution of 1°-2° which is achievable, means that two intersecting directions will determine the location of a radiation source at a 5 m distance with a 10-20 cm accuracy. For example if a container truck is to be screened and it is moving slowly at 10 km/hr or 3 m/sec, past the inspection point, recording a radiation map of the scene every second means recording a map every 3 m. A shielded radiation source emitting $4.10^3$ gamma rays a second and moving past a 12"×12"×12" PBCS camera at an average distance of 5 m will register 1 event/second or 5 events while moving for 15 m past the Compton camera. Following the continuous movement of the vehicle between two points 442 to 443 for 15 m will detect the 5 events and locate their source with great confidence. Establishing that the intersection spot is moving at approximately the same speed as that of the vehicle, eliminates all possible background.

The high spatial resolution will be able to differentiate between a concentrated source of radiation and merchandise with naturally occurring radioactivity, evenly distributed across the truck.

Figure 50:
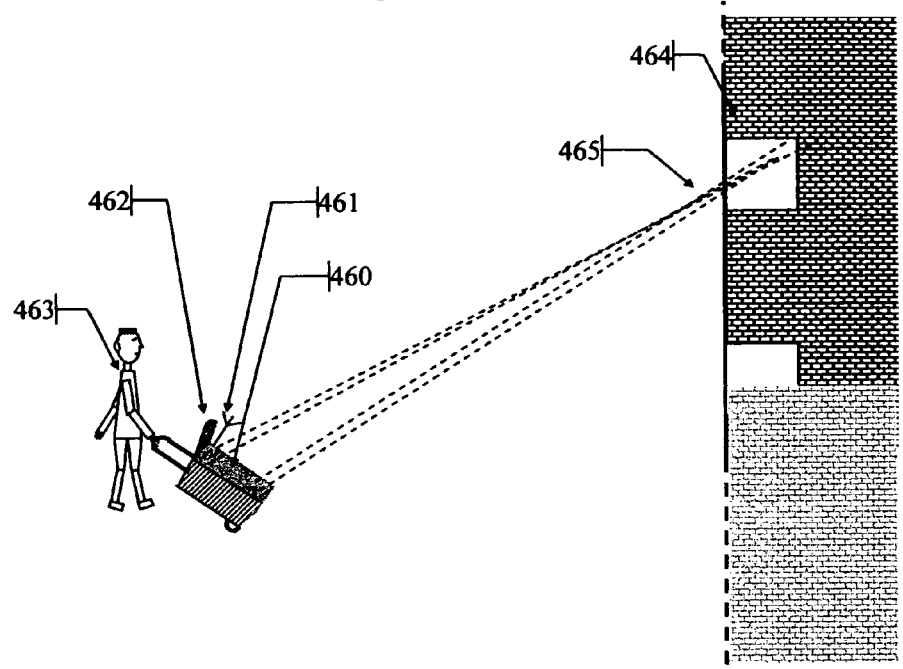
FIG. 50 illustrates the use of mobile PBCS Compton cameras to locate stationary gamma sources
Figure 50:
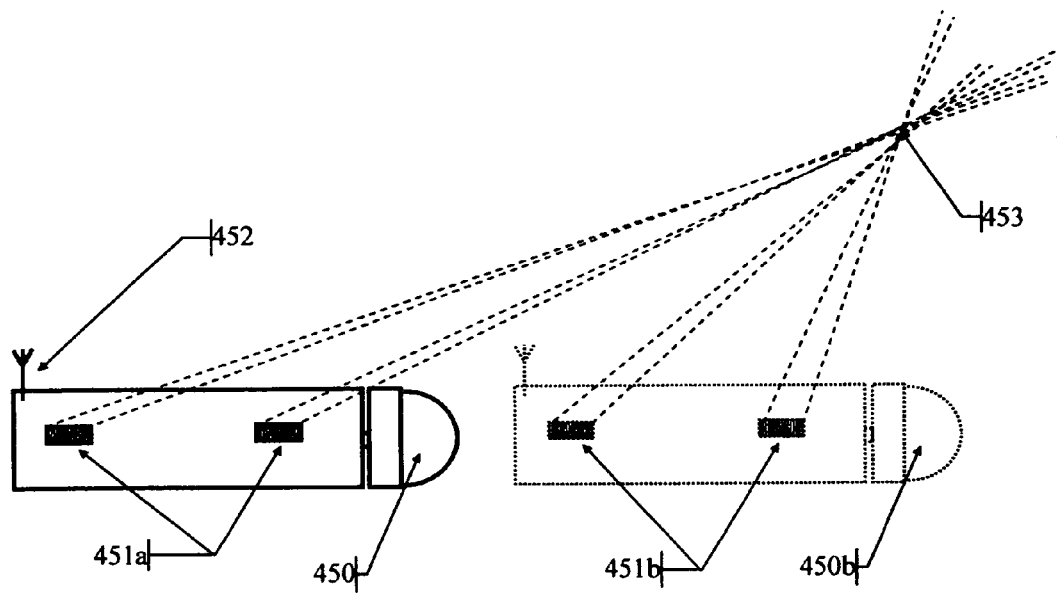

FIG. 50 illustrates the reverse situation, where the radiation source is stationary and the Compton cameras move around. In this situation too cosmic ray background is eliminated as it comes from different places while the Compton camera moves. However as all stationary sources behave similarly the only way is moving around and locating sources of radiation which are not random. A roving Compton camera 460 on a push cart whose position is known through GPS 461 or otherwise, may display on a LCD monitor 462, the local map and on it the intersection points of the directions of incoming gamma rays, that hit a large compton camera. Moving the Compton camera around in the direction of increasing intensity will enable to locate the source.

Two Compton cameras 451*a* mounted a maximal distance apart on a roving vehicle 450 function in the same manner as the pushcart, with the difference that two cameras, say 20' apart, are able to determine location better.

In this mode of operation too, moving radiation sources may be identified and differentiated from stationary sources and background radiation, by looking at a continuity of the path.

There are multiple ways to realize the invention explained above, combine the differentiating features illustrated in the accompanying figures, and devise new embodiments of the method described, without departing from the scope and spirit of the present invention. Those skilled in the art will recognize that other embodiments and modifications are possible. While the invention has been described with respect to the preferred embodiments thereof, it will be understood by those skilled in the art that changes may be made in the above constructions and in the foregoing sequences of operation without departing substantially from the scope and spirit of the invention. All such changes, combinations, modifications and variations are intended to be included herein within the scope of the present invention, as defined by the claims. It is accordingly intended that all matter contained in the above description or shown in the accompanying figures be interpreted as illustrative rather than in a limiting sense.

I claim:

1. A radiation imaging system consisting of one of group comprising a Compton camera, a Gamma Camera, a SPECT, a PET, a CT and a Digital Radiography system wherein said radiation imaging system includes radiation detectors for detecting ionizing radiation wherein, said radiation detectors comprise a plurality of adjacent non-touching Photonic Bandgap Crystal lattices, wherein, each said lattice consists of matrix of first material containing non-touching vertical tubular elements of a second material wherein said second material has different refractive index than the first material and wherein, said tubular elements are organized in periodically recurring geometrical structures formed by no more than 5 tubular elements, wherein said periodicity is across the lateral plane perpendicular to the direction of the tubular elements of the lattice, wherein the first and second materials are selected from a group comprising, scintillator materials and non-scintillating materials transparent to scintillation wavelengths and having a refractive index smaller than 1.2, and wherein, a the distance between the non-touching vertical tubular elements, and b the distance between the non-touching lattices and c the diameters of the vertical tubular elements are less than the wavelengths of the scintillation light, wherein said a distances between the non-touching vertical tubular elements, and b diameters of the vertical tubular elements and c distances between the non-touching lattices and d the refractive index contrast between the first material and the second material are selected in a manner that maximizes the amount of scintillation light is inhibited to propagate laterally across the periodical groups of tubular elements of the lattice and wherein at least one of the edges of the lattices normal to the direction of the tubular elements is covered by a multiplicity of photo-electric sensors sensitive to the wavelengths of the scintillator and wherein the edges of the lattices not covered by photo-sensors are coated with materials reflective to the wavelength of the scintillator and wherein the position of a scintillation along the direction normal to lateral periodicity plane, where an ionizing radiation caused said scintillation, is determined by the shape of the distribution of the intensity of scintillation light, exiting the non-coated edges of the lattices from the region around the tubular scintillator where the ionizing radiation caused said scintillation, wherein said photo-electric sensors connect to electronic circuits that measure the intensity, timing and lateral distribution of electrical signals generated by said sensors.

2. A radiation imaging system as in claim 1 wherein the periodically recurring geometrical structures of tubular elements are selected from a group comprising triangular and open hexagonal geometries and wherein the periodically recurring groups of tubular elements are further grouped in sets of groups consisting of less than 25 groups of tubular elements wherein the diameters of said tubular elements and the distances between them in a set of groups change periodically wherein said changes further maximize the scintillation light that propagates along the direction of the tubular elements.

3. A radiation imaging system as in claim 1 wherein the periodically recurring tubular elements consist of holes in a scintillator matrix filled with air wherein said tubular elements are arranged as triangular lattice having a two dimensional periodically and wherein said tubular elements have diameters larger than 80% of the distance between them.

4. A radiation detector as in claim 1 wherein the tubular elements consist of scintillators in a matrix filled with one of a group comprising aerogels, xerogels and air, wherein said scintillators are coated with materials of higher refractive index.

5. A radiation detector as in claim 1 wherein light of lower wavelength is pumped onto the tubular scintillators thus amplifying the scintillator light by stimulated emission.

6. A radiation detector as in claim 1 where in the tubular scintillators are coupled to light guides of the same diameter wherein said light guides are doped with the same activator material as the scintillator, and wherein light of lower wavelength pumped onto said light guides, amplifies the scintillator light passing through said light guides by stimulated emission.

7. A radiation imaging system as in claim 1 wherein the sequential adjacent lattices of the radiation detectors, have mutually orthogonal planes of periodicity.

8. A radiation imaging system as in claim 1 wherein the position of a scintillation along a tubular scintillator where an ionizing radiation caused scintillation, is determined by comparison between the respective lateral distributions of the intensity of scintillation light exiting from the tubular scintillators of two adjacent mutually orthogonal lattices, in proximity to said tubular scintillator.

9. A Compton camera radiation imaging system as in claim 1 wherein the position of a source of gamma rays in 3D is determined by determining the coordinates of the beginning of the tracks caused by two ionizing events occurring in rapid sequence in one or more different radiation detectors by measuring the coordinates of the beginning of the tracks caused by two ionizing events occurring in rapid sequence in one or more different radiation detectors by measuring the coordinates of each scintillation even, by comparing the respective lateral distributions of the intensities of scintillation light exiting from the tubular scintillators of two adjacent and mutually orthogonal lattices, in proximity to the tubular scintillator where the ionizing radiation caused a scintillation, and by finding the best fit of said measured coordinates to a straight line, derived by minimizing the aggregate distance of the measured coordinates of the scintillations in a multiplicity of tubular scintillators in close proximity to such line and wherein the beginning of a track and its direction are determined to be the beginning and the direction of said best fitting straight line respectively and wherein the energy of an ionizing event is obtained by adding the signals exiting all the tubular elements in close proximity and wherein the direction of a Compton scattered gamma ray is found from the energies, positions and directions of the tracks of sequential events in coincidence wherein the direction of the source of gamma rays is determined by selecting events resulting from scattering at angles where the sum, of the variance of the direction of the recoil electrons and the correlated variance of the energy of the scattered gamma ray, is minimized, wherein said angle is a function of the energy of the primary gamma ray wherein the position in 3D of a gamma ray emitting source is determined by the intersection of the directions of the primary gamma rays interacting with the radiation detectors.

10. A SPECT radiation imaging system as in claim 9 comprising two Compton cameras wherein said Compton cameras are positioned to view the source of radiation at 90° angle between them wherein the location of the gamma emitting source is determined by the intersection of the directions of the primary gamma rays detected by any of the two Compton Cameras when stationary, and wherein said pair of Compton cameras can rotate on a circumference around the source of the gamma emitting source.

11. A PET radiation imaging system as in claim 9 consisting of a multiplicity of Compton cameras wherein said multiple Compton cameras cover only a 180° sector in face of a positron source wherein said Compton cameras establish the direction of the positron source by determining the direction of a single 511 keV gamma ray and wherein said Compton cameras can establish the location of radio-pharmaceuticals emitting gamma rays in a time sequence by determining the direction of gamma rays of the desired energy detected in a predetermined time sequence.

12. A radiation imaging system consisting of one of a group comprising a Compton camera, a Gamma Camera, a SPECT, a PET, a CT and Digital Radiography wherein said radiation imaging system includes radiation detectors for detecting ionizing radiation wherein, said radiation detectors comprise a multiplicity of adjacent layers of tubular scintillator elements wherein each said layer consists of straight tubular scintillator elements of a diameter of less than 100 microns wherein said tubular scintillator elements are laid side by side in a matrix having a refraction index of less than 1.2 wherein the distance between adjacent tubular scintillator elements is more than the wavelength of the scintillator wherein the space between adjacent tubular scintillator elements is filled with a material having a refraction index of less than 1.2 wherein at least one of the edges of the layer normal to the direction of the tubular scintillator elements is covered by a multiplicity of photo-electric sensors sensitive to the wavelengths of the scintillator and wherein the edges of the layers not covered by photo-sensors are coated with materials reflective to the wavelengths of the scintillator and wherein said photo-electric sensors connect to electronic circuits that measure the intensity, timing and lateral distribution of electrical signals generated by said sensors wherein, the position of a scintillation along a tubular scintillator elements, where an ionizing radiation caused said scintillation, is determined by the shape of the distribution of the intensity of scintillation light, exiting the non-coated edges of the lattices from proximal region around the tubular scintillator element.

13. A radiation imaging system as in claim 12 wherein adjacent layers are mutually orthogonal.

14. a radiation imaging system as in claim 12 wherein said tubular scintillator elements are surrounded with a plurality of transparent material layers that increase the amount of scintillation light propagating along the tubular scintillator element.

15. A radiation imaging system as in claim 12 wherein said tubular scintillator elements are surrounded by several rings of holes in a loosely connected matrix.

16. A method of manufacturing a Photonic Bandgap Crystal Scintillator array of tubular scintillators wherein each tubular scintillator has a diameter of less than 10 micron and spaced at less than 1 micron apart wherein said method comprises the steps of;

a creating first mold of holes of a diameter less than 10 micron and distances of less than 1 micron apart, in solid material by one of the processes comprising a1 femtolaser ablating, a2 UV laser irradiating followed by chemical etching, a3 nano-imprinting followed by plasma etching and electroplating wherein said solid material is one of a group comprising scintialltor, a glass, a plastic, a metal, an elastomer, a gel or an aerogel;

b creating a second mold of tubular scintillators by one of the processes of b1 extruding a viscous substance through the holes of the first mold and solidifying it by heat of light wherein said substance is one of a group comprising a heat liquefied scintillator, a phot-polymer, a solvent liquefied substance, an epoxy or a sol in the process of being gelated b2 curing tubular scintillators of a photo-polymer with a tubular light beam delimited by the holes of the first mold, while extracting the non-polymerized solution around the polymerized tubular scintillators, while the light polymerization process advances in the photo-polymer along tubular lines b3 depositing vapors of a superheated melt passing through the holes of the first mold and crystallizing on a cooled template of pointed elevations, wherein each such elevation is in front of a hole of a first mold, wherein an electrostatic field is established between the first mold and said template of pointed elevations and wherein the cooled template is slowly retrieved as the tubular crystals height grows;

c creating a third mold of holes in matrix by c1 filling the space between the tubular scintillators of the second mold with a substance wherein said substance is one of a group comprising a heat liquefied scintillator, a phot-polymer, a solvent liquefied substance, an elastomer, an epoxy or a sol-gel and c2 solidifying said substance by one of the processes comprising cooling, polymerizing, curing or gelating c3 eliminating the tubular elements within the third mold by heat, chemical etching, stripping or breaking;

d filling one of the first, second or third molds with an ultrafine powder of nanosized particles of size less than 100 nm, of a scintillator material tha thas a melting temperature lower than that of the mold;

e crystallizing the material within the mold by e1 heating it above the melting temperature of the scintillator and melting it e2 placing around the shorter section of the mold two sets of closely spaced inductor heaters, and IR lasers, wherein the two sets of heaters and IR lasers establish within the melt a gradient of temperature from below the melting temperature to above the melting temperature, within a short distance, e3 advancing the temperature gradient front slowly across the mold by moving the inductive heaters and IR lasers and crystallizing the melt at the lower side of the temperature gradient;

f after slowly cooling the crystal to avoid cracks, eliminating the mold by one of the methods consisting of heating, chemical etching, stripping, breaking or shattering by ultrasound irradiation or leaving the aerogel in place to support the structure of columns.

17. A method of manufacturing a Photonic Bandgap Crystal Scintillator array as in claim 16 whereas a first mold is prepared by nano-imprinting a metallic plate followed by plasma etching and electroplating and further extruding a liquefied glass scintillator through the holes of said first mold and solidifying it by heat.

18. A method of manufacturing a Photonic Bandgap Crystal Scintillator array as in claim 17 whereas the extruded substance is photo-polymer including doped p-terphenyl.

19. A method of manufacturing a Photonic Bandgap Crystal Scintillator array as in claim 17 whereas the vapors of a superheated melt of a Lanthanum Chloride Bromide scintillator passing through the holes of the said first mold are deposited on the pointed elevations of the cooled template aided by an electrostatic field between the mold whereas the cooled template is slowly retrieved.

20. A method of manufacturing a Photonic Bandgap Crystal Scintillator array in claim 17 whereas the vapors of a superheated melt of a Yittrium Gadolinium Oxide scintillator passing through the holes of the said first mold are deposited on the pointed elevation sof the cooled template aided by an electrostatic field between the mold.

21. A method of manufacturing a Photonic Bandgap Crystal Scintillator array as in claim 16 comprising the steps of creating a first mold by nano-imprinting a metallic plate followed by plasma etching and electroplating and further creating a second mold by extruding a photo-polymer throught he holes of said first mold and solidifying it by UV light and further creating a third mold by filling the space between the polymerized tubular elements by an aerogel through a sol-gel process and further eliminating the polymerized tubular elements by heat and sintering the aerogel matrix by heating it above 1000° and further filling the holes of the glassy mold with nano-crystal of Lanthanum Chloride Bromide and melting them at 950° and crystallizing the scintillator in the holes, and leaving the aerogel matrix in place to support the Lanthanum Chloride Bromide structure of columns.

* * * * *